(12) United States Patent
Reddy et al.

(10) Patent No.: US 12,042,492 B2
(45) Date of Patent: Jul. 23, 2024

(54) BACE1 INHIBITORY LIGAND MOLECULES AGAINST AMYLOID BETA-INDUCED SYNAPTIC AND MITOCHONDRIAL TOXICITIES

(71) Applicant: Texas Tech University System, Lubbock, TX (US)

(72) Inventors: P. Hemachandra Reddy, Lubbock, TX (US); Jangampalli Adi Pradeepkiran, Lubbock, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 17/496,921

(22) Filed: Oct. 8, 2021

(65) Prior Publication Data

US 2022/0110931 A1 Apr. 14, 2022

Related U.S. Application Data

(60) Provisional application No. 63/089,958, filed on Oct. 9, 2020.

(51) Int. Cl.
| | | |
|---|---|---|
| *A61K 31/473* | (2006.01) | |
| *A61K 31/222* | (2006.01) | |
| *A61K 31/395* | (2006.01) | |
| *A61K 31/4015* | (2006.01) | |
| *A61K 31/4196* | (2006.01) | |
| *G16B 15/30* | (2019.01) | |

(52) U.S. Cl.
CPC .......... *A61K 31/473* (2013.01); *A61K 31/222* (2013.01); *A61K 31/395* (2013.01); *A61K 31/4015* (2013.01); *A61K 31/4196* (2013.01); *G16B 15/30* (2019.02)

(58) Field of Classification Search
CPC .................................................. A61K 31/473
See application file for complete search history.

(56) References Cited

U.S. PATENT DOCUMENTS

| | | |
|---|---|---|
| 8,987,255 B2 | 3/2015 | Woltering |
| 9,163,011 B2 | 10/2015 | Lueoend et al. |
| 9,353,084 B2 | 5/2016 | Juhl et al. |
| 9,828,350 B2 | 11/2017 | Trabanco-Suárez et al. |
| 2015/0322054 A1 | 11/2015 | Hilbert et al. |

OTHER PUBLICATIONS

Predeepkiran et al., "Protective effects of BACE1 inhibitory ligand molecules against amyloid beta-induced synaptic and mitochondrial toxicitesi in Alzheimer's disease", Human Molecular Genetics, vol. 29, pp. 49-69, Oct. 9, 2019 (Year: 2019).*
"pCAX APP Swe/IND", AddGene, Dec. 26, 2007 (Year: 2007).*
Ghosh et al., "BACE1 (β-Secretase) Inhibitors for the Treatment of Alzheimer's Disease", Chem Soc Rev. Oct. 7, 2014; 43(19): 6765-6813 (Year: 2014).*
"Drug Carriers", Harvard, Aug. 9, 2015 (Year: 2015).*
Kontos et al., "The Effect of an Estrone d-Lactam Steroid Ester Derivative on Breast Cancer Cells and Its Predicted Binding Interactions With the Ligand Binding Domain of Estrogen Receptor", Oncology Research, vol. 16, pp. 129-142, Feb. 2, 2005 (Year: 2005).*
Angelova, P.R., and Abramov, A.Y. (2018) Role of mitochondrial ROS in the brain: from physiology to neurodegeneration. FEBS Lett. 592, 692-702.
Baek, S.H., et al., (2017) Inhibition of Drp1 Ameliorates Synaptic Depression, AB Deposition, and Cognitive Impairment in an Alzheimer's Disease Model. J. Neurosci. 37, 5099-5110.
Binkowski, T.A., et al., (2003) CASTp: Computed Atlas of Surface Topography of proteins. Nucleic Acids Res. 31, 3352-3355.
Bird, T.D. (2008) Genetic aspects of Alzheimer disease. Genet Med. 10, 231-9.
Birnbaum, J.H., et al., (2018) Oxidative stress and altered mitochondrial protein expression in the absence of amyloid-β and tau pathology in iPSC-derived neurons from sporadic Alzheimer's disease patients. Stem Cell Res. 27, 121-130.
Butterfield, D.A., et al., (2002) Evidence that amyloid beta-peptide-induced lipid peroxidation and its sequelae in Alzheimer's disease brain contribute to neuronal death. Neurobiol. Aging. 5, 655-64.
Cai, Y., et al., (2015) Mutations in presenilin 2 and its implications in Alzheimer's disease and other dementia-associated disorders. Clin. Interv. Aging. 10, 1163-72.
Calkins, M.J., et al., (2011) Impaired mitochondrial biogenesis, defective axonal transport of mitochondria, abnormal mitochondrial dynamics and synaptic degeneration in a mouse model of Alzheimer's disease. Hum. Mol. Genet. 20, 4515-29.
Casey, D.A., et al., (2010) Drugs for Alzheimer's disease: are they effective? P T. 35, 208-211.
Cha, M.Y., et al., (2012) Mitochondria-specific accumulation of amyloid β induces mitochondrial dysfunction leading to apoptotic cell death. PLoS One. 7, e34929.
Cheng, F., et al., (2012) admetSAR: a comprehensive source and free tool for assessment of chemical ADMET properties. J. Chem. Inf. Model. 52, 3099-3105.
Chow, V.W., et al., (2010) An overview of APP processing enzymes and products. Neuromolecular Med. 12, 1-12.
Coimbra, J.R.M., et al. (2018) Highlights in BACE1 Inhibitors for Alzheimer's Disease Treatment. Frontiers in Chemistry 6:178.
Cole, S.L., and Vassar, R. (2008) The role of amyloid precursor protein processing by BACE1, the beta-secretase, in Alzheimer disease pathophysiology. J. Biol. Chem. 31, 29621-29625.
Cowan, K., et al., (2019) Mitochondrial integrity in neurodegeneration. CNS Neurosci Ther. doi: 10.1111/cns.13105.
Dallakyan, S., and Olson, A.J. (2015) Small-molecule library screening by docking with PyRx. Methods. Mol. Biol. 1263: 243-250.
Dragicevic, N., et al., (2010) Mitochondrial amyloid-beta levels are associated with the extent of mitochondrial dysfunction in different brain regions and the degree of cognitive impairment in Alzheimer's transgenic mice. J. Alzheimers. Dis. 20 Suppl 2, S535-50.

(Continued)

*Primary Examiner* — Andrew D Kosar
*Assistant Examiner* — Gillian A Hutter
(74) *Attorney, Agent, or Firm* — Edwin S. Flores; Daniel J. Chalker; Chalker Flores, LLP

(57) ABSTRACT

The present invention includes a method of inhibiting an activity of a BACE1 protein comprising contacting the BACE1 protein with a ligand that specifically inhibits residue Asp 32 of the human BACE1 protein.

15 Claims, 18 Drawing Sheets

Specification includes a Sequence Listing.

(56) References Cited

OTHER PUBLICATIONS

Du, H., et al., (2010) Early deficits in synaptic mitochondria in an Alzheimer's disease mouse model. Proc. Natl. Acad. Sci. U S A. 107, 18670-5.
Fenoglio, C., et al., (2018) Role of Genetics and Epigenetics in the Pathogenesis of Alzheimer's Disease and Frontotemporal Dementia. J. Alzheimers. Dis. 62, 913-932.
Gao, Y., et al., (2019) Mutation profile of App, PSEN1, and PSEN2 in Chinese familial Alzheimer's disease. Neurobiol. Aging. 77, 154-157.
Gutala, R.V., and Reddy, P.H. (2004) The use of real-time PCR analysis in a gene expression study of Alzheimer's disease postmortem brains. J. Neurosci. Methods. 132, 101-7.
Haass, C., et al., (2012) Trafficking and proteolytic processing of APP. Cold. Spring. Harb. Perspect. Med. 2, a006270.
Hasegawa, H., et al., (2014) The FAM3 superfamily member ILEI ameliorates Alzheimer's disease-like pathology by destabilizing the penultimate amyloid-β precursor. Nat. Commun. 5, 3917.
Hu, H., et al., (2019) Structure-Based Survey of the Binding Modes of BACE1 Inhibitors. ACS. Chem. Neurosci, 10, 880-889.
Kametani, F., and Hasegawa, M. (2018) Reconsideration of Amyloid Hypothesis and Tau Hypothesis in Alzheimer's Disease. Front. Neurosci. 30, 25.
Kim, S., et al., (2016) PubChem Substance and Compound databases. Nucleic. Acids. Res. 44, D1202-13.
Kimura, A., et al., (2016) Alternative Selection of β-Site APP-Cleaving Enzyme 1 (BACE1) Cleavage Sites in Amyloid β-Protein Precursor (APP) Harboring Protective and Pathogenic Mutations within the Aβ Sequence. J. Biol. Chem. 291, 24041-24053.
Li, N., et al., (2016) Effect of Presenilin Mutations on APP Cleavage; Insights into the Pathogenesis of FAD. Front. Aging. Neurosci. 8, 51.
Luo, Y., et al., (2001) Mice deficient in BACE1, the Alzheimer's beta-secretase, have normal phenotype and abolished beta-amyloid generation. Nat. Neurosci. 4, 231-232.
Manczak, M., et al., (2006) Mitochondria are a direct site of A beta accumulation in Alzheimer's disease neurons: Implications for free radical generation and oxidative damage in disease progression. Hum. Mol. Genet. 15, 1437-49.
Manczak, M., et al., (2016) Protective effects of reduced dynamin-related protein 1 against amyloid beta-induced mitochondrial dysfunction and synaptic damage in Alzheimer's disease. Hum. Mol. Genet. 25, 5148-5166.
Manczak, M., et al., (2019) Mitochondrial division inhibitor 1 reduces dynamin-related protein 1 and mitochondrial fission activity. Hum. Mol. Genet. 28, 177-199.
Masters, C.L., and Selkoe, D.J. (2012) Biochemistry of Amyloid β-Protein and Amyloid Deposits in Alzheimer Disease. Cold Spring Harb. Perspect. Med. 2, a006262.
Mirsafian, H., et al., (2014) Bin Mohamad S. Amino acid sequence and structural comparison of BACE1 and BACE2 using evolutionary trace method. ScientificWorldJournal; 482463.
Morris, G.P., et al., (2012) Inconsistencies and controversies surrounding the amyloid hypothesis of Alzheimer's disease. Acta. Neuropathol. Commun. 18, 135.
Moussa-Pacha, N. M., et al. (2019) BACE1 inhibitors: Current status and future directions in treating Alzheimer's disease. Medicinal Research Reviews 40:339-384.
Nieweg, K., et al., (2015) Alzheimer's disease-related amyloid-β induces synaptotoxicity in human iPS cell-derived neurons. Cell Death. Dis. 6, e1709.
Ohno, M., et al., (2004) BACE1 deficiency rescues memory deficits and cholinergic dysfunction in a mouse model of Alzheimer's disease. Neuron. 41, 27-33.

Oka, S., et al., (2016) Human mitochondrial transcriptional factor A breaks the mitochondria-mediated vicious cycle in Alzheimer's disease. Sci. Rep. 6, 37889.
Otsuka I, et al., (2017) Aberrant telomere length and mitochondrial DNA copy number in suicide completers. Sci. Rep. 7, 3176.
Palop, J.J., and Mucke, L. (2010) Amyloid-beta-induced neuronal dysfunction in Alzheimer's disease: from synapses toward neural networks. Nat. Neurosci. 13, 812-8.
Panchal, K., and Tiwari, A.K. (2018) Mitochondrial dynamics, a key executioner in neurodegenerative diseases. Mitochondrion. S1567-7249 30120-X.
Pelegay, E.C., et al., (2019) Targeting Mitochondrial Defects to Increase Longevity in Animal Models of Neurodegenerative Diseases. Adv. Exp. Med. Biol. 1134, 89-110.
Pereira, C., et al., (2005) Alzheimer's disease-associated neurotoxic mechanisms and neuroprotective strategies. Curr. Drug. Targets. CNS Neurol. Disord. 4, 383-40.
Poirier, Y., et al., (2019) Link between the unfolded protein response and dysregulation of mitochondrial bioenergetics in Alzheimer's disease. Cell. Mol. Life. Sci. 76, 1419-1431.
Rajmohan, R., and Reddy, P.H. (2017) Amyloid-Beta and Phosphorylated Tau Accumulations Cause Abnormalities at Synapses of Alzheimer's disease Neurons. J. Alzheimers. Dis. 57, 975-999.
Reddy, P.H. (2006) Amyloid precursor protein-mediated free radicals and oxidative damage: implications for the development and progression of Alzheimer's disease. J. Neurochem. 96, 1-13.
Reddy, P.H. (2011) Abnormal tau, mitochondrial dysfunction, impaired axonal transport of mitochondria, and synaptic deprivation in Alzheimer's disease. Brain. Res. 1415, 136-48.
Reddy, P.H. (2013) Amyloid beta-induced glycogen synthase kinase 3B phosphorylated VDAC1 in Alzheimer's disease: implications for synaptic dysfunction and neuronal damage. Biochim. Biophys. Acta. 1832, 1913-21.
Reddy, P.H., et al., (2010) Amyloid-beta and mitochondria in aging and Alzheimer's disease: implications for synaptic damage and cognitive decline. J. Alzheimers. Dis. 20, S499-512.
Reddy, P.H., et al., (2016) Protective effects of a natural product, curcumin, against amyloid β induced mitochondrial and synaptic toxicities in Alzheimer's disease. J. Investig. Med. 64, 1220-1234.
Reddy, P.H., et al., (2018) Synergistic Protective Effects of Mitochondrial Division Inhibitor 1 and Mitochondria-Targeted Small Peptide SS31 in Alzheimer's Disease. J. Alzheimers. Dis. 62, 1549-1565.
Roberds, S.L., et al., (2001) BACE knockout mice are healthy despite lacking the primary beta-secretase activity in prain: implications for Alzheimer's disease therapeutics. Hum. Mol. Genet. 10, 1317-1324.
Singh. S.K., et al., (2016) Overview of Alzheimer's Disease and Some Therapeutic Approaches Targeting Aβ by Using Several Synthetic and Herbal Compounds. Oxid. Med. Cell. Longev. 7361613.
Trott, O., and Olson, A.J., (2010) AutoDock Vina: improving the speed and accuracy of docking with a new scoring function, efficient optimization, and multithreading. J. Comput. Chem. 30, 455-461.
Vassar, R. (2014) BACE1 inhibitor drugs in clinical trials for Alzheimer's disease. Alzheimer's Research & Therapy 6:89.
Wang, X., et al., (2008) Amyloid-beta overproduction causes abnormal mitochondrial dynamics via differential modulation of mitochondrial fission/fusion proteins. Proc. Natl. Acad. Sci. U S A. 105, 19318-23.
Wang, X., et al., (2009). Impaired balance of mitochondrial fission and fusion in Alzheimer's disease. J. Neurosci. 29, 9090-103.
Wolber, G., and Langer, T. (2005) LigandScout: 3-D pharmacophores derived from protein-bound ligands and their use as virtual screening filters. J. Chem. Inf. Model. 45, 160-169.
Yan, R., and Vassar, R. (2014) Targeting the β secretase BACE1 for Alzheimer's disease therapy. Lancet Neurol. 13, 319-29.
Yin, J., et al., (2018) Amyloid-β Increases Tau by Mediating Sirtuin 3 in Alzheimer's Disease. Mol. Neurobiol. 55, 8592-8601.

* cited by examiner

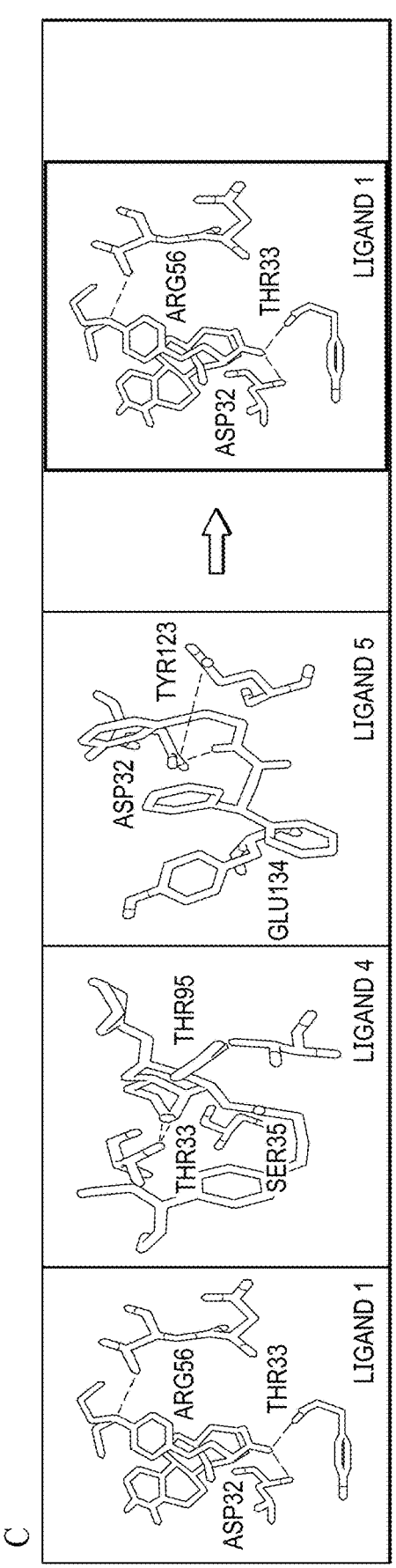
FIG. 3C
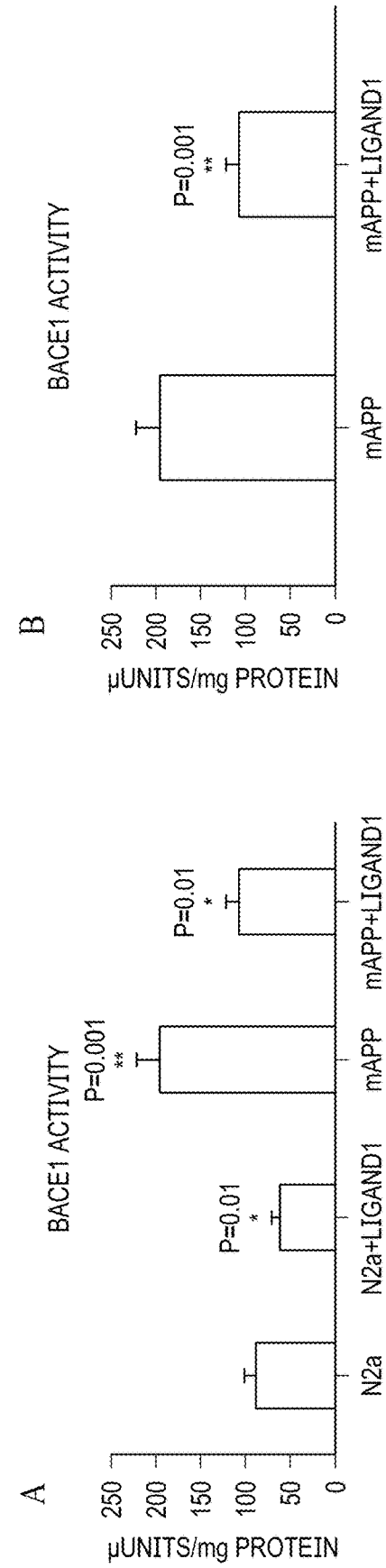
FIG. 4A
FIG. 4B

SEQUENCE LISTING

```
<160> NUMBER OF SEQ ID NOS: 32

<210> SEQ ID NO 1
<211> LENGTH: 20
<212> TYPE: DNA
<213> ORGANISM: Artificial Sequence
<220> FEATURE:
<223> OTHER INFORMATION: Synthetic: Drp1 Forward Primer

<400> SEQUENCE: 1
atgccagcaa gtccacagaa                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic: Drp1 Reverse Primer

<400> SEQUENCE: 2
tgttctcggg cagacagttt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic: Fis1 Forward Primer

<400> SEQUENCE: 3
caaagaggaa cagcgggact                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic: Fis1 Reverse Primer

<400> SEQUENCE: 4
```
acagccctcg cacatacttt                                               20

<210> SEQ ID NO 5
<211> LENGTH: 20
<212> TYPE: DNA
<213> ORGANISM: Artificial Sequence
<220> FEATURE:
<223> OTHER INFORMATION: Synthetic: Mfn1 Forward Primer

<400> SEQUENCE: 5
gcagacagca catggagaga                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic: Mfn1 Reverse Primer

<400> SEQUENCE: 6
gatccgattc cgagcttccg                                               20

<210> SEQ ID NO 7
<211> LENGTH: 21
<212> TYPE: DNA
<213> ORGANISM: Artificial Sequence
<220> FEATURE:
<223> OTHER INFORMATION: Synthetic: Mfn2 Forward Primer

<400> SEQUENCE: 7
tgcaccgcca tatagaggaa g                                             21

<210> SEQ ID NO 8
<211> LENGTH: 20
<212> TYPE: DNA
<213> ORGANISM: Artificial Sequence
<220> FEATURE:
<223> OTHER INFORMATION: Synthetic: Mfn2 Reverse Primer

<400> SEQUENCE: 8
tctgcagtga actggcaatg                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic: Opa1 Forward Primer

<400> SEQUENCE: 9
accttgccag tttagctccc                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic: Opa1 Reverse Primer

<400> SEQUENCE: 10
ttgggacctg cagtgaagaa                                               20

<210> SEQ ID NO 11
<211> LENGTH: 20
<212> TYPE: DNA
<213> ORGANISM: Artificial Sequence

```
<220> FEATURE:
<223> OTHER INFORMATION: Synthetic: PGC1-alpha Forward Primer

<400> SEQUENCE: 11
gcagtcgcaa catgctcaag                                           20

<210> SEQ ID NO 12
<211> LENGTH: 20
<212> TYPE: DNA
<213> ORGANISM: Artificial Sequence
<220> FEATURE:
<223> OTHER INFORMATION: Synthetic: PGC1-alpha Reverse Primer

<400> SEQUENCE: 12 gggaacccctt ggggtcattt                                          20

<210> SEQ ID NO 13
<211> LENGTH: 20
<212> TYPE: DNA
<213> ORGANISM: Artificial Sequence
<220> FEATURE:
<223> OTHER INFORMATION: Synthetic: Nrf1 Forward Primer

<400> SEQUENCE: 13
agaaacggaa acggcctcat                                           20

<210> SEQ ID NO 14
<211> LENGTH: 20
<212> TYPE: DNA
<213> ORGANISM: Artificial Sequence
<220> FEATURE:
<223> OTHER INFORMATION: Synthetic: Nrf1 Reverse Primer

<400> SEQUENCE: 14
catccaacgt ggctctgagt                                           20

<210> SEQ ID NO 15
<211> LENGTH: 20
<212> TYPE: DNA
<213> ORGANISM: Artificial Sequence
<220> FEATURE:
<223> OTHER INFORMATION: Synthetic: Nrf2 Forward Primer

<400> SEQUENCE: 15
atggagcaag tttggcagga                                           20

<210> SEQ ID NO 16
<211> LENGTH: 20
<212> TYPE: DNA
<213> ORGANISM: Artificial Sequence
<220> FEATURE:
<223> OTHER INFORMATION: Synthetic: Nrf2 Reverse Primer

<400> SEQUENCE: 16
gctgggaaca gcggtagtat                                           20

<210> SEQ ID NO 17
<211> LENGTH: 20
<212> TYPE: DNA
<213> ORGANISM: Artificial Sequence
<220> FEATURE:
<223> OTHER INFORMATION: Synthetic: TFAM Forward Primer

<400> SEQUENCE: 17
tccacagaac agctacccaa                                           20
```

<210> SEQ ID NO 18
<211> LENGTH: 20
<212> TYPE: DNA
<213> ORGANISM: Artificial Sequence
<220> FEATURE:
<223> OTHER INFORMATION: Synthetic: TFAM Reverse Primer

<400> SEQUENCE: 18
ccacagggct gcaattttcc                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic: Synaptophysin Forward Primer

<400> SEQUENCE: 19
ctgcgttaaa gggggcacta                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic: Synaptophysin Reverse Primer

<400> SEQUENCE: 20
acagccacgg tgacaaagaa                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic: PSD95 Forward Primer

<400> SEQUENCE: 21
cttcatcctt gctggggtc                                               20

<210> SEQ ID NO 22
<211> LENGTH: 20
<212> TYPE: DNA
<213> ORGANISM: Artificial Sequence
<220> FEATURE:
<223> OTHER INFORMATION: Synthetic: PSD95 Reverse Primer

<400> SEQUENCE: 22
ttgcggaggt caacaccatt                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic: APP-Human Forward Primer

<400> SEQUENCE: 23
tggaggtacc cactgatggt                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic: APP-Human Reverse Primer

```
<400> SEQUENCE: 24
tgtgcatgtt cagtctgcca                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic: BACE1 Forward Primer

<400> SEQUENCE: 25
gcgaattggc tttgctgtca                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic: BACE1 Reverse Primer

<400> SEQUENCE: 26
tgtctgccgt aacaaacgga                                          20

<210> SEQ ID NO 27
<211> LENGTH: 20
<212> TYPE: DNA
<213> ORGANISM: Artificial Sequence
<220> FEATURE:
<223> OTHER INFORMATION: Synthetic: Presenilin1 Forward Primer

<400> SEQUENCE: 27
agacctacaa tgtcgccgtg                                          20

<210> SEQ ID NO 28
<211> LENGTH: 20
<212> TYPE: DNA
<213> ORGANISM: Artificial Sequence
<220> FEATURE:
<223> OTHER INFORMATION: Synthetic: Presenilin1 Reverse Primer

<400> SEQUENCE: 28
agtggatggc aatcatcccg                                          20

<210> SEQ ID NO 29
<211> LENGTH: 23
<212> TYPE: DNA
<213> ORGANISM: Artificial Sequence
<220> FEATURE:
<223> OTHER INFORMATION: Synthetic: B-actin Forward Primer

<400> SEQUENCE: 29
agaagctgtg ctatgttgct cta                                      23

<210> SEQ ID NO 30
<211> LENGTH: 21
<212> TYPE: DNA
<213> ORGANISM: Artificial Sequence
<220> FEATURE:
<223> OTHER INFORMATION: Synthetic: B-actin Reverse Primer

<400> SEQUENCE: 30
tcaggcagct catagctctt c                                        21

<210> SEQ ID NO 31
```

```
<211> LENGTH: 18
<212> TYPE: DNA
<213> ORGANISM: Artificial Sequence
<220> FEATURE:
<223> OTHER INFORMATION: Synthetic: GAPDH Forward Primer

<400> SEQUENCE: 31
ttcccgttca gctctggg                                              18

<210> SEQ ID NO 32
<211> LENGTH: 18
<212> TYPE: DNA
<213> ORGANISM: Artificial Sequence
<220> FEATURE:
<223> OTHER INFORMATION: Synthetic: GAPDH Reverse Primer

<400> SEQUENCE: 32
ccctgcatcc actggtgc                                              18
```

BACE1 INHIBITORY LIGAND MOLECULES AGAINST AMYLOID BETA-INDUCED SYNAPTIC AND MITOCHONDRIAL TOXICITIES

CROSS-REFERENCE TO RELATED APPLICATIONS

This application claims priority to U.S. Provisional Application Ser. No. 63/089,958, filed Oct. 9, 2020, the entire contents of which are incorporated herein by reference.

STATEMENT OF FEDERALLY FUNDED RESEARCH

This invention was made with government support under R01AG042178, R01AG47812, R01NS105473 awarded by the National Institutes of Health/NSF/DARPA. The government has certain rights in the invention.

TECHNICAL FIELD OF THE INVENTION

The present invention relates in general to the field of BACE1 inhibitory ligand molecules, and more particularly, to the use of these inhibitors to reduce amyloid beta-induced synaptic and mitochondrial toxicities.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Oct. 7, 2021, is named TECH1128_SeqList.txt and is 7, kilo bytes in size.

BACKGROUND OF THE INVENTION

Without limiting the scope of the invention, its background is described in connection with Alzheimer's disease (AD).

Alzheimer's disease (AD) is a progressive, irreversible brain disorder which causes the degeneration, and eventual death, of brain cells. AD is also the most common cause of "dementia"—a series of symptoms characterized by a continuous decline in memory, communication skills, behavioral skills, thinking, and a person's ability to function independently. While early signs of AD include forgetting recent events or conversations, as the disease progresses, patients develop severe memory impairment. Advanced stages of AD are even known to cause complications associated with severe loss of brain function such as dehydration and malnutrition. While the exact cause of AD is still unknown, age is the best known risk factor. AD is the $6^{th}$ leading cause of death in the United States. More than five million Americans are currently living with AD, and this number is expected to nearly triple to fourteen million by 2060. Currently, 50% of primary care physicians in the United States believe that the medical profession is unprepared to face the growing number of AD patients moving forward.

There is no known cure for AD; however, current approaches to treatment primarily focus on alleviating symptoms in order to help patients maintain mental function, manage behavior, and temporarily delay the disease's progress. Several prescription drugs have been approved by the Food and Drug Administration (FDA) for AD treatment. For example, cholinesterase inhibitors—such as Razadyne (galantamine), Exelon (rivastigmine), and Aricept (donepezil)—help to control behavioral symptoms by preventing the breakdown of acetylcholine. Acetylcholine is a brain chemical associated with memory and thinking, so cholinesterase inhibitors can be effective for a time in some patients. However, as AD progresses, the patient's brain produces less acetylcholine, rendering the drugs ineffective for late stage victims. In terms of treatment options for moderate to severe AD cases, medications such as Namenda (memantine), and N-methyl D-aspartate (NMDA) antagonist, are used to help patients maintain daily functions and some independence by regulating glutamate—a brain chemical linked to cell death when produced in excess. While the current range of medications on the market offer a limited amount of symptom relief, researchers continue to search for superior drug and treatment options.

In recent years, one promising area of research for the treatment of AD centers on the use of beta secretase 1 enzyme (BACE1) inhibitors. BACE 1 is an enzyme which cleaves amyloid precursor protein (APP)—an integral membrane protein found in the synapses of brain neurons. When APP is cleaved by BACE1 it forms neurotoxic Amyloid-β (Aβ) peptides which are now considered to have a crucial role in the early development of AD and the cognitive decline of patients. Aβ peptides clump together and eventually form harmful plaques surrounding brain neurons. Accumulation of Aβ in cells results in oxidative damage, tau hyperphosphorylation, inflammatory responses, mitochondrial damage and synaptic failure. In light of this, drugs which inhibit BACE 1 in order to stop abnormal APP processing, and reduce the amount of Aβ in AD neurons, have been an area of intense interest in the field. While clinical trials have been conducted on BACE 1 inhibitor drugs such as JNJ54861911, CNP520, LY3202626, Elenbecestat, Lanabecestat and Verubecestat, it has been found that these drugs have: harmful side effects, difficulty passing through the blood-brain barrier, or been ineffective in reducing cognitive decline and disease progression.

What are needed are novel therapies that prevent the accumulation of amyloid beta, thus preventing the onset of disease.

SUMMARY OF THE INVENTION

In one embodiment, the present invention includes a method of inhibiting an activity of a BACE1 protein comprising: contacting the BACE1 protein with a ligand that specifically inhibits at one or more residues selected from ASP 32, GLY 34, SER 35, SER 36, ASN 37 and ARG 128 of the human BACE1 protein. In one aspect, the ligand is selected from:

[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate,
[(1,4-Dihydroxy-9,10-dioxoanthracen-2-yl)-phenylmethyl] 4-[4-[bis(2-chloroethyl)amino]phenyl]butanoate,
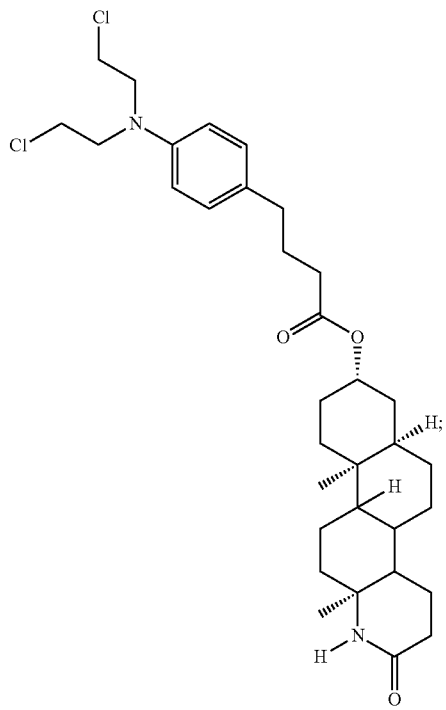
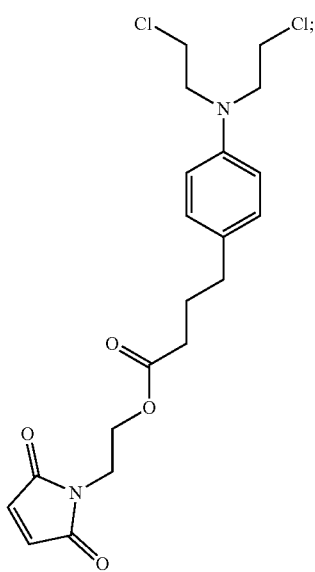 [SMILES: O=C(CCCc1ccc(N(CCCl)CCCl)cc1)OCCN1C(=O)C=CC1=O]
2-(2,5-Dioxopyrrol-1-yl)ethyl 4-[4-[bis(2-chloroethyl)amino]phenyl]butanoate,
4-Chloro-3-fluoro-N-[(1R)-2-methyl-1-(2-methyl-1,2,4-triazol-3-yl)propyl]benzamide,
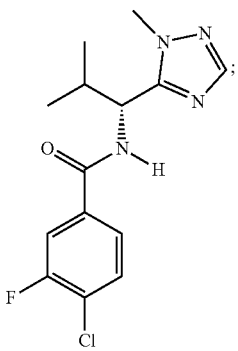 [SMILES: CC(C)[C@@H](NC(=O)c1ccc(Cl)c(F)c1)c1ncnn1C]

or (2S)-4-[4-[Bis(2-chloroethyl)amino]phenyl]-2-[4-[(2S,9S)-9-[4-[[(1R)-3-[4-bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

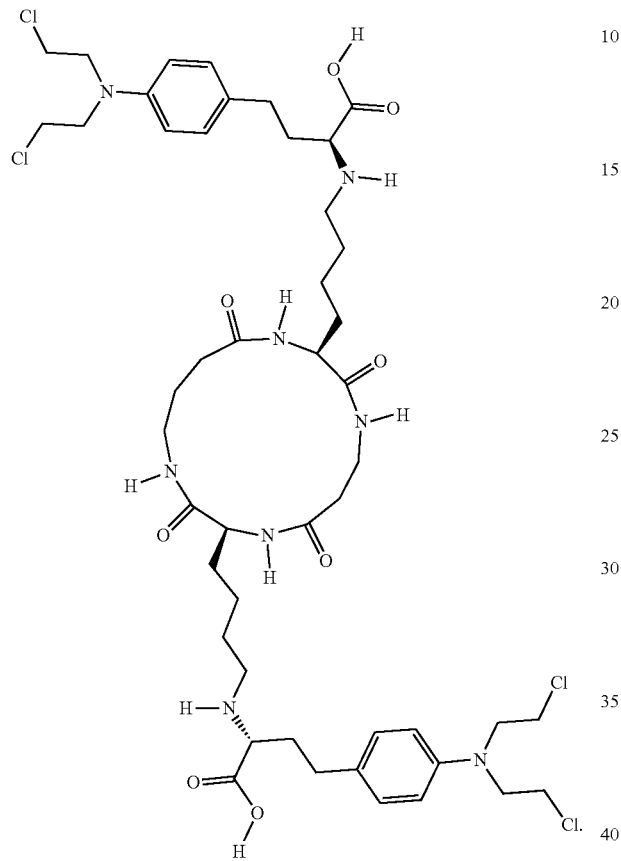

In another aspect, the ligand is formulated in a pharmaceutical composition. In another aspect, the ligand is formulated with a pharmaceutically acceptable carrier, diluent, or excipient. In another aspect, the ligand is formulated for oral, enteral, parenteral, pulmonary, or intravenous administration. In another aspect, the effective amount is between about 1, 2, 3, 4, 5, 6, 7, 8, 9, 10, 11, 12, 13, 14, 15, 16, 17, 18, 19 or 20. In another aspect, the ligand is provided between about 1-20 mg kg body weight, 1-7 times per week, 5-15 mg kg body weight, 2-6 times per week, or 8-12 mg kg body weight, 3-5 times per week, or 10 mg kg body weight, 3 times per week.

In another embodiment, the present invention includes a method of treating Alzheimer's Disease, the method comprising: administering to the individual an effective amount of at least one compound that specifically inhibits human BACE1 protein activity by interaction with one or more residues selected from ASP 32, GLY 34, SER 35, SER 36, ASN 37 and ARG 128. In one aspect, the compound is selected from:

[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate,

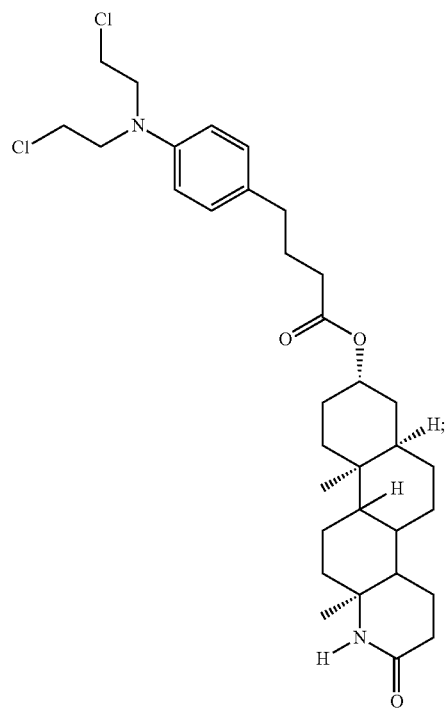

2-(2,5-Dioxopyrrol-1-yl)ethyl 4-[4-[bis(2-chloroethyl)amino]phenyl]butanoate,

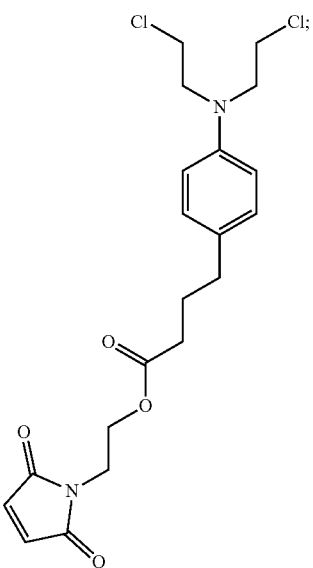 [SMILES: O=C(CCCc1ccc(N(CCCl)CCCl)cc1)OCCN1C(=O)C=CC1=O]

[(1,4-Dihydroxy-9,10-dioxoanthracen-2-yl)-phenylmethyl] 4-[4-[bis(2-chloroethyl)amino]phenyl]butanoate, or (2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

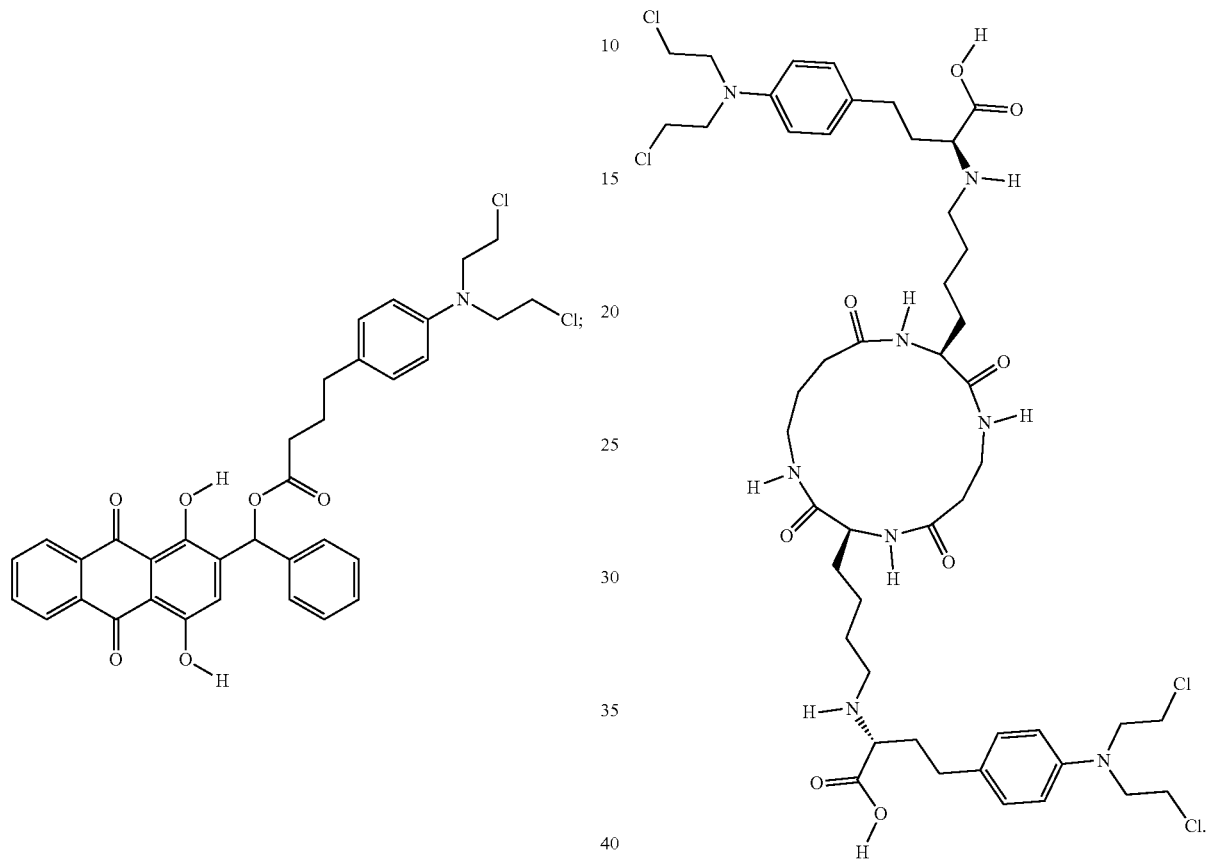

4-Chloro-3-fluoro-N-[(1R)-2-methyl-1-(2-methyl-1,2,4-triazol-3-yl)propyl]benzamide,

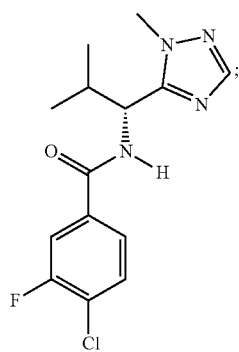

In another aspect, the compound is formulated in a pharmaceutical composition. In another aspect, the compound is formulated with a pharmaceutically acceptable carrier, diluent, or excipient. In another aspect, the compound is formulated for oral, enteral, parenteral, pulmonary, or intravenous administration. In another aspect, the ligand is provided between about 1-20 mg kg body weight, 1-7 times per week, 5-15 mg kg body weight, 2-6 times per week, or 8-12 mg kg body weight, 3-5 times per week, or 10 mg kg body weight, 3 times per week.

In another embodiment, the present invention includes a method of identifying inhibitors of BACE1 activity comprising: obtaining a database of pharmacophore-based ligand(s) with supramolecular properties; selecting from the database one or more template ligands that are "aspartic protease inhibitors; and modeling in silico one or more pharmacophore-based ligand(s) with supramolecular properties that directly binds to one or more residues selected from ASP 32, GLY 34, SER 35, SER 36, ASN 37 and ARG 128 of BACE1 to inhibit the activity of BACE1. In another aspect, the inhibitors are selected from: In another aspect, the ligand is provided between about 1-20 mg kg body weight, 1-7 times per week, 5-15 mg kg body weight, 2-6 times per week, or 8-12 mg kg body weight, 3-5 times per week, or 10 mg kg body weight, 3 times per week.

9
[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate,
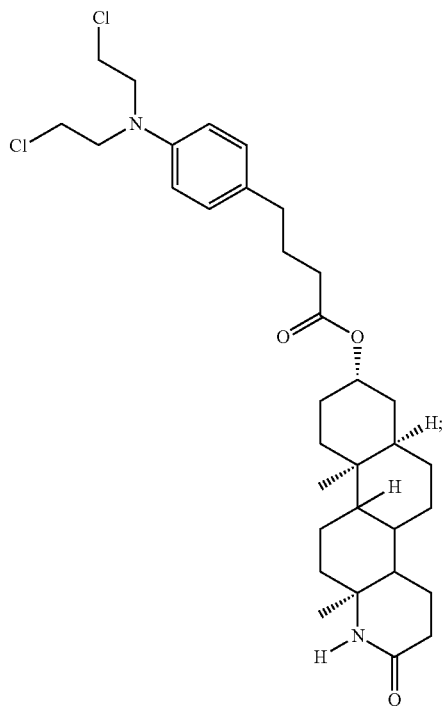
2-(2,5-Dioxopyrrol-1-yl)ethyl 4-[4-[bis(2-chloroethyl)amino]phenyl]butanoate,
10
[(1,4-Dihydroxy-9,10-dioxoanthracen-2-yl)-phenylmethyl] 4-[4-[bis(2-chloroethyl)amino]phenyl]butanoate,
4-Chloro-3-fluoro-N-[(1R)-2-methyl-1-(2-methyl-1,2,4-triazol-3-yl)propyl]benzamide, or
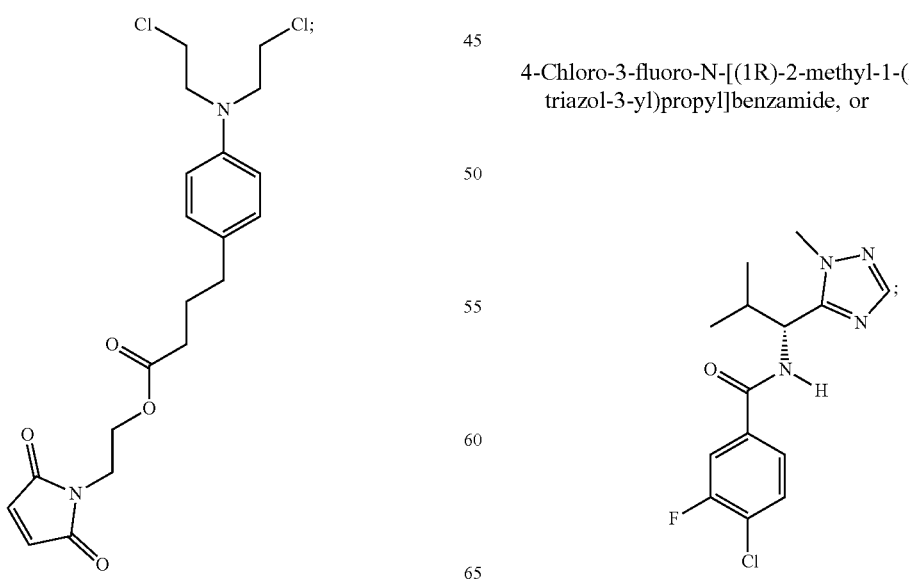

(2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

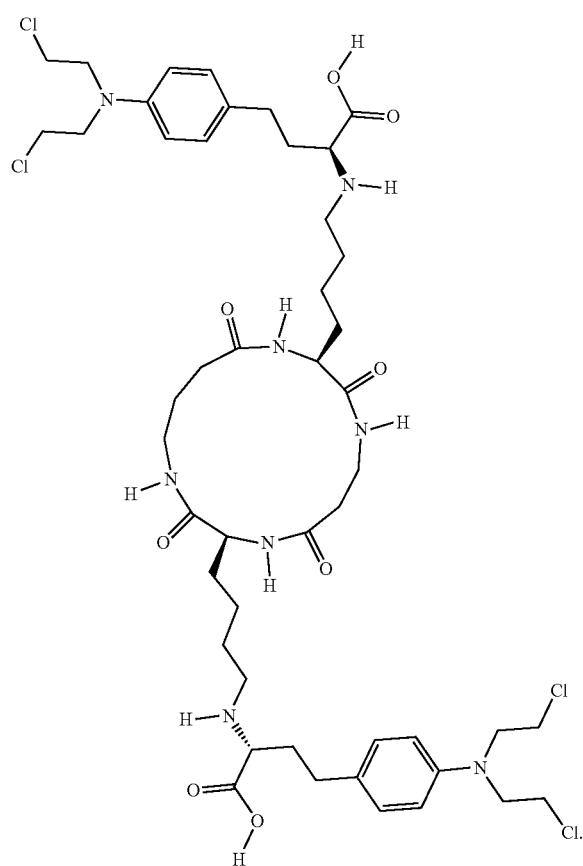 [SMILES: O=C1CCCNC(=O)[C@H](CCCCN[C@H](CCc2ccc(N(CCCl)CCCl)cc2)C(=O)O)NC(=O)CCNC(=O)[C@H](CCCCN[C@@H](CCc2ccc(N(CCCl)CCCl)cc2)C(=O)O)N1]

[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate, 2-(2,5-Dioxopyrrol-1-yl)ethyl 4-[4-[bis(2-chloroethyl)amino]phenyl]butanoate,

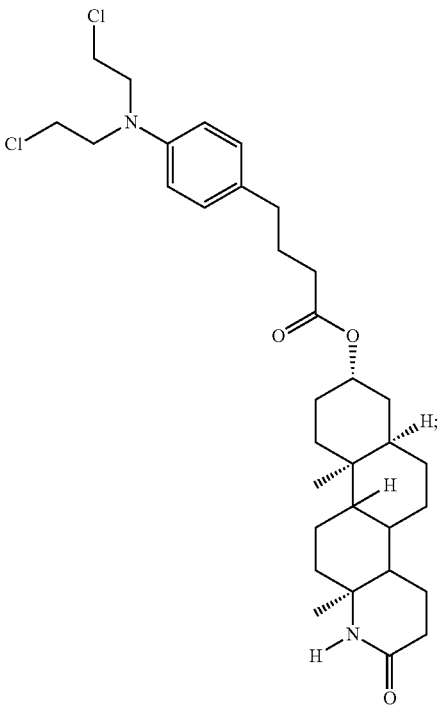

In another embodiment, the present invention includes a method of rescuing learning and/or memory deficits caused by Alzheimer's disease, comprising: (a) administering to a subject suffering from the learning and/or memory deficits caused by the Alzheimer's disease a compound selected from:

[(1,4-Dihydroxy-9,10-dioxoanthracen-2-yl)-phenylmethyl] 4-[4-[bis(2-chloroethyl)amino]phenyl]butanoate,

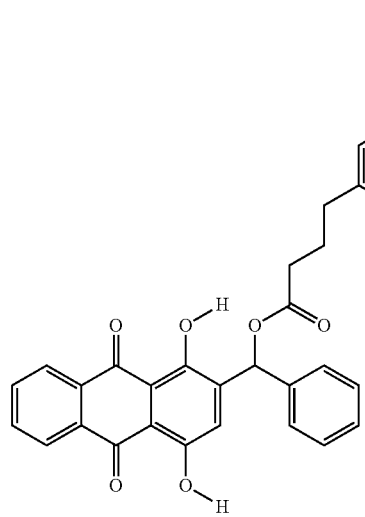

4-Chloro-3-fluoro-N-[(1R)-2-methyl-1-(2-methyl-1,2,4-triazol-3-yl)propyl]benzamide,

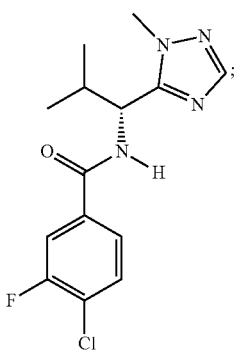

or (2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

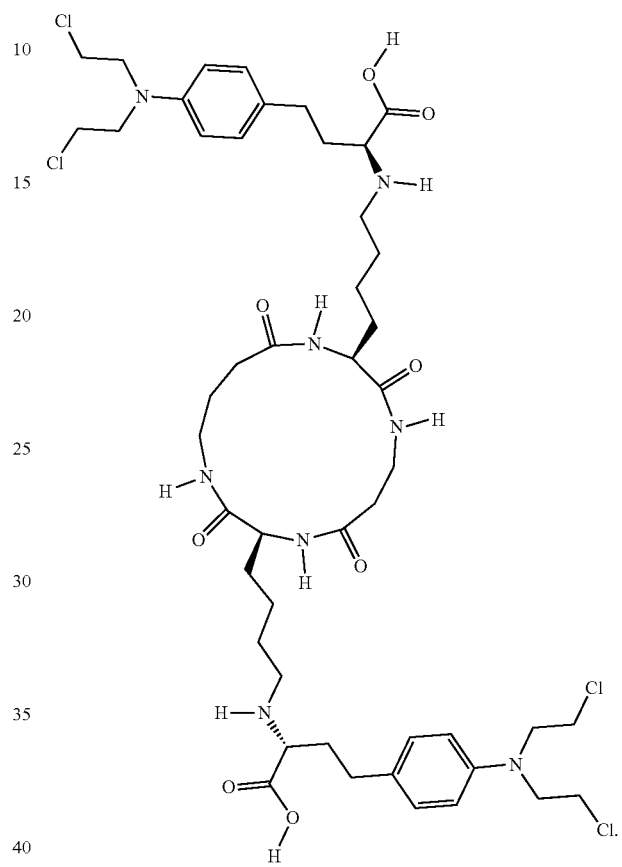

in an effective amount to rescue the learning and/or memory deficits caused by the Alzheimer's disease in the subject; and (b) testing the subject for learning and/or memory performance. In one aspect, the compound is formulated in a pharmaceutical composition. In another aspect, the compound is formulated with a pharmaceutically acceptable carrier, diluent, or excipient. In another aspect, the compound is formulated for oral, enteral, parenteral, pulmonary, or intravenous administration. In another aspect, effective amount is between about 1, 2, 3, 4, 5, 6, 7, 8, 9, 10, 11, 12, 13, 14, 15, 16, 17, 18, 19 or 20 mg kg body weight, 3 times per week. In another aspect, the ligand is provided between about 1-20 mg kg body weight, 1-7 times per week, 5-15 mg kg body weight, 2-6 times per week, or 8-12 mg kg body weight, 3-5 times per week, or 10 mg kg body weight, 3 times per week.

BRIEF DESCRIPTION OF THE DRAWINGS

For a more complete understanding of the features and advantages of the present invention, reference is now made to the detailed description of the invention along with the accompanying figures and in which:

(FIG. 1A) CASTp calculations of BACE1 domain1 interaction with selected pharmacophore residues involvement and positioned were highlighted with ball and stick models ASP 32, THR33 and SER 35. The two core binding pockets of BACE1 domain1 region i.e. starting from 1 to 146 residues were read and highlighted of catalytic core trait pockets domain 1 covered the catalytic residues pockets 29, 31 were highlighted with light and dark shading ball and stick models. (FIG. 1B) Two-dimensional pharmacophore model of BACE1 with pepstatin was generated by LigandScout from the complex structure of BACE1 and pepstatin The dotted arrows indicated the hydrogen bond donor (HBD) and hydrogen bond acceptors (HBA) features with residues, THR 33A posing that two HBD (dotted to Thr33A) and one hydrogen bond acceptor ASP 33A HBA (dotted Asp32A and Ser35A) with pharmacophore pepstatin ligand and the yellow sphere represented the (HF) represented the hydrophobic feature in the ligand based pharmacophore. (FIG. 1C) The 1D colored spheres pharmacophore models of BACE1 schematic images indicating the nature of HBD middle shading, HBA upper shading, hydrophobic features (HF) right shading and darker spheres represent excluded volumes (EV). (FIG. 1D) The BACE1 with pepstatin (ligand) complex model with extended wire protein ligand stick model with pharmacophore properties like HBA, HBD, and HF and excluded volumes.

(FIG. 2A) Peptide cleavage mechanism by aspartyl proteases, (upper shading) circle is ligand interaction group and (dark bonds) circle is amino acid aspartyl protease (Asp) interaction group participated in catalytic cleavage process. (FIG. 2B) Aspartyl protease inhibitor pepstatin (CID 5478883) used as template ligand and computational screening finalize 5 best ligands representing the same characteristic features of pepstastin ligand and ligand 1 finally tested in in vitro cell culture studies.

FIGS. 3A to 3C show: (FIG. 3A) The predicted docking structures of lead molecules with the target protein based on lamarkin geometric algorithm and PyRx analyses: the five best leads, which include (Ligand 1) CID 1008594, (Ligand 2) CID 10048142, (Ligand 3) CID 10054794, (Ligand 4) CID 100031313 and (Ligand 5) CID 10034005. Crystal structure of BACE1 superposed on the docking predictions of top ranking ligands models (1-5). (FIG. 3B) These 5 ligand leads H-bond interactions displayed in dashed lines and ligand molecules in light color stick models dark color resides with labels. (FIG. 3C) Finally based upon the molecular docking, drug-likeness and ADMET predictions only three ligands models i.e., 1, 3 and 5 considered and one ligand 1 highlighted in (right box) selected for in vitro cell culture studies.

FIGS. 4A to 4D show BACE1 activity and Amyloid beta 40, 42 levels: (FIG. 4A and FIG. 4B) Using Sandwich ELISA, BACE1 activity levels were measured in mAPP cells, mAPP treated with ligand 1, significantly lower levels of BACE1 activity with (P=0.001). (FIG. 4C) Represents the levels of soluble Aβ40 decreased in the ligand 1-treated mAPP N2a cells significantly lower in mAPP cells (P=0.01) compared to untreated mAPP cells. (FIG. 4D) mAPP treated N2a cells with ligand 1, significantly lower levels of Aβ42 (P=0.005) compared to untreated mAPP cells.

(FIG. 7A) Shows mouse neuroblastoma (N2a) cells were transfected with mutant APP cDNA and ligand 1+mAPP treated cells immunoblotting analysis was conducted using protein lysates from transfected with mAPP 1). N2a cells, 2). N2a+Ligand 3). mAPP 4). Ligand1+N2a cells with mutant AβPP cDNA. (FIG. 7B) shows quantitative densitometry analysis of mitochondrial dynamics proteins Drp1 (P=0.01) and Fis1 (P=0.001) were significantly decreased; and the fusion proteins Mfn1 (P=0.002), Mfn2 (P=0.02), and Opa1 (P=0.01) were significantly increased in ligand1 treated mAPP cells relative to mAPP cells, indicating the presence of ligand 1 protective mitochondrial dynamics in mAPP cells. Shows quantitative densitometry analysis of mitochondrial biogenesis proteins biogenesis proteins PGC1α (P=0.01), Nrf1 (P=0.004), Nrf2 (P=0.004) and TFAM (P=0.001) were significantly increased in ligand1 treated mAPP cells relative to mAPP cells, indicating that ligand 1 enhances mitochondrial biogenesis in mAPP cells. (c) shows quantitative densitometry analysis of synaptic proteins Synaptophysin (P=0.02), PSD95 (P=0.02), and MAP2 (P=0.04) were significantly increased in ligand1 treated mAPP cells relative to mAPP cells, indicating the presence of ligand 1 protective neuronal protection in mAPP cells.

(FIG. 8A). Immunofluorescence analysis of BACE1, 6E10, and C-terminal fragment (CTF) from transfected with mAPP cells 1). N2a cells, 2). N2a+ Ligand 1, 3). mAPP and 4). mAPP+ligand 1 N2a cells. Immunoreactivity levels of BACE1, 6E10, and C-terminal fragment (CTF) were significantly lower in the ligand 1-treated mAPP N2a cells relative to the untreated mAPP N2a cells, BACE1 (P=0.01), 6E10 (P=0.01), C-terminal fragment (P=0.01) indicating that ligand 1 reduces mutant APP and soluble/insoluble Aβ in mAPP N2a cell cultures. (FIG. 8B). Electron microscopy of N2a cells showing the mitochondrial number, length and architectures within the cell in all 4 groups i.e. 1). N2a cells, 2). N2a+Ligand 1, 3). mAPP and 4). mAPP+ligand 1 N2a cells. with mutant AβPP cDNA. Mitochondrial morphology significantly changed—number and length in ligand 1 treated cells when compared to other groups.

DETAILED DESCRIPTION OF THE INVENTION

Figure 1A:
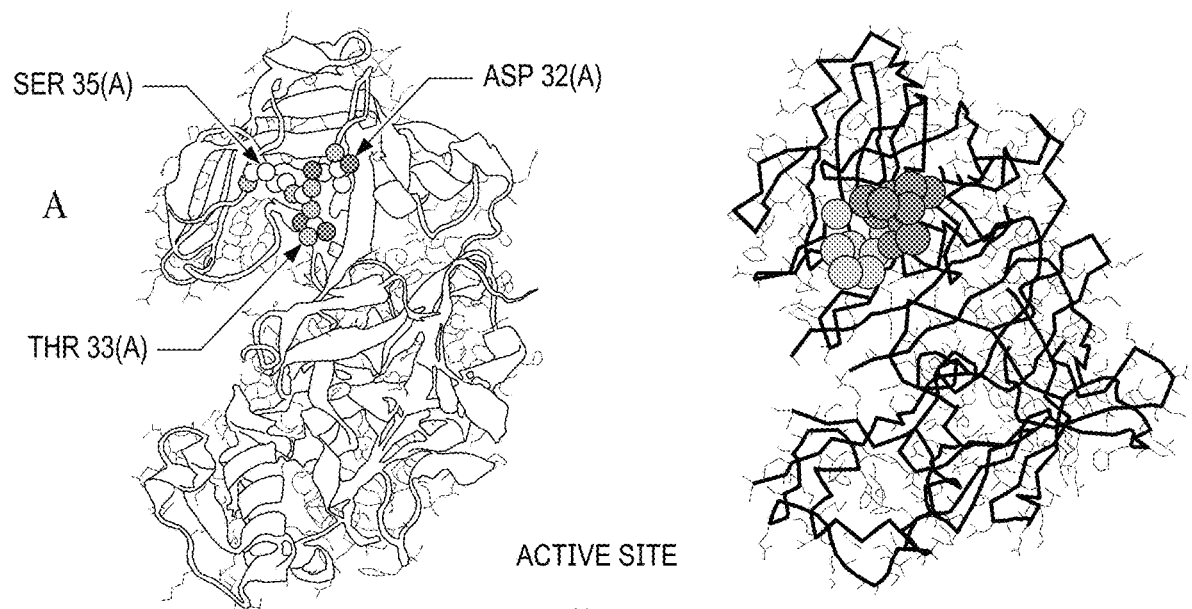
FIGS. 1A to 1D show.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The disclosed method and compositions work to create a more effective BACE 1 inhibitor. The disclosed method employs the use of therapeutic ligands that bind to the catalytic core domain active site found on BACE 1 in order to inhibit its enzymatic function in abnormal APP processing and reduce Aβ levels in AD afflicted brain neurons.

Currently, BACE1 inhibitors have continuously failed at clinical trials. The approach herein is different because the inventors used pharmacophore-based ligand(s) with supramolecular properties that directly binds to specific biological targets of BACE1. In the present invention, the inventors selected a template ligand (pepstatin) as well known "aspartic protease inhibitor" that was selected as a template ligand with same functional groups to target BACE1. The ligands selected bind at the 'Asp 32' residue, which is key catalytic trait, appeared in BACE1 domain. One or more of the ligands identified were studied in silico, in vitro, in cellulo and in vivo, and showed reduced BACE1 activity, reduced Aβ40 and 42 levels and enhanced mitochondrial biogenesis and synaptic activities. This targeted approach is can be tested at different stages of disease progression in APP, transgenic mice and in vivo validations provide new insights for BACE1 in AD pathogenesis. As used herein, Human BACE1 is HGNC: 933; Entrez Gene: 23621; Ensembl: ENSG00000186318; OMIM: 604252; and UniProtKB: P56817.

Several animal models, including mouse models of APP used to screen for inhibition of beta-secretase activity in vivo following compound treatment. Animals used in this invention can be wild type, transgenic, or gene knockout animals. For example, the APP mouse model, prepared as described in Games et al., Nature 373, 523-527 (1995), relevant portions incorporated herein by reference, and other non-transgenic or gene knockout animals are useful to analyze in vivo inhibition of Aβ and sAPPβ production in the presence of, e.g., inhibitory compound ligand 1. Generally, 2-month-old APP mice, gene knockout mice or non-transgenic animals are administered compound formulated in vehicles via subcutaneous, intra-venous or other route of administration (intra-peritoneal). For dose 5 mg/kg oral dose of the compound to young female APP mice, Aβ40 and 42 peptide levels are reduced approximately in brain hippocampus and brain cortex, compared to vehicle-treated mice. Twice a week following two weeks the administration of compound, animals are sacrificed, and brains are removed for analysis of Aβ species with C-terminus products like c-99 and c-83 validate with ligand 1 treated AD treated postmortem brain samples. This detects the majority of Aβ species inhibition in presence of ligand 1. Animals (APP transgenic or non-transgenic mice) administered an inhibitory compound may demonstrate the reduction of Aβ in brain tissues, as compared with vehicle-treated controls. Both Aβ 40 and 42 levels can be measured, as well as mRNA and protein levels in, e.g., the ligand 1-treated and untreated APP mice. As taught hereinbelow, one or more of the following methods can be used to characterize the brain tissues: (1) qRT-PCR, (2) immunoblotting, (3) Co-IP and immunofluorescence, Golgi-cox staining and (4) transmission electron microscopy.

These results show that pharmacophore-based ligand(s) reduce Aβ toxicity and ameliorating cognitive decline in Alzheimer's disease.

Five BACE1 ligands are:

Ligand 1—[(6As,8S,10aS,12aS)-10a, 12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate, CID 10008594-C33H48C12N2O3, or any one of the 23 related compounds in PubChem

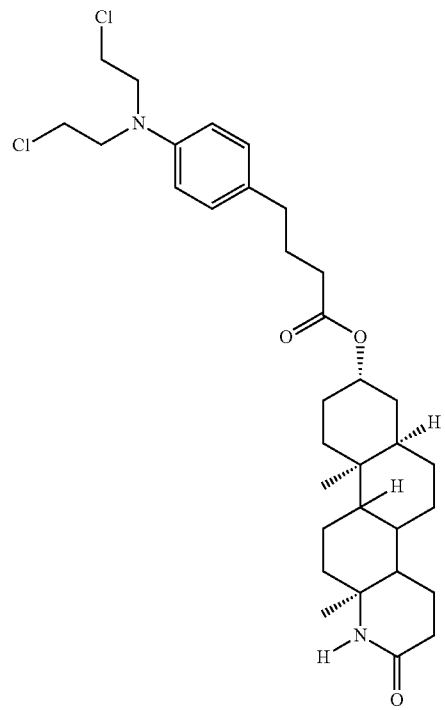

Ligand 2—2-(2,5-Dioxopyrrol-1-yl)ethyl 4-[4-[bis(2-chloroethyl)amino]phenyl]butanoate, CID 10048142—C20H24C12N2O4, or any one of the 7 related compounds in PubChem,

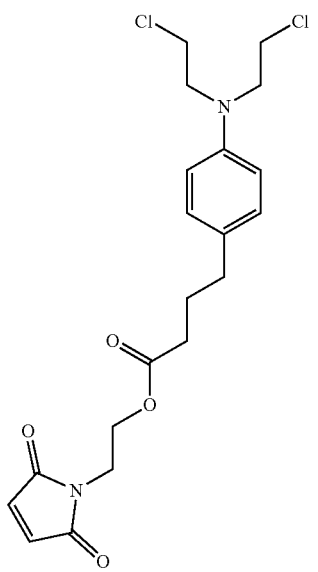 [SMILES: O=C(CCCc1ccc(N(CCCl)CCCl)cc1)OCCN1C(=O)C=CC1=O]

Ligand 3 '[(1,4-Dihydroxy-9,10-dioxoanthracen-2-yl)-phenylmethyl] 4-[4-[bis(2-chloroethyl)amino]phenyl]butanoate, CID 10054794—C35H31C12NO6, or any one of the 21 related compounds in PubChem,

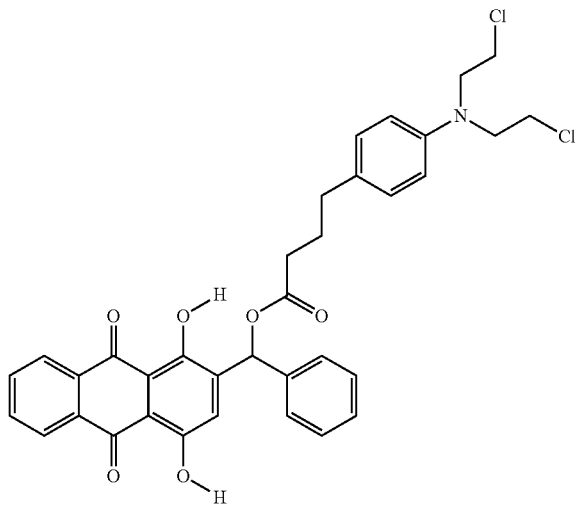 [SMILES: O=C(CCCc1ccc(N(CCCl)CCCl)cc1)OC(c1ccccc1)c1cc(O)c2c(c1O)C(=O)c1ccccc1C2=O]

Ligand 4—4-Chloro-3-fluoro-N-[(1R)-2-methyl-1-(2-methyl-1,2,4-triazol-3-yl)propyl]benzamide, CID 100031313—C14H16ClFN4O, or any one of the structurally related compounds in PubChem,

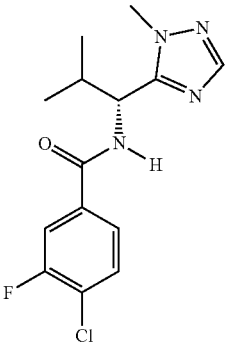 [SMILES: CC(C)[C@@H](NC(=O)c1ccc(Cl)c(F)c1)c1ncnn1C]

Ligand 5 (2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid, CID 10034005—C25H27NO, or any one of the 13 related compounds in PubChem,

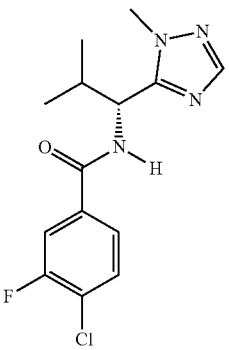 [SMILES: CC(C)[C@@H](NC(=O)c1ccc(Cl)c(F)c1)c1ncnn1C]

Of these five ligands, BACE 1 treated with Ligand 1 was found to be the most effective at: [1] reducing levels of BACE1 activity; [2] reducing the amount of Aβ peptides; [3] increasing levels of mitochondrial fusion; [4] reducing mitochondrial dysfunction; and [5] increasing biogenesis and synaptic proteins. Unlike current BACE 1 inhibitors, the disclosed method utilizes pharmacophore-based ligands with supramolecular properties that allow them to directly bind to the specific biological targets of BACE 1, allowing for increased effectiveness. It was found that these molecules were effective at inhibiting BACE 1 and reducing Aβ peptides than current methods. Importantly, they effectively cross the blood brain barrier, and have no known side effects.

The present inventors identified novel BACE1 inhibitor ligands, and studied the features of ligand in AD neurons with drug discovery approach. In silico analysis was used to identify the best ligand small molecules, namely, those that exhibited the best docking scores and best interacting sites of BACE1 inhibition. Furthermore, the protective effects of ligand 1 against BACE1 and Aβ-induced mitochondrial and synaptic properties in N2a cells were tested. Finally, the inventors determined: (1) cell viability, (2) the inhibition of Aβ40 and 42 levels, (3) mRNA and protein levels of mitochondrial dynamics & biogenesis and synaptic genes, (4) immunohistochemistry, and (5) mitochondrial number and morphology in AD neurons treated and untreated.

Active site CASTp analysis. Prediction of all possible binding sites of the protein BACE1 was analyzed through the CASTp results explore nearly 47 binding pockets with unique area and volumes. The binding pockets 1 with 337.5 area and 424.9 vol closed to conserved catalytic residues of domain 1 of BACE1 (FIG. 1A). The active site of BACE1 contain the catalytic residues as ASP 32, THR 33 and SER 35 located at ectodomain 1 pocket (FIG. 1A) and these active site selected for pharmacophore and molecular docking studies.

Ligands screening. APP processing involves two successive catalytic cleavages to release sAPPβ and Aβ. Hence, the inventors chose pepstatin, a well-known aspartyl protease inhibitor as the reference ligand for screening the similar structures from chemical libraries. The noncommercial chemical library PubChem contains huge ligands around 93 lakhs including, tested and non-tested, overall 15,130 clusters of structurally similar compounds of Pepstatin screened with 80% cutoff among the compounds. Furthermore, in silico screening and validation were performed based upon the structural similarity of pepstatin ligands downloaded, and results were saved in ligand chemical format (.sdf). From the PubChem library screening, only 873 structure were considered related to lead molecules set for the further pharmacophore validations.

Figure 1B:
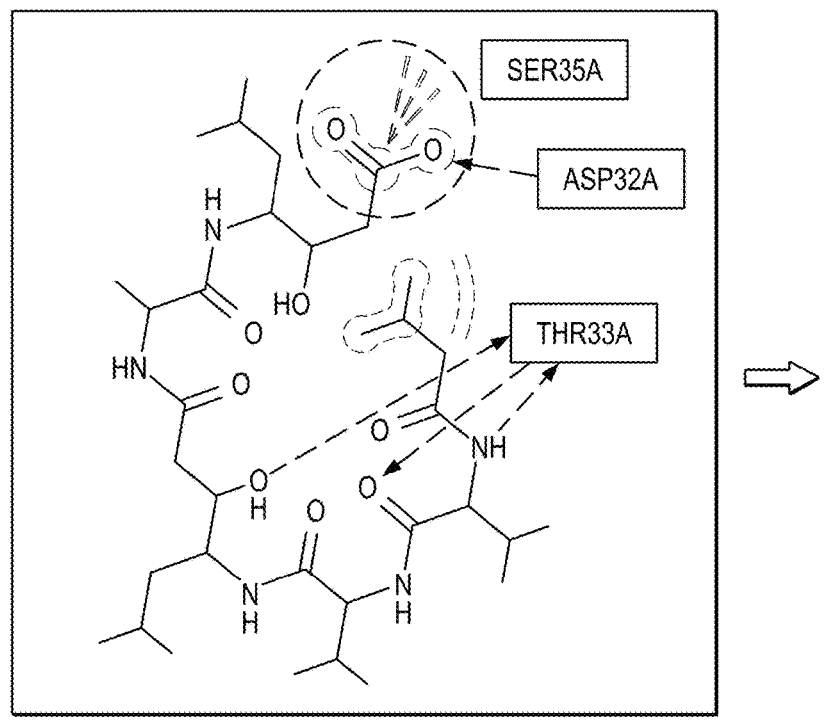
Figure 1C:
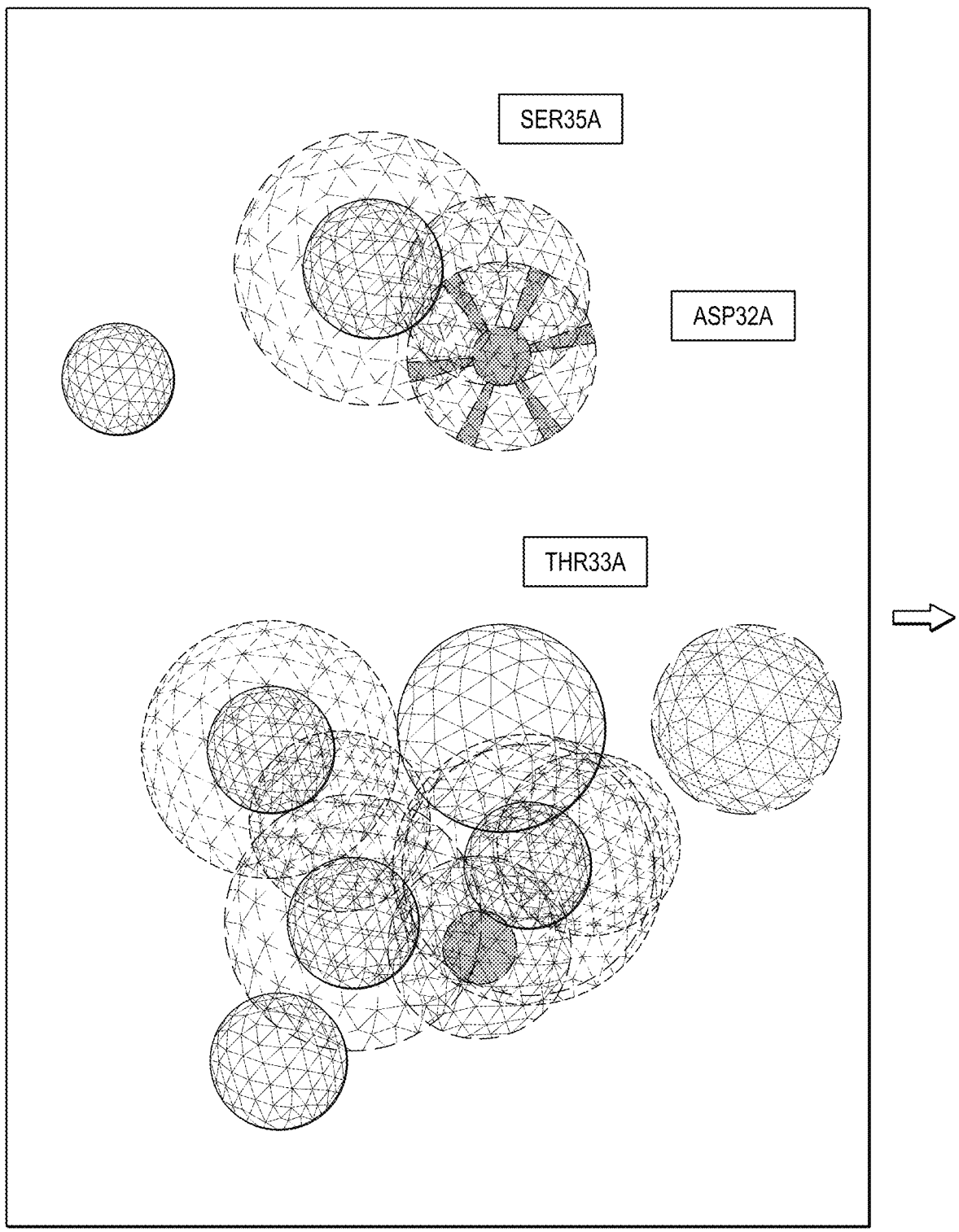
Figure 1D:
Figure 2A:
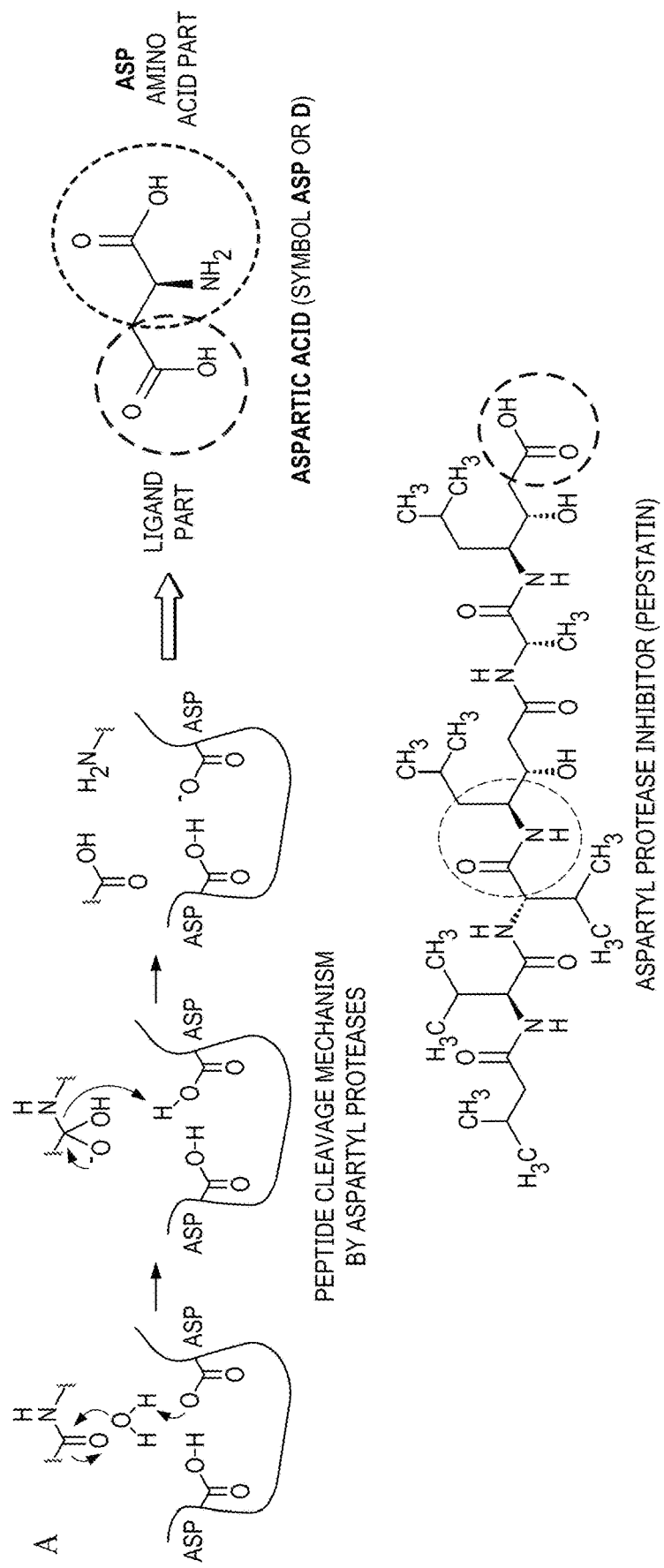
FIGS. 2A and 2B show.
Figure 2B:
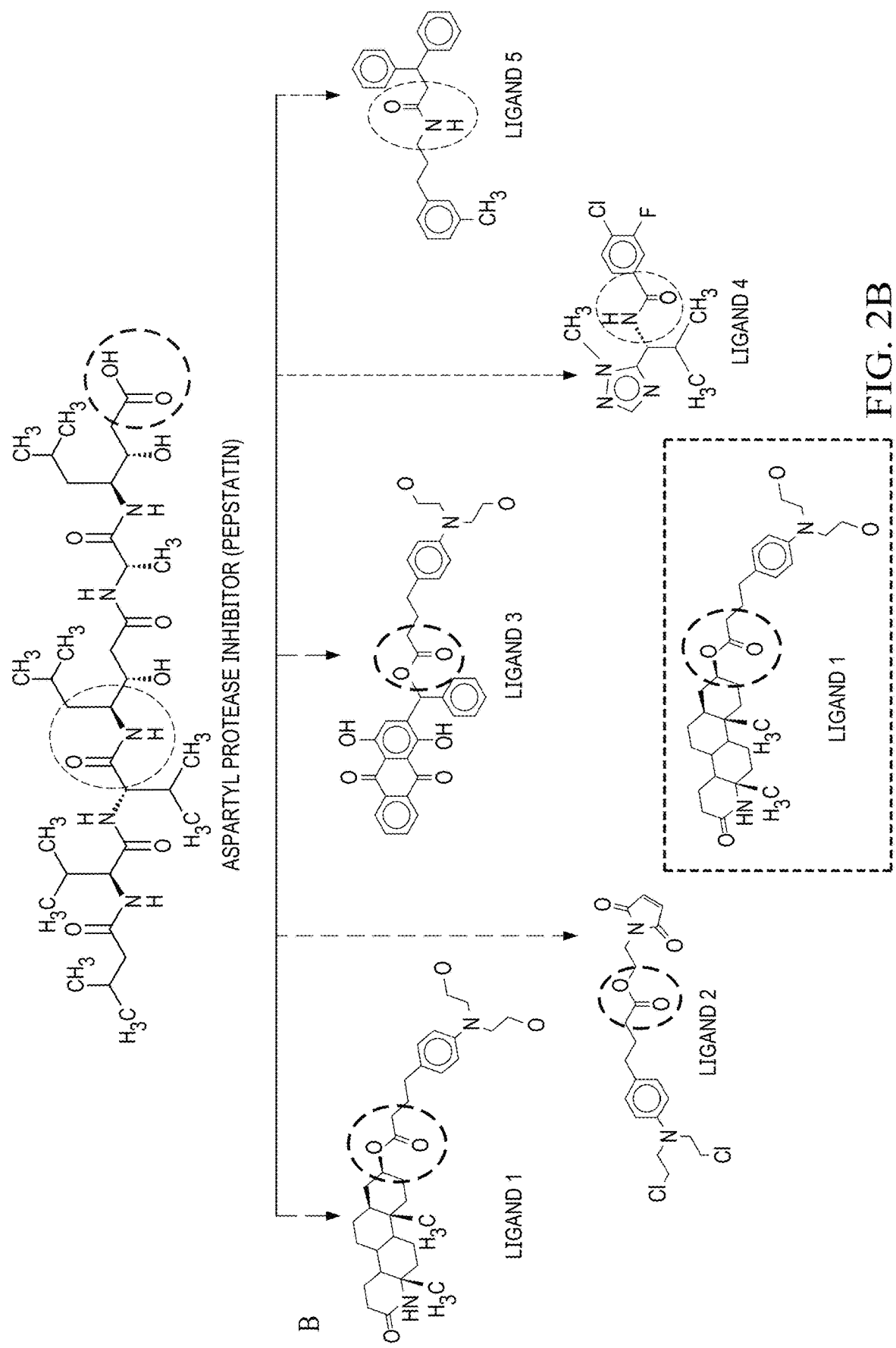

Pharmacophore validated ligands. Hexa-peptide containing the unusual amino acid statine Sta, (3S,4S)-4-amino-3-hydroxy-6-methylheptanoic acid) Pepstatin used as a referenced ligand is a well-known aspartyl protease inhibitor. The molecular mechanism and catalytic cleavage with aspartic acid (D) functional group participations is visualized in (FIG. 2A). The selected group of ligand chemical structure features and associations is depicted in (FIG. 2B). In pharmacophore screening, BACE1 protein model was mechanically generated by the LS program, and includes four features: 1 hydrogen bond donor (HBD), 2 hydrogen bond acceptors (HBA) and 1 hydrophobic group (FIG. 1C). The program mechanically generated many excluded volumes within the model. The HBD features pharmacophore point toward 1-proton donor group at ASP32 and 2-proton acceptors of the ligand from the THR33, respectively (FIG. 1B). Within the test database, the inventors kept the ligand, pepstatin, present in complex structures (FIG. 1D). The pepstatin-BACE1 complex will display the binding regions of ligand part with BACE1 (FIG. 1D). First, the pepstatin was extracted and then, hydrogen atoms were additional and energy minimized by the LigandScout. The minimized structure of pepstatin ligand added to the test database. When screening, the test compounds were properly mapped within the pepstatin pharmacophore models as shown in (FIGS. 1A-1D). The result verified and validated the pharmacophore screening library of Pepstatin from PubChem 873 molecules. A small number of ligand molecules fitted within the designed BACE1 pharmacophore around 16 molecules with CID Numbers: 1008594, 10031313, 10034005, 10048142, 10054794, 10079786, 99647460, 98053228, 99647463, 91742649, 90468180, 90013848, 88791717, 87900731, 87794123, and 87464897, observed to be the best-fitted ligands. Based on BACE1 pharmacophore analysis these ligands used for further validation with molecular docking studies.

Figure 3A:
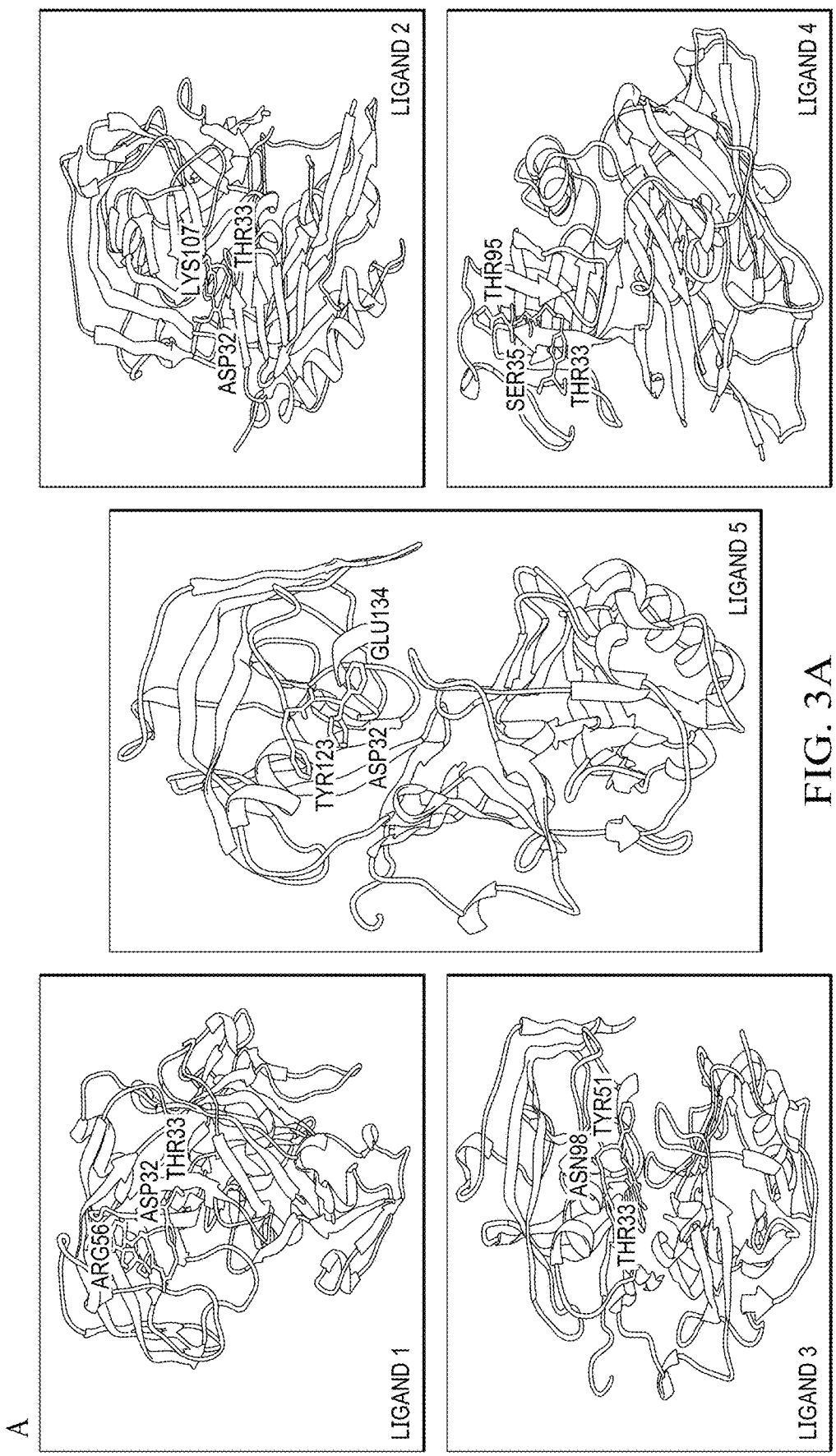
Figure 3B:
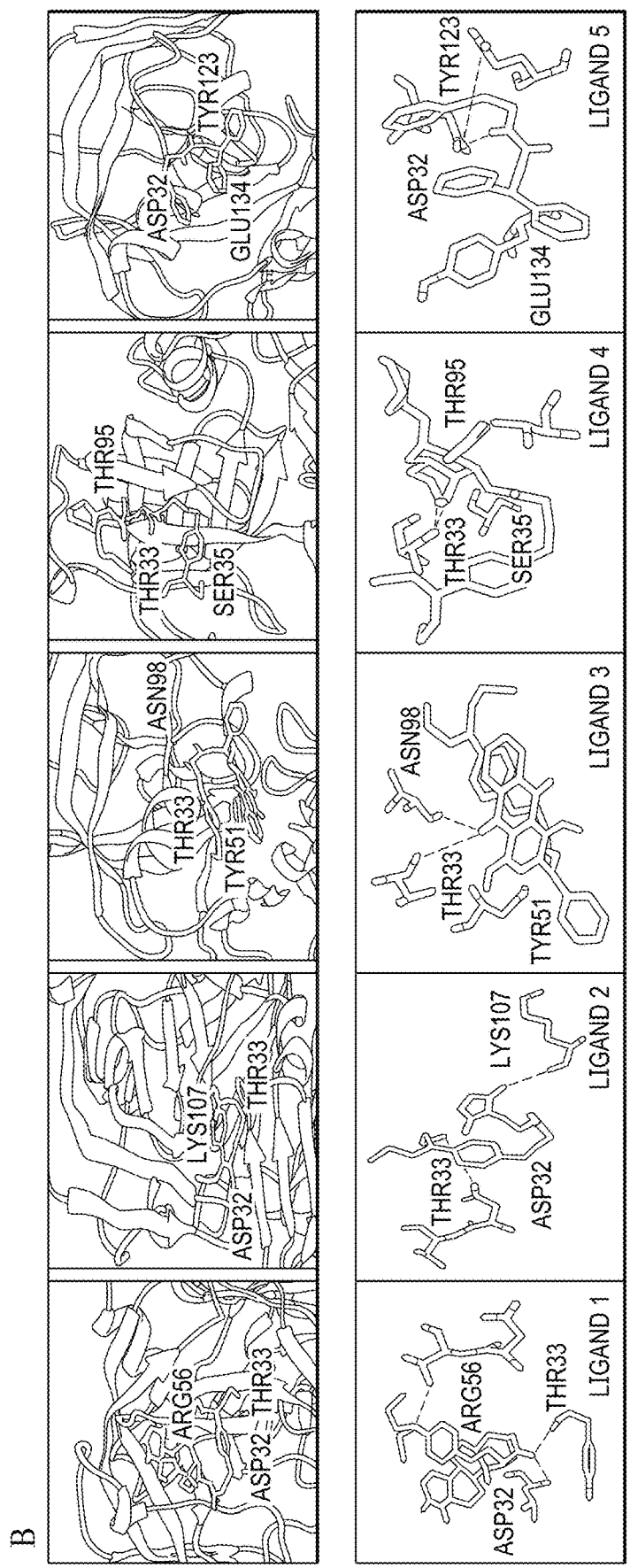

Molecular Docking. Docking studies were carried out with the 16 best pharmacophore ligands by running the AutoDock 4.2v (45) PyRx virtual screening tool setup with the docking files (46). The 16 compounds considered for the molecular docking studies based on best-fitted pharmacophore fitness. After molecular docking results, only the top 5 leads from the molecular docking results (ranked by docking score) were visually scrutinized. The best 5 compounds, which showed good possession of the predicted binding pocket, having at least (minimum) two hydrogen bonds within the protein, were selected, and shown as a docking model (FIG. 3A). The top-ranking molecules docking scores with respective CIDs are 1008594, CID 10048142, CID 10054794, CID 10031313, and CID 10034005. These ligands further analyzed for molecular interaction such as hydrogen bonding, residue interactions with respective ligand and protein visualized with the PyMoL visualization tool as illustrated in (FIG. 3B). The inventors focused on each ligand and their molecular interactions with BACE1 chief residues of the protein. The best ligand molecules selected through molecular docking scores. Top five ligands mostly binds with the active site of the BACE1 and inhibits its catalytic function. These ligands considered as drugs to target AD by inhibiting the BACE1 enzymatic catalytic function in APP processing. The computational validations like molecular docking, ADMET, drug-likeness properties indicate that ligand 1 showed good lead properties from the top 3 qualified ligands, further, biological validations proceed to test the ligands in mouse neuronal cell (N2a) cultures in in vitro studies (FIG. 3C).

Figure 4C:
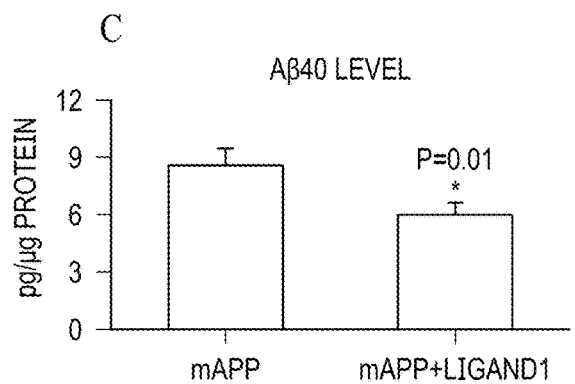
Figure 4D:
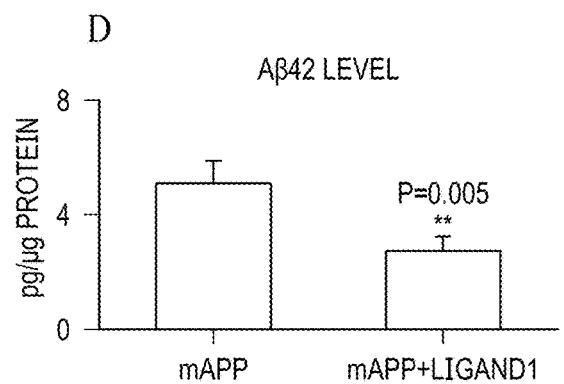

ELISA Ligand based inhibition of BACE1 activity, Aβ 40 and 42. BACE1 activity, Levels of Aβ40 and 42. To determine whether ligand 1 lowers BACE1 activity and reducing the Aβ40 and Aβ42 levels, the inventors measured BACE1 activity, Aβ40 and Aβ42 levels in mutant APP cells (N2a+ mutant cDNA transfected) treated with ligand 1 using Sandwich ELISA. As shown in (FIGS. 4A & 4B), significantly reduced BACE1 activity found in the mAPP cells treated with ligand 1 (P=0.001) relative to mutAPP cells. The levels of Aβ40 (P=0.01) and Aβ42 (P=0.005) were found to be reduced in the mAβPP cells treated with ligand 1 compared to mAPP cells (FIGS. 4C & 4D). It is interesting to note that BACE1 activity, Aβ42 levels were significantly reduced in the mAPP cells when treated with ligand 1. Overall, these observations revealed that treatment of ligand 1 is effectively inhibits BACE1 activity and reduced both Aβ40 and Aβ42.

Cell survival and apoptotic cell death. To determine the effect of ligand 1 treatment of N2a cells, the inventors assessed cell viability. As shown in (FIG. 5), significantly increased levels of cell viability were found in ligand treated cells (P=0.038) relative to untreated cells. Cell viability was not significantly increased in cells treated with mAPP+ ligand 1 (P=0.181) compared mAPP cells. Significantly increased cell viability levels were found in cells treated with ligand 1 with N2a cells (P=0.038) relative to mAPP cells, suggesting that ligand 1 increases cell viability in the presence of Aβ.

mRNA levels of mitochondrial dynamics and mitochondrial biogenesis and synaptic genes. The inventors determined the effects of Aβ on mitochondrial structural genes and the BACE1, APP inhibition and protective effects of ligand 1 on mRNA expression of the mitochondrial dynamics genes Drp1 and Fis1 (fission); Mfn1, Mfn2, Opa1 (fusion); mitochondrial biogenesis genes PGC1α, Nrf1, Nrf2, and Tfam; synaptic & dendritic genes Syn, PSD 95; APP-related genes like APP-human, BACE1 and presenilin 1; and housekeeping genes B-actin, GAPDH (Table 1). The inventors analyzed the data two ways: 1) to determine the effect of Aβ, and ligand 1 (Table 2) in N2a cells, and 2) to determine the preventive effects of ligand 1, if any, in the presence of mAPP (Table 3).

TABLE 1

Summary of qRT-PCR oligonucleotide primers used in measuring mRNA expression of mitochondrial dynamics, mitochondrial biogenesis, synaptic and APP-related genes in untreated-N2a, cDNA mAPP-N2a, ligand1-N2a and cDNA mAPP + ligand1 cells.

| Gene | DNA Sequence (5'-3') | PCR Product Size | SEQ ID NO: |
|---|---|---|---|
| Mitochondrial Dynamics Genes | | | |
| Drp1 | Forward Primer ATGCCAGCAAGTCCACAGAA | 86 | 1 |
| | Reverse Primer TGTTCTCGGGCAGACAGTTT | | 2 |
| Fis1 | Forward Primer CAAAGAGGAACAGCGGGACT | 95 | 3 |
| | Reverse Primer ACAGCCCTCGCACATACTTT | | 4 |
| Mfn1 | Forward Primer GCAGACAGCACATGGAGAGA | 83 | 5 |
| | Reverse Primer GATCCGATTCCGAGCTTCCG | | 6 |
| Mfn2 | Forward Primer TGCACCGCCATATAGAGGAAG | 78 | 7 |
| | Reverse Primer TCTGCAGTGAACTGGCAATG | | 8 |
| Opa1 | Forward Primer ACCTTGCCAGTTTAGCTCCC | 82 | 9 |
| | Reverse Primer TTGGGACCTGCAGTGAAGAA | | 10 |
| Mitochondrial Biogenesis genes | | | |
| PGC1α | Forward Primer GCAGTCGCAACATGCTCAAG | 83 | 11 |
| | Reverse Primer GGGAACCCTTGGGGTCATTT | | 12 |
| Nrf1 | Forward Primer AGAAACGGAAACGGCCTCAT | 96 | 13 |
| | Reverse Primer CATCCAACGTGGCTCTGAGT | | 14 |
| Nrf2 | Forward Primer ATGGAGCAAGTTTGGCAGGA | 96 | 15 |
| | Reverse Primer GCTGGGAACAGCGGTAGTAT | | 16 |
| TFAM | Forward Primer TCCACAGAACAGCTACCCAA | 84 | 17 |
| | Reverse Primer CCACAGGGCTGCAATTTTCC | | 18 |
| Synaptic genes | | | |
| Synaptophysin | Forward Primer CTGCGTTAAAGGGGGCACTA | 81 | 19 |
| | Reverse Primer ACAGCCACGGTGACAAAGAA | | 20 |
| PSD95 | Forward Primer CTTCATCCTTGCTGGGGGTC | 90 | 21 |
| | Reverse Primer TTGCGGAGGTCAACACCATT | | 22 |
| APP-related genes | | | |
| APP-Human | Forward Primer TGGAGGTACCCACTGATGGT | 81 | 23 |
| | Reverse Primer TGTGCATGTTCAGTCTGCCA | | 24 |
| BACE1 | Forward Primer GCGAATTGGCTTTGCTGTCA | 86 | 25 |
| | Reverse Primer TGTCTGCCGTAACAAACGGA | | 26 |
| Presenilin1 | Forward Primer AGACCTACAATGTCGCCGTG | 84 | 27 |
| | Reverse Primer AGTGGATGGCAATCATCCCG | | 28 |
| Housekeeping genes | | | |
| β-actin | Forward Primer AGAAGCTGTGCTATGTTGCTCTA | 91 | 29 |
| | Reverse Primer TCAGGCAGCTCATAGCTCTTC | | 30 |
| GAPDH | Forward Primer TTCCCGTTCAGCTCTGGG | 59 | 31 |
| | Reverse Primer CCCTGCATCCACTGGTGC | | 32 |

Comparison 1—Untreated Cells Versus Aβ, and Ligand 1 (Table 2)

TABLE 2

Fold changes of mRNA expression in mitochondrial dynamic, biogenesis, synaptic and APP related genes in N2a + Ligand1, N2a + mAPP, N2a + mAPP + ligand1 cells relative to the untreated-N2a cells.

| | | mRNA fold changes | | |
|---|---|---|---|---|
| | Genes | Ligand1 | mAPP | mAPP + Ligand1 |
| Mitochondrial structural genes | Drp1 | −1.1 | −2.3** | 1.1 |
| | Fis1 | −1.1 | 1.3 | 1.0 |
| | Mfn1 | 1.1 | −1.7* | −1.2 |
| | Mfn2 | 1.2 | −1.3 | 1.1 |
| | OPA1 | 1.4 | −1.3 | 1.1 |
| Biogenesis genes | PGC1a | 1.6* | −1.7* | 1.2 |
| | Nrf1 | 1.2 | −1.7* | 1.2 |
| | Nrf2 | 1.3 | −1.5* | 1.4 |
| | TFAM | 1.2 | −1.5* | 1.5 |
| Synaptic genes | Synaptophysin | 1.4 | −1.5* | 1.3 |
| | PSD95 | 1.2 | −1.3 | 1.3 |
| APP-related genes | APP | −1.2 | 2.1** | 1.3 |
| | BACE1 | −1.8** | 1.5* | 1.1 |
| | Presenilin1 | −1.3 | 1.3 | −1.2 |

TABLE 3

Fold changes of mRNA expression in mitochondrial dynamic, biogenesis, synaptic and APP- related genes in N2a + mAPP + ligand1 cells relative to the mAPP N2a cells.

| | | mRNA fold changes |
|---|---|---|
| | Genes | mAPP + ligand1 |
| Mitochondrial structural genes | Drp1 | −2.3** |
| | Fis1 | −1.5* |
| | Mfn1 | 1.3 |
| | Mfn2 | 1.5* |
| | OPA1 | 1.2 |
| Biogenesis genes | PGC1a | 2.0** |
| | Nrf1 | 2.1** |
| | Nrf2 | 2.1** |
| | TFAM | 1.8* |
| Synaptic genes | Synaptophysin | 1.9* |
| | PSD95 | 1.8* |
| APP-related genes | APP | −1.5* |
| | BACE1 | −1.4* |
| | Presenilin1 | −1.5* |

TABLE 4

Docking table with bonding characterization and binding energies in kcal/mol with top five therapeutic ligands involved in BACE1 inhibition.

| S. No | Ligand ID | Structures | Molecular Formula | Residues interaction | Bond length (Å) | Bonding energy (Kcal/Mol) |
|---|---|---|---|---|---|---|
| 1. | CID 1008594 | 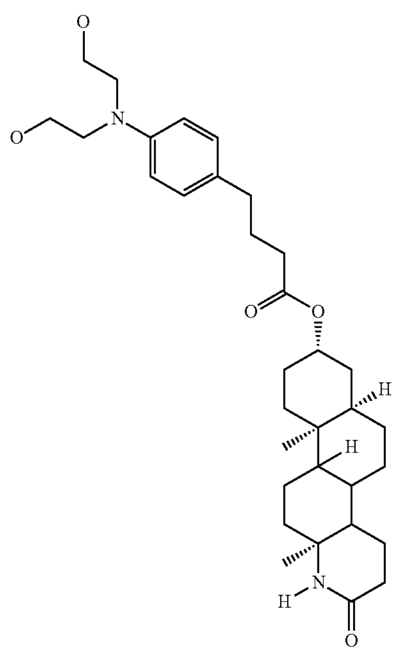 | $C_{33}H_{48}Cl_2N_2O_3$ | ASP32, ARG 56, THR 33 | (3.97), (3.13), (4.23) | −8.2 |

TABLE 4-continued

Docking table with bonding characterization and binding energies in kcal/mol with top five therapeutic ligands involved in BACE1 inhibition.

| S. No | Ligand ID | Structures | Molecular Formula | Residues interaction | Bond length (Å) | Bonding energy (Kcal/Mol) |
|---|---|---|---|---|---|---|
| 2. | CID 10048142 | 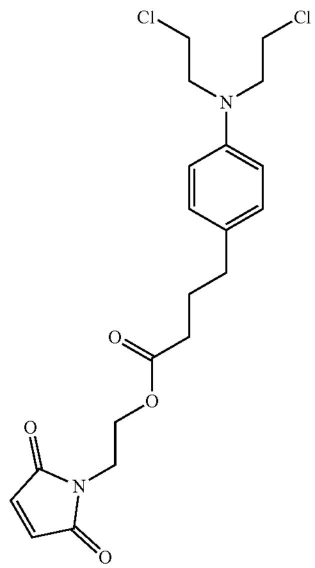 [SMILES: O=C(CCCc1ccc(N(CCCl)CCCl)cc1)OCCN1C(=O)C=CC1=O] | $C_{20}H_{24}Cl_2N_2O_4$ | ASP 32, THR 33, LYS 107 | (3.39), (3.98), (3.28) | −7.8 |
| 3. | CID 10054794 | 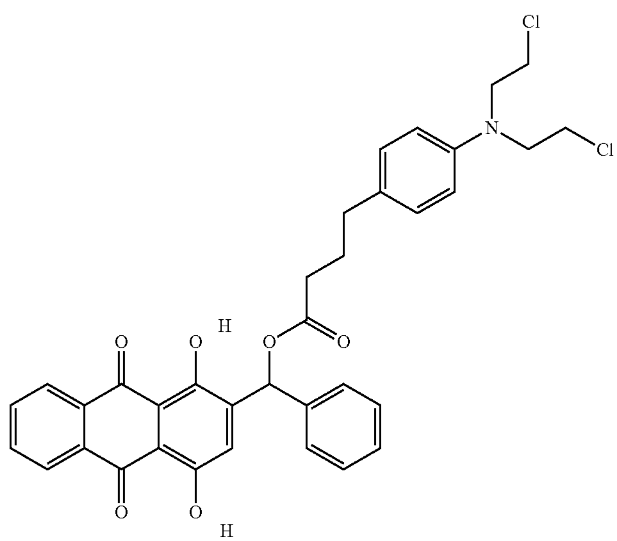 | $C_{35}H_{31}Cl_2NO_6$ | THR 33, TYR 51, THR 33 | (4.37), (3.44, 2.90), (3.04, 3.15, 3.18) | −7.4 |
| 4. | CID 100031313 | 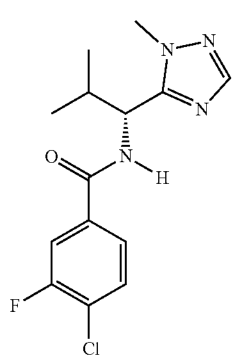 [SMILES: CC(C)[C@@H](NC(=O)c1ccc(Cl)c(F)c1)c1ncnn1C] | $C_{14}H_{16}ClFN_4O$ | THR 33, SER 35, THR 95 | (2.22), (3.03), (3.02, 3.52) | −6.9 |

TABLE 4-continued

Docking table with bonding characterization and binding energies in kcal/mol with top five therapeutic ligands involved in BACE1 inhibition.

| S. No | Ligand ID | Structures | Molecular Formula | Residues interaction | Bond length (Å) | Bonding energy (Kcal/Mol) |
|---|---|---|---|---|---|---|
| 5. | CID 100034005 | 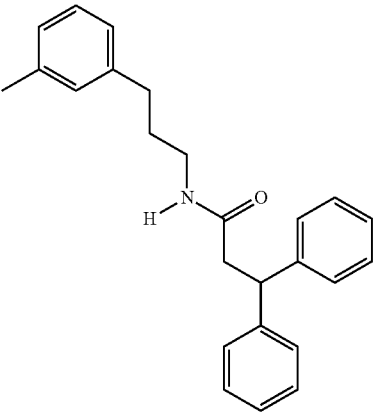 [SMILES: Cc1cccc(CCCNC(=O)CC(c2ccccc2)c2ccccc2)c1] | $C_{25}H_{27}NO$ | ASP 32, TYR 123, GLU134 | (3.42), (3.47), (3.11) | −6.8 |

TABLE 5

| S. No | Property | CID 1008594 | CID 10048142 | CID 10054794 | CID 100031313 | CID 10034005 |
|---|---|---|---|---|---|---|
| | | | a. Molsoft | | | |
| 1. | Molecular formula | $C_{33}H_{48}Cl_2N_2O_3$ | $C_{20}H_{24}Cl_2N_2O_4$ | $C_{35}H_{31}Cl_2NO_6$ | $Cl_4H_{16}ClFN_4O$ | $C_{25}H_{27}NO$ |
| 2. | Molecular weight | 442.19 | 426.11 | 631.15 | 310.10 | 357.21 |
| 3. | Number of HBA | 5 | 4 | 6 | 3 | 1 |
| 4. | Number of HBD | 1 | 0 | 2 | 1 | 1 |
| 5. | Mol LogP | 5.44 | 3.94 | 7.61 | 2.40 | 5.79 |
| 6. | Molecular polar surface area (PSA) $Å^2$ | 59.28 | 53.99 | 80.72 | 49.29 | 24.01 |
| 7. | Drug-likeness model score | 1.21 | −0.69 | 0.65 | 0.31 | 0.34 |
| | | | b. admetSAR | | | |
| 1. | Blood-Brain Barrier | BBB+ | BBB+ | BBB+ | BBB+ | BBB+ |
| 2. | Human Ether-a-go-go-Related Gene Inhibition | Weak inhibitor | Weak inhibitor | Strong inhibitor | Weak inhibitor | Weak inhibitor |
| 3. | AMES Toxicity | Non AMES toxic | Non AMES toxic | AMES toxic | Non AMES toxic | Non AMES toxic |
| 4. | Carcinogens | Non-carcinogens | Non-carcinogens | Non-carcinogens | Non-carcinogens | Non-carcinogens |
| 5. | Fish Toxicity | High FHMT | High FHMT | High FHMT | High FHMT | High FHMT |
| 6. | Acute Oral Toxicity | III | III | III | III | III |
| 7. | Aqueous solubility | −3.9083 | −3.1683 | −4.2638 | −2.6624 | −3.1052 | a. Molfoft results tabulated for top 5 BACE1 ligands molecular properties including Lipinski rule of FIVE (RO5) and Drug-likeness.
b. admetSAR toxicity results for top 5 BACE1 ligands properties including ADMET/TOX data.

Mitochondrial fission genes Drp1 (1.1 fold), Fis1 (1.1 fold) were reduced, but no statistical significance (Table 2) in ligand 1 treated N2a cells relative to untreated cells. By contrast, fusion genes Mfn1 (1.1 fold), Mfn 2 (1.2 fold) and Opa1 (1.4) were increased in ligand 1 treated cells relative to ligand 1 untreated cells (Table 2). Both mitochondrial biogenesis and synaptic genes were increased in ligand 1 treated cells relative to untreated cells, however, PGC1α mRNA levels significantly increased (1.6 fold, P<0.05). mRNA levels of BACE1 (1.2 fold), APP (1.8 fold) and PS1 (1.3 fold) were decreased in ligand 1 treated N2a cells relative to untreated cells As shown in (Table 2), mitochondrial fission genes Drp1 (2.3 fold, P<0.005) and Fis1 (1.3 fold) were increased and fusion genes Mfn1 (1.7, P<0.05), Mfn2 (1.3 fold) and Opa1 (1.3 fold) were reduced in mAPP cells relative to N2a cells.

Mitochondrial biogenesis genes PGC1α (1.7 fold, P<0.05), Nrf1 (1.7 fold, P<0.05), Nrf2 (1.5 fold P<0.05) and TFAM (1.5 fold, P<0.05) were significantly reduced in mAPP cells relative to N2a cells. These observations indicate that mutant APP reduces mitochondrial biogenesis activity. mRNA expression levels of synaptic genes synaptophysin (1.5 fold, P<0.05), and PSD95 (1.3 fold) were reduced in mAPP cells. As expected, mRNA levels of BACE1 (1.5 fold P<0.05), APP (2.1 fold, P<0.005) and PS1 (1.3 fold) were increased in mAPP cells relative to N2a cells (Table 2). Comparison 2—mAPP versus mAPP+Ligand 1 (Table 3).

The levels of mRNA expression of mitochondrial fission genes Drp1 (2.3 fold, P<0.005), Fis1 (1.5 fold, P<0.05) were significantly reduced in mAPP+ligand 1 treated cells relative to mAPP cells (Table 3). On the other hand, fusion genes Mfn1 (1.3 fold), Mfn 2 (1.5 fold P<0.05) and Opa1 (1.2 fold)

were reduced in mAPP+ligand 1 treated cells relative to mAPP cells (Table 3). These observations indicate that ligand 1 reduces mitochondrial fission activity and enhances fusion activity in ligand 1 treated mAPP cells. As shown in (Table 3), mitochondrial biogenesis, genes PGC1α (2.0 fold, P<0.005), Nrf1 (2.1 fold, P<0.005), Nrf2 (2.1 fold P<0.005) and TFAM (1.8 fold (P<0.05) were reduced in mAPP+ligand 1 treated cells relative mAPP cells. These observations indicate that ligand 1 increases mitochondrial biogenesis activity in the presence of mutant APP. In mRNA expression levels of synaptic genes synaptophysin (1.9 fold, P<0.05), and PSD95 (1.3 fold, P<0.05) were increased in mAPP+ligand 1 treated cells relative to mAPP cells. These observations indicate that ligand 1 improves the synaptic activity in mAPP cells. mRNA levels were significantly decreased for APP (1.5 fold, P<0.05), BACE1 (1.4, P<0.05), and PSN1 (1.5, P<0.05) in ligand 1 treated mAPP cells relative to mAPP cells.

Immunoblotting analysis. To determine the effects of ligand 1 on protein levels of BACE1, full length APP and Aβ, the inventors quantified proteins levels of BACE1, full length APP and Aβ in four independent treatments of cells with N2a cells, N2a+ligand 1, mAPP, and mAPP+ligand 1.

Figure 6:
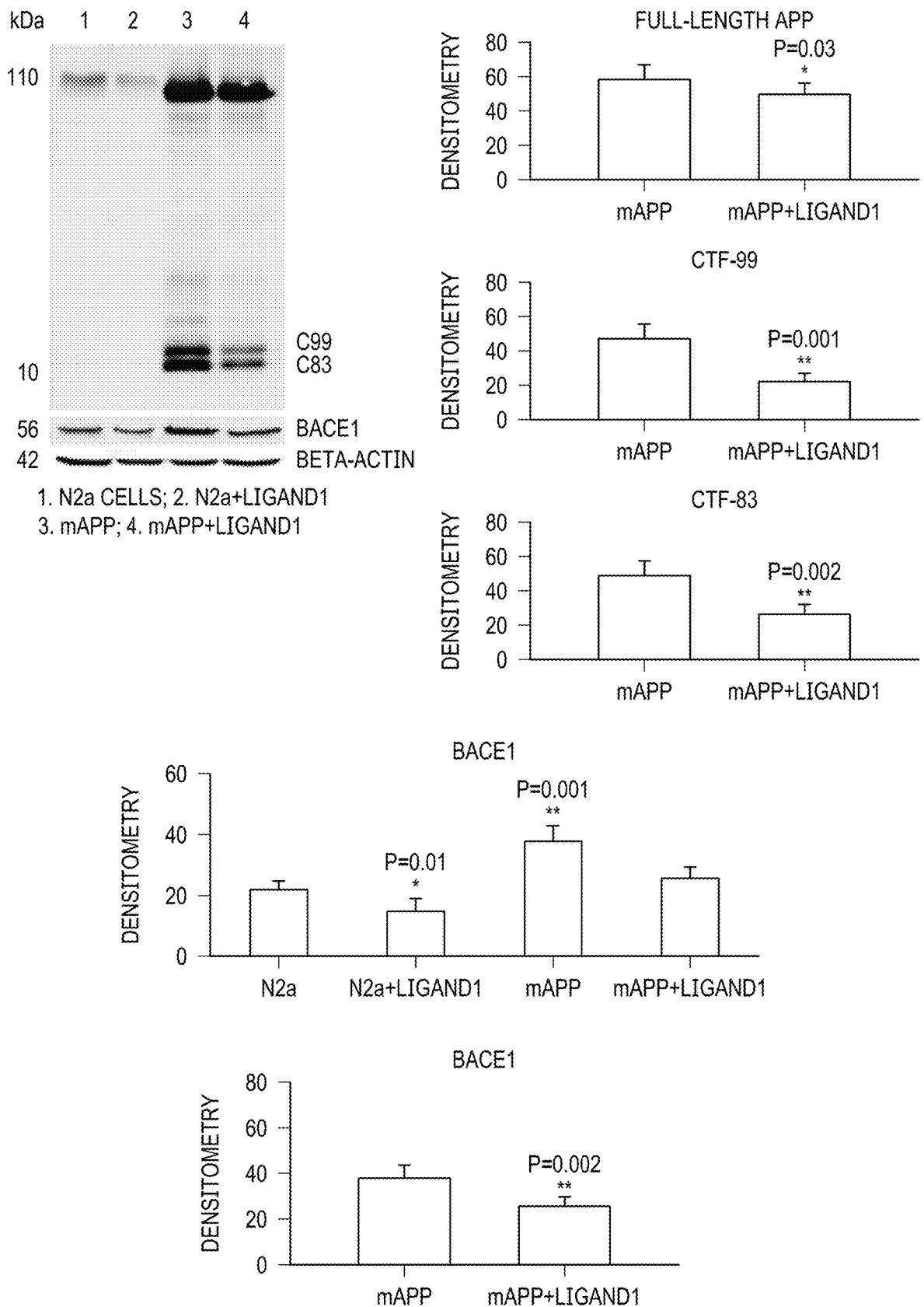
FIG. 6 shows immunoblotting analysis of full length-APP, C-terminal fragments C99 and C83 and BACE1. Mouse neuroblastoma (N2a) cells were transfected with mutant APP cDNA and immunoblotting analysis was conducted using protein lysates from transfected with mAPP 1). N2a cells, 2). N2a+ligand 1, 3). mAPP and 4). mAPP+Ligand 1 cells. A protein band of 100 kDA full-length sAPP was found in N2a cells transfected with mutant APP cDNA significantly decreased with (P=0.03) and C-terminal fragment (C99), C-terminal fragment (C83) was significantly decreased with (P=0.001) and (P=0.002) in ligand 1 treatment in mAPP+ligand 1 teared N2a cells.
Figure 7A:
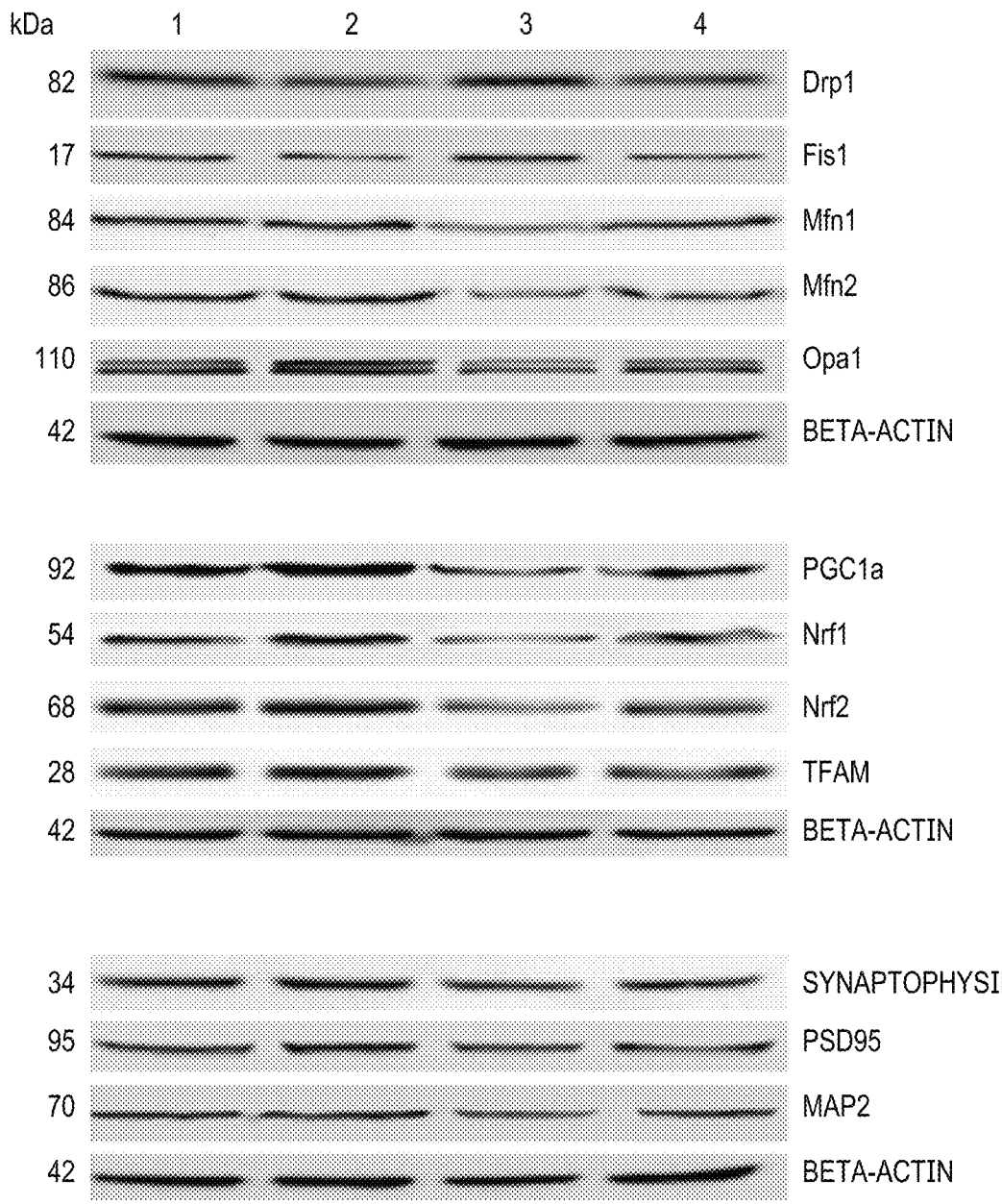
FIGS. 7A and 7B show representative immunoblotting analysis of ligand 1 protection of mitochondrial structural proteins.
Figure 7B:
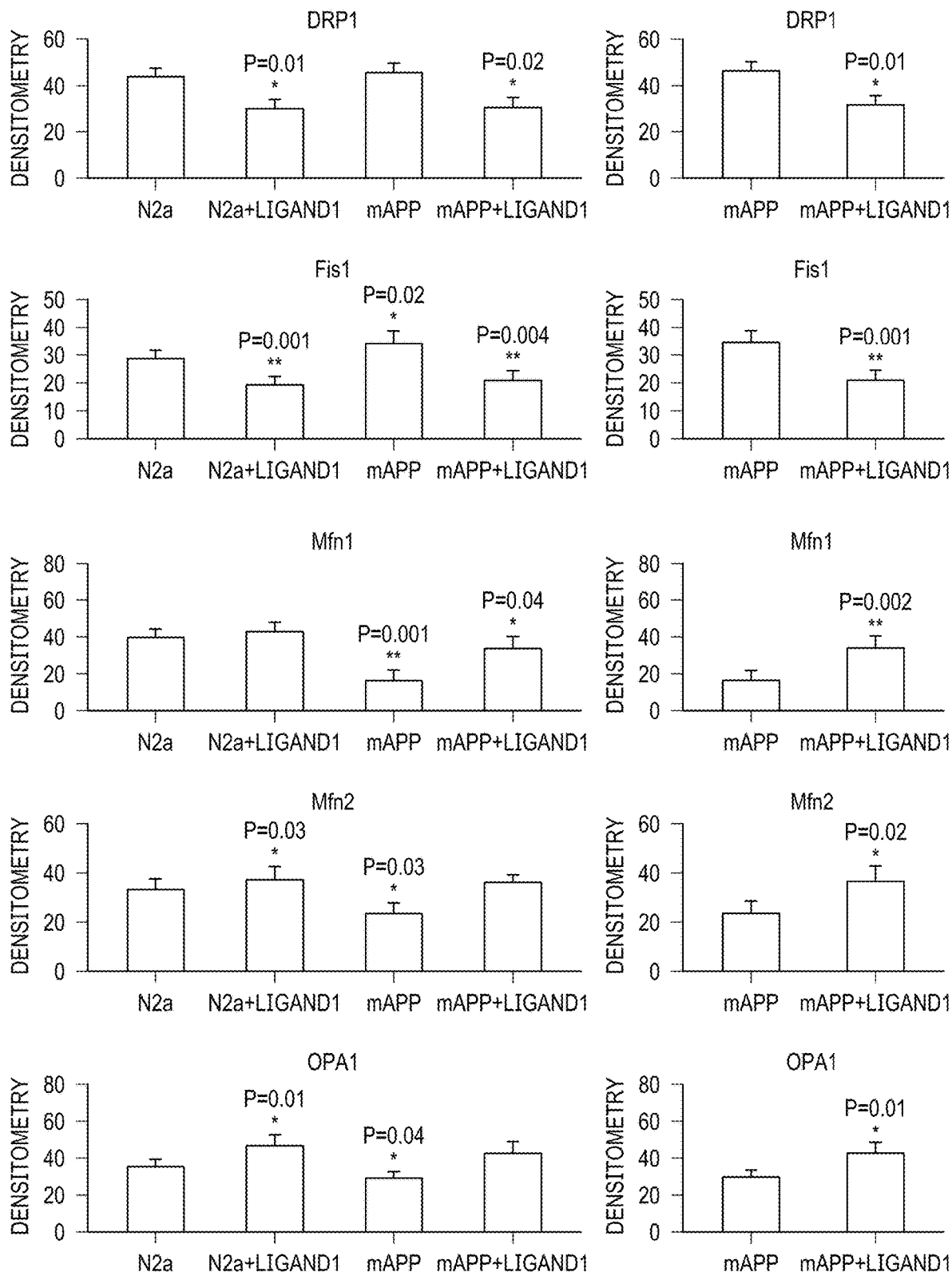
Figure 7C:
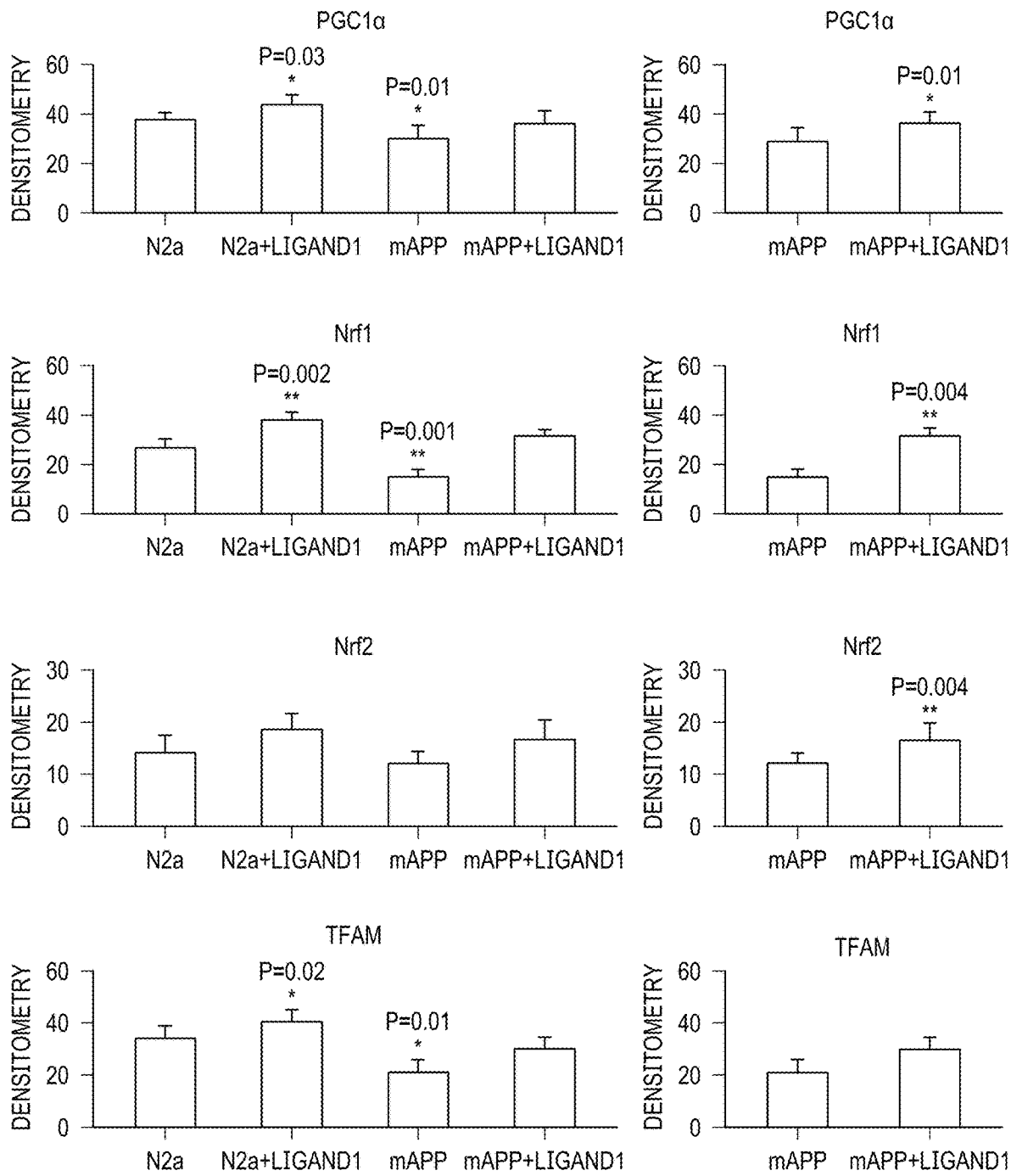
Figure 7D:
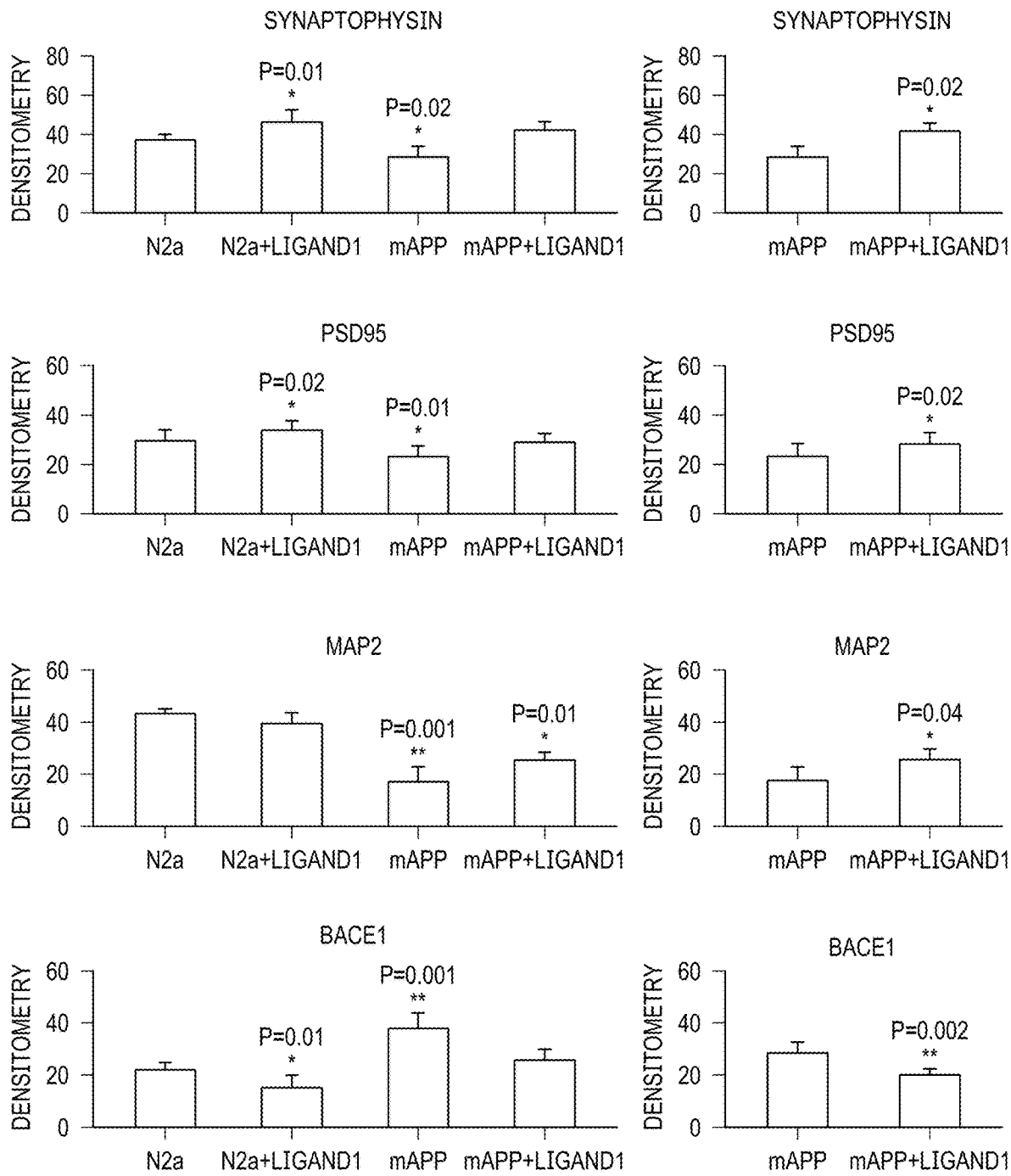

Comparison with untransfected cells Aβ. Mutant APP and C-terminal fragments (CTF), BACE1 levels were significantly reduced in ligand 1 treated cells relative to mAPP cells (P=0.03); CTF-99 (P=0.001); CTF-88 (P=0.002) (FIG. 6). In mAPP cells compared with ligand 1 treated mAPP cells, Drp1 protein levels were significantly decreased (P=0.01) and Fis1 (p=0.001) (FIG. 7). In contrast, increased levels of mitochondrial fusion proteins, Mfn1 (P=0.002), Mfn2 (P=0.002) and Opa1 (P=0.01), were found in mAPP+ligand 1 treated cells compared with mAPP cells. Mitochondrial biogenesis proteins (PGC1α, (P=0.01); Nrf1, (P=0.004); Nrf2, (P=0.004); TFAM, (P=0.01) were increased in mAPP+ligand 1 treated cells, indicating that Aβ affects mitochondrial biogenesis and ligand 1 reverse the mitochondrial biogenesis by rescuing by these observations concur with the mRNA findings in presences of mAPP (FIG. 7). The levels of synaptic and dendritic protein levels, synaptophysin (P=0.02), PSD95 (p=0.02) and MAP2 (P=0.04), were significantly increased in mAPP+ligand 1 treated cells relative to mAPP transfected cells (FIG. 7).

Immunofluorescence analysis of BACE1, 6E10 and CTF. To determine the effect of ligand 1 on BACE1, 6E10 and C-terminal fragments, immunofluorescence analysis was performed on four different groups of cells: 1) untreated N2a cells versus; 2) N2a+ligand 1; 3); cells transfected with mAPP and 4) mAPP+ligand 1.

Figure 8A:
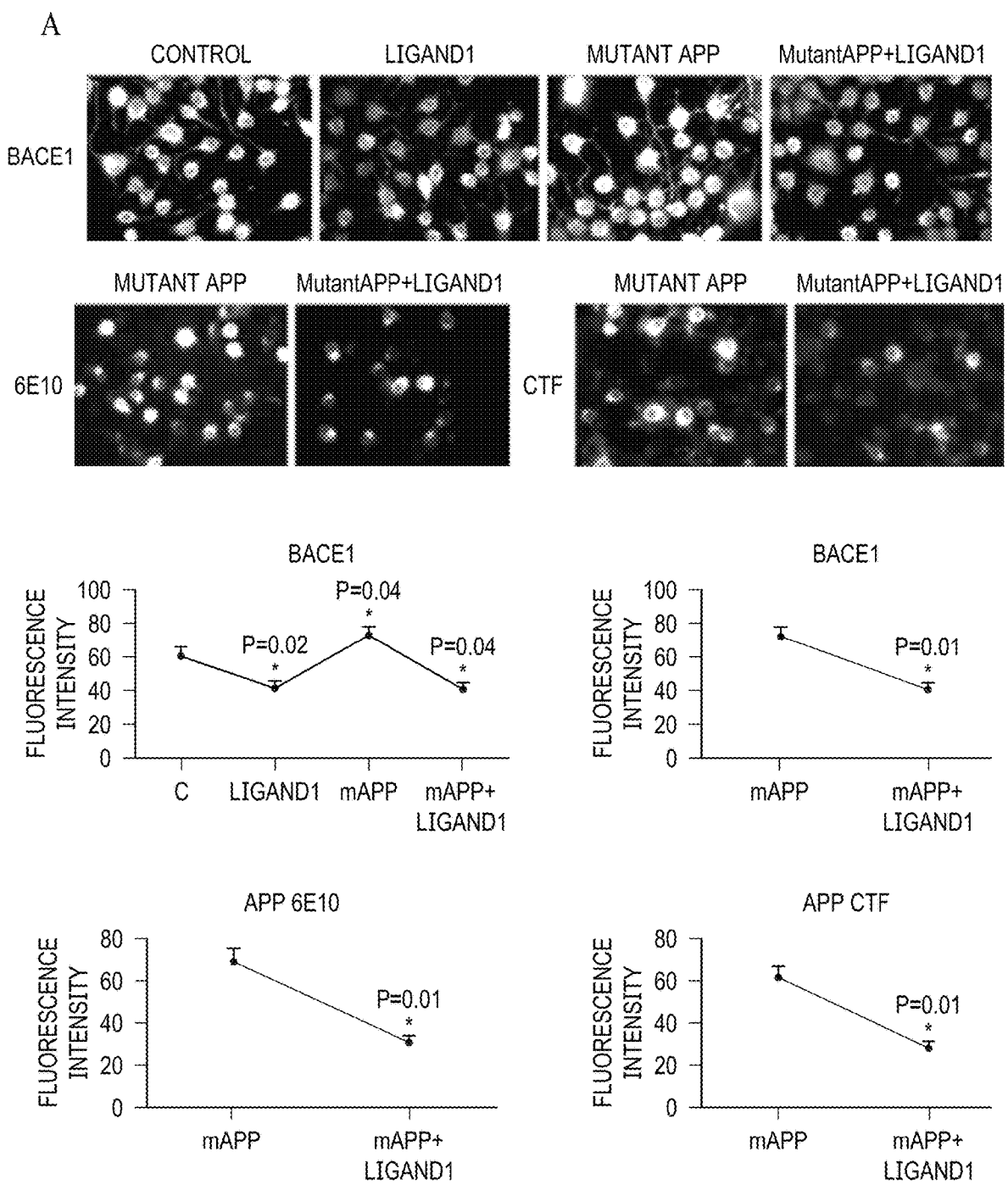
FIGS. 8A and 8B show.

Comparison with untreated cells. Using 6E10 antibody, the inventors also conducted immunofluorescence analyses. mAPP and C-terminal fragment (CTF), BACE1 levels were significantly reduced in ligand 1 treated cells relative to mAPP cells with BACE1 (P=0.01); 6E10 (P=0.01); CTF (P=0.01) (FIG. 8A), indicating that a ligand 1 inhibits mutant APP and reduces Aβ levels.

Transmission electron microscopy. To determine the effects of ligand 1 on the number and length of mitochondria, the inventors used transmission electron microscopy on cells with untreated N2a cells, N2a+mAPP, mAPP, and mAPP+ligand 1.

Figure 8B:
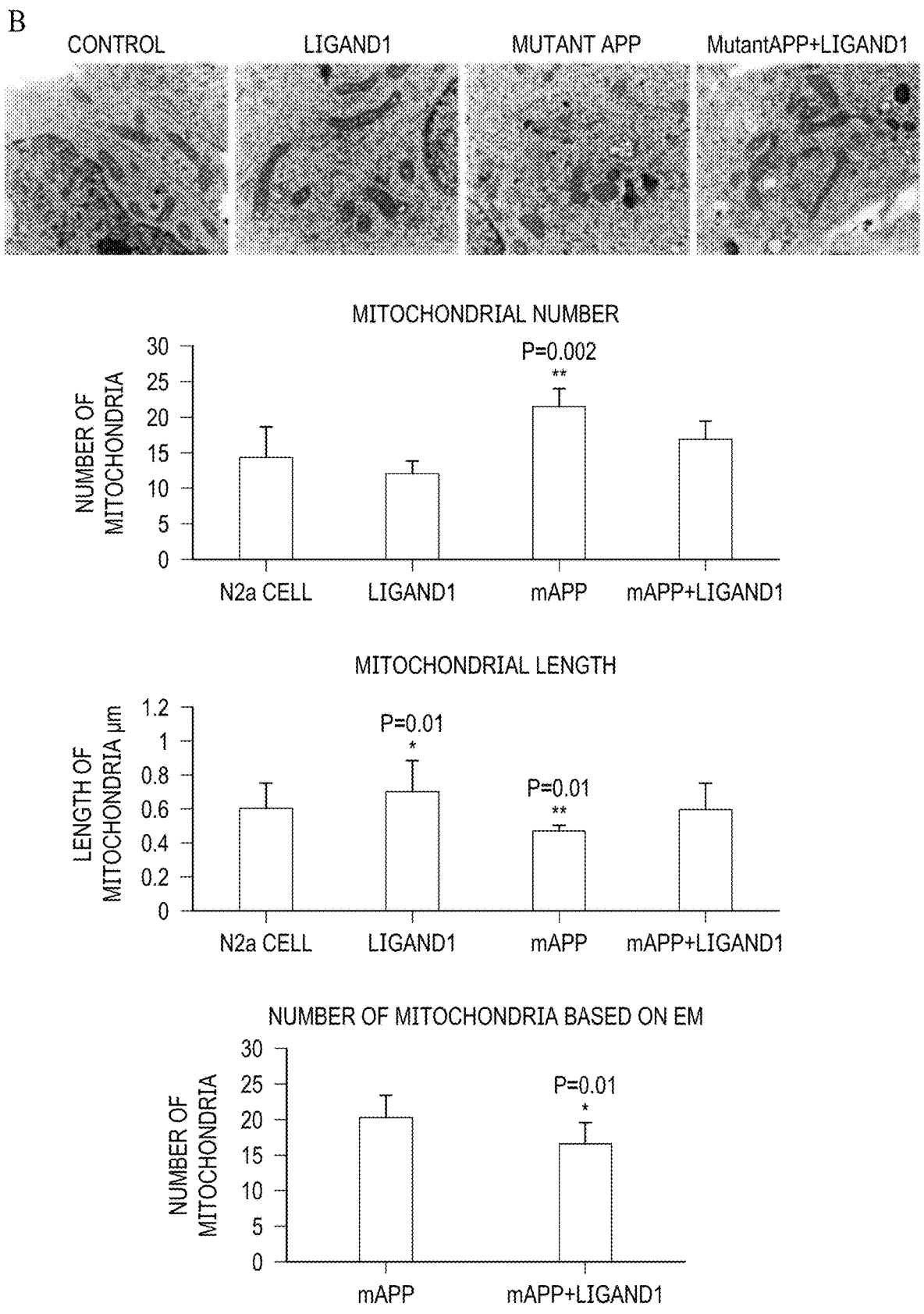

Mitochondrial number in Ligand 1-treated N2a cells. The inventors found a significantly increased number of mitochondria in N2a cells treated with mAPP at (P=0.002) relative to other groups (FIG. 8B), when compared with the mAPP and mAPP+ligand 1, suggesting that ligand 1 reduces mitochondrial fission with (P=0.01). Significantly increased number of mitochondria in mAPP cells relative to untreated cells (P=0.002), suggesting that mAPP enhances mitochondrial number, in other words mAPP enhances mitochondrial fragmentation. On the other hand, ligand 1 treatment reduced the number of mitochondria relative to mAPP+ligand 1 (P=0.01), suggesting that ligand1 treatment reduces mitochondrial fragmentation.

Mitochondrial length in Ligand 1-treated N2a cells. Mitochondrial length the inventors also measured mitochondrial length in order to understand whether ligand 1 treatment alters mitochondrial length (μm). As shown in (FIG. 8B), the inventors found mitochondrial length is significantly increased in cells treated with ligand 1 relative to untreated cells. On the contrary, mitochondrial length is not significantly reduced in mAPP cells (P=0.01) relative to mAPP+ligand 1 treated cells. Mitochondrial number is significantly decreased in mAPP (P=0.01) cells relative to cells treated with ligand 1 and the mitochondrial length is not significantly decreased. These findings indicate that ligand 1 reduces excessive mitochondrial fragmentation in AD neurons.

Using bioinformatics and molecular docking tools, the inventors investigated pharmacophore ligands for BACE1. BACE1 protein contains many catalytic residues, which serve as targets for new drugs. In order to develop drugs for these targets, the inventors identified catalytic core domain active site of BACE1 through CASTp analysis. The resultant CASTp calculations revealed that major core catalytic residues in domain 1 are located at binding pockets i.e. 29, 31 and these pocket motifs are ASP 32, GLY 34, SER 35, SER 36, ASN 37, VAL 69 and ARG 128. The powerful protease ligand pepstatin (aspartyl protease inhibitor) selected as the pharmacophore ligand for BACE1 screening. Ligand Scot pharmacophore analysis of BACE1 in presence of pepstatin gave the three best ligand associated pharmacophore residues: ASP 32, THR33 and SER 35. These three key residues set to filter from the Ligand Scot screening, resulting the outcome with 16 best-fitted ligands. Furthermore, molecular docking studies performed for the 16 ligands to find best BACE1 small molecule inhibitor precisely, through molecular docking studies. The molecular docking tool PyRx optimized with 16 pharmacophore ligands, with minimal binding energies and interacted residues. Molecular docking studies of BACE1 results gives the best lead molecules based on docking energies. The inventors selected the top 5 ligands as best lead molecules with docking scores and hydrogen bonding with the BACE1 protein. These top 5 ligand lead molecules expected to inhibit the of BACE1 activity by inhibiting APP processing and Aβ toxicity in AD neurons.

The chemical library screening of PubChem relative structures of pepstatin around 873 molecules was set for pharmacophore screening. Only 16 pharmacophore ligands selected for the molecular docking studies. Further, only five lead molecules considered as best ligands based on the best binding energy and molecular interactions. Ligand molecular interactions with BACE1 were as follows: CID 1008594 with ASP32, THR 33, ARG 56; CID 10048142 with ASP 32, THR 33, LYS 107; CID 10054794 with THR 33, TYR 51, THR 33; CID 100031313 with THR 33, SER 35, THR 95; CID 100034005 with ASP 32, TYR 123, GLU 134. The complete ligand bond length and docking energies are listed in (Table 4). The complete pharmacophore core site where BACE1 inhibition takes place is most likely within the domain1 region, involving catalytic residues ASP 32, GLY 34, SER 35, SER 36, ASN 37 and ARG 128. The five selected ligand-protein interactions are visualization illustrated in (FIG. 3).

Figure 9:
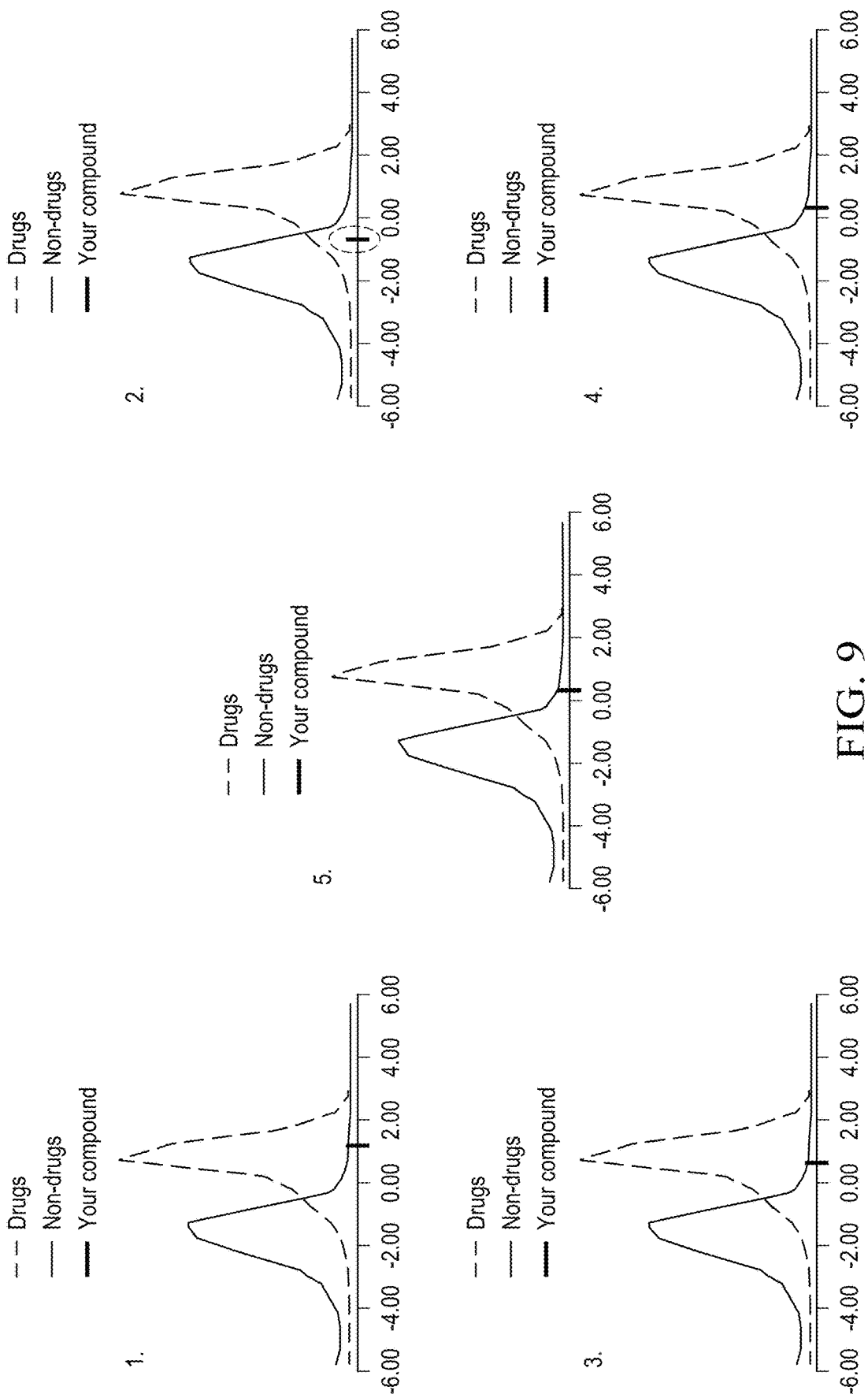
FIG. 9 shows a Molsoft drug likeness prediction for top 5 ranking ligand molecules (Ligand (1.) CID 10008594, (Ligand (2.) CID 10048142, (Ligand (3.) CID 10054794, (Ligand (4.) CID 100031313 (Ligand (5.) CID 1008594, illustrate represents left curve the non-drugs, and right curve represents the drugs and vertical line indicate the ligand property. From all the 5 ligand molecules drug likeness property plots, only one (Ligand (2.) CID 10048142 show in negative value highlighted with a circle remaining all ligands showed good drug likeness properties in Molsoft property explorer.

Drug likeness is a basic property for prospective drugs and includes Lipinski's Rule of Five (molecular weight, Log P-value, No of rotatory bonds and No of H-donor 5 and acceptors 10). Ligand properties were tested Lipinski Rule of Five by submitting to Molsoft server to predict druglikeness properties for top ranking five ligands. Only CID 1008594, CID 100031313, CID 10054794 and CID 10034005 showed good drug-likeness properties with likeness of 1.21, 0.65, 0.31 and 0.30 respectively. The remaining ligand, CID 10048142, showed non-drug like property with −0.69 (FIG. 9).

All 5 top molecules were tested again for ADMET, using admetSAR prediction for the toxicity to confirm their toxic properties. The admetSAR web based analysis gave selected ligands based on the canonical SMILE notation of molecules. Among the best five molecules, only three molecules qualified i.e. CID 1008594, CID 100031313 and CID 10034005 showing the non-toxic and good lead properties (Table 5a). Based on all the above aspects of proposed small molecules only three presented useful and important properties. These included sufficient Blood-Brain Barrier transported capabilities (Table 5b), and computational validations like molecular docking, ADMET/TOX, admetSAR and drug like properties. The most promising, ligand 1 suggested for in vitro validations.

Using cell cultures, the protective effects of ligand 1 were studied in the presence and absence of Aβ. The inventors measured mRNA and protein levels of mitochondrial dynamics, mitochondrial biogenesis, synaptic genes using real time RT-PCR and immunoblotting and immunofluorescence analysis. Aβ found to impair the mitochondrial dynamics (increased fission and decreased fusion). Mitochondrial biogenesis, synaptic activities and mitochondrial function were abnormal in mAPP cells. On the other hand, ligand 1 treated cells showed enhanced fusion activity and reduced fission machinery and increased biogenesis and synaptic proteins. Mitochondrial function and cell viability were elevated in ligand 1 treated cells. Interestingly, ligand 1 treated mAPP cells showed reduced mitochondrial dysfunction, maintained cell viability and mitochondrial dynamics, mitochondrial biogenesis and synaptic activity.

Aβ40 and 42 levels were significantly reduced in ligand 1 treated mAPP cells (FIGS. 4C & 4D) relative to ligand 1 untreated mAPP cells. These observations are interesting and may have therapeutic value for AD. It is possible that ligand 1 blocks/reduces the activity of the BACE1 cleavage site (that is responsible for Aβ40 & 42 production) at C-terminal region of Aβ in mutant APP cells. Additional research is still needed in order to determine how ligand 1 reduces the levels of Aβ40 & 42.

Figure 5:
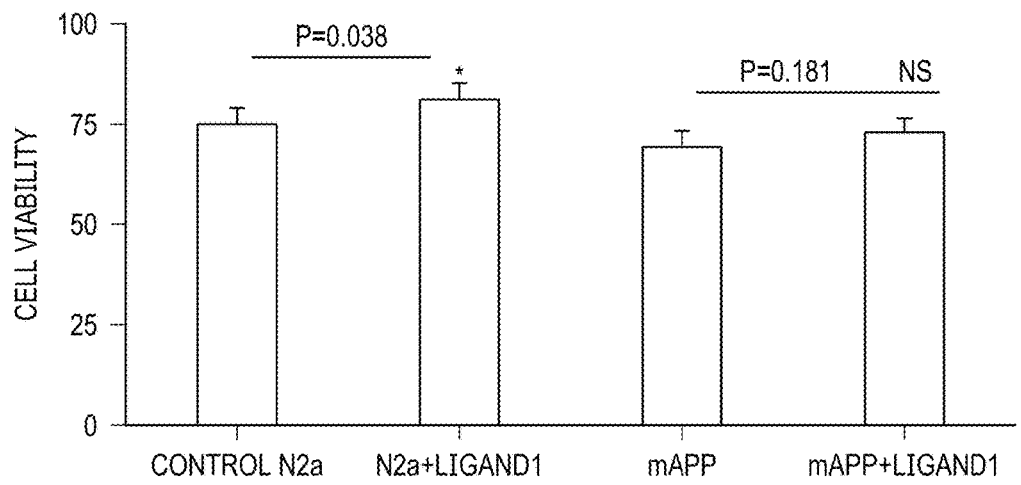
FIG. 5 shows an MTT assay. Cultured mouse neuroblastoma (N2a) cells (first bar control N2a cells), N2a treated ligand 1 (second bar), mAPP transfected N2a cells (third bar) mAPP transfected N2a cells treated ligand 1 (fourth bar). Statistical analysis was done by student T-Test. Control and mutAPP+ligand 1 treatment with (P<0.05), significantly Ligand 1 treated mAPP transfected N2a preserved neurons with ligand 1 protective nature.

Cell viability was also significantly increased in cells treated with ligand 1 (P=0.038) compared with untreated control cells (FIG. 5). Significantly increased cell viability levels were found in cells treated with mAPP+ligand 1 (P=0.181) relative to mAPP cells, suggesting that ligand 1 increases cell viability in the presence of Aβ. These observations indicate that ligand 1 enhances cell survival properties of neurons.

It is well established that mutant APP and Aβ causes lower cell survival and higher apoptotic in AD neurons (45,46). In the current study, the inventors found mAPP cells showed reduced cell survival and increased apoptotic cell death. On the other hand, pharmacophore based ligand 1 molecule enhanced cell survival and reduced apoptotic cell death in mAPP transfected cells. This effect presents strong evidence that ligand 1 is protective against AD neuron cells. These observations warrant further in vivo studies using mouse models of AD.

In cells treated with ligand 1, mitochondrial biogenesis and synaptic activity were enhanced, mitochondrial fission activity was reduced and fusion activity was enhanced. The mRNA and protein data under preventive conditions of ligand 1 were positive; suggesting that ligand 1 prevents mitochondrial structural, biogenesis and synaptic genes from expressing abnormally. Overall, ligand 1 appears to inhibit BACE1 activity and protect the mitochondrial structure by regulating mitochondrial fission, fusion and matrix genes. Furthermore, the protective effects of ligand 1 can be tested in AD mouse models to validate the efficacy of ligand 1 for therapeutic treatments of AD.

In summary, mutant APP cells treated with ligand 1 were found to have reduced levels of BACE1 activity, full length APP and decreased Aβ40 and 42 levels. Ligand 1 treated cells showed reduced mRNA and proteins levels of mitochondrial fission genes; and increased levels of mitochondrial fusion, biogenesis, and synaptic genes relative to neurons transfected with mAPP alone. This indicates that ligand 1 is a BACE1 inhibitor and protective against Aβ-mitochondria- and synaptic-induced toxicities in AD neurons. These observations strongly suggest further verification using AD mouse models before clinical studies using AD patients.

BACE1 inhibitor drugs have had trouble passing clinical trials of Alzheimer's disease with unbefitting molecular behavior of drugs. However, there are substantial challenges to developing an effective therapeutic drug that delay the progression of AD. To date, there are a very few reliable drugs that delay the progression of AD with minimal side effects. Hence, there is a clear need for in silico development of small molecule inhibitors for in vitro models that can recapitulate drug response for a personalized medicine approach. Here, inventors present an in vitro based ligand treatment study with mAPP cells, both from mAPP and ligand treated mAPP cells. To the inventors' knowledge, this is the first small molecule report of a (pepstatin-based ligand mechanism) capable of recapitulating catalytic APP inhibition in AD neurons. This ligand 1 will need further testing for validation in transgenic mouse models. This ligand 1 molecule can bring us closer to an in vitro personalized medicine approach, with BACE1 inhibition in mutant APP cells. Ligand 1 holds great potential for improving, mitochondrial protection and synaptic function in the treatment of AD disease.

Materials and Methods. Computational screening and validations. Active site CASTp calculations. Prediction of active site of the proteins provides valuable information regarding the ligand binding sites and active sites of functional residues. Amyloidonegic pathway protein BACE1 active site information achieved through the CASTp calculations (47). CASTp calculations of BACE1 provides a valuable information and core tunnels with functional residues. CASTp measures the BACE1 associated with structural pockets and cavities based on weighted delaunay triangulation and the alpha complex geometry algorithm. BACE1 illustrations and the listing of wall atoms and mouth atoms for each pockets were visualized in CASTp calculations (47).

Ligands selection screening. The aspartyl protease inhibitors like pepstatin (3S,4S)-4-amino-3-hydroxy-6-methylheptanoic acid) are very well-known inhibitors of aspartic proteinase with the most literature available (FIG. 1A).

However, very few experimental validations of BACE1 inhibitors for pharmacological drug intervention are available. Molecular neuronal toxicity with pathological associations of mitochondrial interactions of Aβ proteins was poorly understood in AD brains (48). Hence, the inventors designed a pharmacophore model of pepstatin structurally similar to the ligand BACE1 inhibitors with proximal validations (FIG. 1B). The pepstatin-based pharmacophore was set to find the best-fitted and molecular interactions with prospective BACE1 inhibitors to find better molecules to treat AD. Structurally the BACE1 protein contains two domains: one external domain, starting from 14 A to 144 A—the residues of domain1, and the second, from 149 to 389—the residues of domain 2. Here AD pathology presents clear evidence that catalytic cleavage of external APP caused by the β-secretase leads to Aβ peptide. At domain 2 starting from 147, there is successive internal cleavage within the membrane processed by the second catalytic cleavage enzyme γ-secretase leading to the formation of 32 to 42 APP peptides (49). The aggregation of 40 to 42 beta amyloid peptide in the AD brains is one of the essential processes of APP formation during the successive first catalytic cleavage of APP. Pharmacophore design of BACE1 inhibitors is a novel method for diminishing the activity of APP formation, and is gaining special attention in AD drug discovery.

The structure of pepstatin (CID 5478883) an aspartic protease inhibitor used as reference ligand BACE1 inhibitor along with its related analogs were screened and from PubChem database (pubchem.ncbi.nlm.nih.gov), which is a noncommercial storehouse of small compounds (50). In the structure, data format (.sdf) relative that small structure related of compounds of pepstatin was downloaded and prepared a chemical library data for pharmacophore-based screening.

Pharmacophore design. LigandScout (LS) Pharmacophore tool helps to automated construction of BACE1 3-D pharmacophore models of structural knowledge of macromolecules/inhibitor complexes (51). A pharmacophore derived model of BACE1 developed on the basis of X-ray crystal structures of protein in complex with pepstatin ligand (CID 5478883). Based on LS rule, compound options embody hydrogen bond donors (HBD) and acceptors (HBA) as focused vectors along with negative and positive ionizable spheres, furthermore as lipophilic regions are taken an account to create a pepstatin-BACE1 pharmacophore. Thus, the common pharmacophore features properties of all the generated list of ligands prepared a separate sheet, and used as the qualified ligands, in further molecular docking studies of BACE1 protein.

Molecular Docking. Molecular docking studies were carried out by the Pyrx AutoDock Vina docking tool using 16 minimized pharmacophore leads molecules against the predicted binding site of the optimized conformation of the ligands through AutoDock in PyRx software (45). Active site dimensions were set as grid (XYZ axis) size center X: 61.9702, Y: 29.2373, Z: −0.4286 and dimensions (angstrom) X: 58.6169, Y: 30.7325, Z: 48.9286 to dock with ligands. The molecular docking simulations were set with 10 maximum exhaustiveness for each ligand molecule in PyRx docking setup. The ligands binding energies, conformations and hydrogen bond interactions, bond distance of amino acid residues were calculated through molecular 3D visualization tool PyMol.

In silico drug-likeness properties. Drug-Likeness explorer molsoft tool (http://www.molsoft.com/mprop/) works to investigate the best docking top 5 lead molecules were subjected for drug discovery process to test their drug-likeness, before going to further in vitro evaluations of BACE1 inhibitors. Keeping in all aspects to lead molecules (ligands) must obey the Lipinski Rule of 5 (RO5), as well as drug like properties during the drug discovery process. The best leads compounds must qualify the other possible designate characters, as their molecular mass is a smaller amount than 500 Daltons. Lipophilicity of ligands expressed in an amount referred to as Log P is a smaller amount than 5 is referred. The number of groups within the compound that may give hydrogen atoms to hydrogen bonds must be a smaller amount than 5. The number of groups that may settle for hydrogen atoms to make hydrogen bonds is a smaller amount than 10 were considered as best possible therapeutic ligand features.

AdmetSAR properties. The computational predictions of pharmacokinetic properties of ligands like those that drug-like properties and ADMET/TOX (absorption, distribution, metabolism, elimination, and toxicity) were investigated through online ADMET property explorer server Admet-SAR (52), must curate small compound libraries and perform computational prediction, with support computed atom contributions.

In vitro biological validation of ligands. Based on the computational validations like molecular docking scores and better binding interactions, ADMET/TOX, drug-likeness properties ligand 1, showed good properties for further biological validations. Ligands, 1 exhibited a good molecular docking score and better binding interactions compared to the other molecules. Therefore, the inventors decided to quantify the biological effects of Ligand 1 in AD pathogenesis. Therefore, the inventors treated transfected AD neurons (mAPP N2a cells) with Ligand 1 and quantified the effect of ligand 1 on ELISA inhibition studies of Aβ 40 and 42, and confirm that ligand 1 is more promising in BACE 1 inhibition in AD process. Furthermore, the inventors tested ligand 1 properties by checking like cell viability, mRNA and protein levels of mitochondrial dynamics, biogenesis and synaptic genes, immunoblotting assays and immunohistochemistry and electron microscopy of mitochondrial morphology structure.

Cell culture work. Chemicals and Reagents. The Ligands 1 was purchased from TimTech, LCC Chemical Company (Newark, DE, USA); Mutant APPSwe/Ind cells: The inventors purchased mutant APPSwe cDNA clone (pCAX-APP Swe/Ind) from Addgene. www.addgene.org and verified expression of mutant APP APPSwe/Ind cDNA and further sub-cloned into a mammalian expression vector; and N2a cells were purchased from American Type Culture Collection (ATCC) (Manassas, VA, USA). Dulbecco's Modified Eagle Medium (DMEM) and Minimum Essential Medium (MEM), penicillin/streptomycin, Trypsin-EDTA, and fetal bovine serum were purchased from GIBCO (Gaithersberg, MD, USA).

Figure 10:
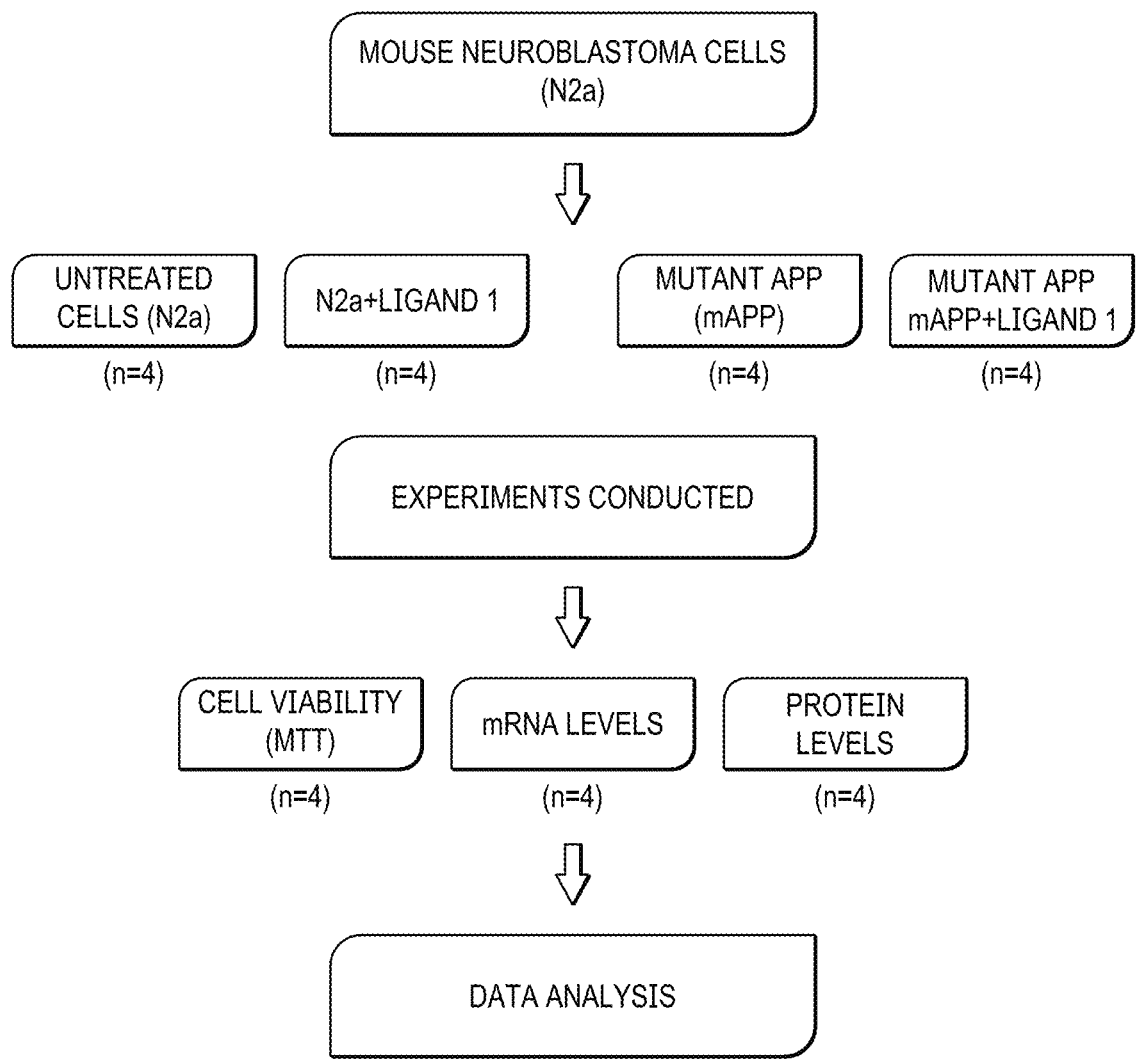
FIG. 10 shows the experimental design of BACE1 inhibition and protective effects of mitochondria structural integrity and biogenesis of ligand 1 in Alzheimer's disease.

The N2a cells grown for 6 days in a serum-free medium (1:1 mixture of DMEM and OptiMEM, plus penicillin and streptomycin (Invitrogen, Carlsbad, CA, USA) until the cells developed neuronal processes. As shown in (FIG. 10), these cells were used for 4 groups—one control group and 3 treatment groups. 1) untreated N2a cells (the control group), 2) N2a cells treated with ligand 1 (N2a+ligand 1), 3) N2a cells transfected mAPP with the (lipofectamine) (20 μM final concentration for 6 hrs (mAPP), 4) N2a cells transfected with mAPP cDNA for 6 hrs, treated with ligand 1 (mAPP+ligand 1 treatment group), N2a cells treated with ligand 1 for 24 hrs and then treated with the mAPP cDNA for 6 hrs (ligand 1+mAPP treatment group). As shown in (FIG. 10), the inventors performed 4 independent cell cultures and treatments for all experiments (n=4).

ELISA Ligand based BACE1 inhibition of Aβ 40 and 42. Ligand 1 BACE1 inhibition, soluble and insoluble Aβ 40 and 42 levels were conducted using sandwich ELISA as described in Manczak et al. (2016)(53). Briefly, protein lysates were from cell pellets in a Tris-buffered saline (pH 8.0) containing protease inhibitors (20 mg/ml pepstatin A, aprotinin, Phosphoramidon and leupeptin; 0.5 mM phenylmethanesulfonyl fluoride and 1 mM ethyleneglycol-bis (flaminoethyl ether)-NN tetra acetic acid). Samples were sonicated briefly and centrifuged at 10 000 g for 20 min at 4° C. The soluble fraction was used to determine the soluble Aβ by ELISA. For each sample, Aβ1-40 and Aβ1-42 were measured with commercial colorimetric ELISA kits (Biosource International, Camarillo, CA, USA) specific for human. A 96-well plate was used, following the manufacturer's instructions. Each sample was run in duplicate. Protein concentrations of the homogenates were determined following the BSA method, and Aβ was expressed as pg Aβ/mg protein.

Cell viability and apoptotic cell death MTT assay. Ligand 1 treated N2a cells, cell based apoptosis assay was performed using Cellometer Vision CBA Image Cytometry System (Nexcelom Bioscience LLC, Lawrence, MA) with two fluorophore Annexin V-FITC and Propidium Iodide (PI) staining solution, according to manufacturer's instructions. Briefly, cells were harvested using trypsin, then spin down at 300 g for three minutes and pellets were washed with 1×PBS, cells were counted using hematocytometer. Collected 100,000 to 150,000 cells and cells/pellet was resuspended in 40 μl of Annexin V binding buffer. 5 μl each of Annexin V-FITC reagent (upper boxes) and PI (lower boxes) were added to binding buffer containing cells; gently mix solution by pipetting up and down ten times, then incubate for 15 min at RT in the dark; after incubation, add 250 μl of 1×PBS and spin down at 300 g for three minutes, then re-suspended the cell pellets in 50 μl of (Annexin V) binding buffer, then assess the cells apoptosis. Live and apoptotic were differentiated using dyes.

mRNA levels of mitochondrial dynamics and mitochondrial biogenesis and synaptic genes. Using the reagent TriZol (Invitrogen), the inventors isolated total RNA from 4 independent treatments of N2a cells (n=4) from control (untreated N2a cells) and experimental treatments (N2a cells treated with Ligand 1; N2a cells transfected with mAPP; N2a cells transfected with mAPP and then treated with Ligand 1. Using primer express Software (Applied Biosystems), the inventors designed the oligonucleotide primers for the housekeeping genes β-actin, GDPH; APP-related genes (APP, BACE1 and PSN1); mitochondrial structural genes; fission (Drp1 and Fis1); fusion genes (MFN1, MFN2, Opa1) (54), mitochondrial biogenesis genes (PGC1α, Nrf1, Nrf2, and Tfam) (Manczak et al., 2019), and synaptic proteins (SYN, PSD95 and MAP2). The primer sequences and amplicon sizes are listed in (Table 1). With SYBR-Green chemistry-based quantitative real-time RT-PCR, the inventors measured mRNA expression of the genes mentioned above as described by Manczak et al. 2019(54). Briefly, 2 μg of DNAse-treated total RNA was used as starting material, to which the inventors added 1 μl of oligo (dT), 1 μl of 10 mM dNTPs, 4 μl of 5× first strand buffer, 2 μl of 0.1 M DTT, and 1 μl RNAse outout. The reagents RNA, dT), and dNTPs were mixed first, then heated at 65° C. for 5 min, and finally chilled on ice until the remaining components were added. The samples were incubated at 42° C. for 2 min, and then 1 μl of Superscript II (40 U/μl) was added. The samples were then incubated at 42° C. for 50 min, at which time the reaction was inactivated by heating at 70° C. for 15 min.

Quantitative real-time PCR amplification reactions were performed in N2a cells in an ABI Prism 7900 sequence detection system (Applied Biosystems, Foster City, CA) in a 25-μl volume of total reaction mixture. The reaction mixture consisted of 1×PCR buffer containing SYBR-Green; 3 mM MgCl2; 100 nm of each primer; 200 nm of dATP, dGTP, and dCTP each; 400 nm of dUTP; 0.01 U/μl of AmpErase UNG; and 0.05 U/μl of AmpliTaq Gold. A 20 ng cDNA template was added to each reaction mixture.

The CT-values of β-actin was tested to determine the unregulated endogenous reference gene in N2a cells that were treated with Aβ and protective molecules, and in untreated N2a cells. In the latter case, the CT-value was similar in untreated and N2a cells treated with MTAs and Aβ. The CT-value is an important quantitative parameter in real-time PCR analysis as described in Gutala and Reddy (2004) (55). All RT-PCR reactions were carried out in triplicate, with no template control. The PCR conditions were: 50° C. for 2 min and 95° C. for 10 min, followed by 40 cycles of 95° C. for 15 sec and 60° C. for 1 min. The fluorescent spectra were recorded during the elongation phase of each PCR cycle. To distinguish specific amplicons from non-specific amplifications, a dissociation curve was generated. The CT-values were calculated with sequence-detection system (SDS) software V1.7 (Applied Biosystems) and an automatic setting of base line, which was the average value of PCR, cycles 3-15, plus CT generated 10 times its standard deviation. The amplification plots and CT-values were exported from the exponential phase of PCR directly into a Microsoft Excel worksheet for further analysis.

The mRNA transcript level was normalized against β-actin at each dilution. The standard curve was the normalized mRNA transcript level, plotted against the log-value of the input cDNA concentration at each dilution. To compare β-actin, and neuroprotective markers, relative quantification was performed according to the CT method (Applied Biosystems; (55). Briefly, the comparative CT method involved averaging triplicate samples, which were taken as the CT values for β-actin, and neuroprotective markers. β-actin normalization was used in the present study because β-actin CT values were similar for the N2a cells treated with Aβ, for the neuroprotective molecules, mitochondrial ETC genes, mitochondrial structural genes and for the untreated N2a cells. The ΔCT-value was obtained by subtracting the average β-actin CT value from the average CT-value of for the neuroprotective genes, peroxiredoxins, mitochondrial ETC genes, and mitochondrial structural genes. The ΔCT of N2a cells was used as the calibrator. The fold change was calculated according to the formula 2−(ΔΔCT), where ΔΔCT is the difference between ΔCT and the ΔCT calibrator value.

To determine the statistical significance of mRNA expression in untreated N2a cells and N2a cells treated with ligand 1, and N2a cells transfected with mAPP. A combination of N2a+ligand 1, and mAPP+ligand 1, the CT value difference between untreated N2a cells and treated N2a cells was used in relation to β-actin normalization, and statistical significance was calculated using one-way ANOVA.

Immunoblotting analysis. Immunoblotting analysis was performed using protein lysates prepared from N2a transfected and transfected mutant AβPP cDNA using 6E10 antibody that recognizes mutant full-length AβPP and Aβ as described in (56). Twenty μg protein lysates were resolved on a 4-12% Nu-PAGE gel (Invitrogen). The resolved proteins were transferred to nylon membranes (Novax Inc., San Diego, CA, USA) and were then incubated for 1 hour at room temperature with a blocking buffer (5% dry milk dissolved in a TBST buffer). The nylon membranes were incubated overnight with the primary antibody (6E10-1:500 monoclonal, BioLegend, San Diego, CA). The membranes were washed with a TBST buffer 3 times at 10-minute intervals and were then incubated for 2 hours with appropriate secondary antibody Sheep anti-mouse HRP 1:10,000, followed by 3 additional washes at 10-minute intervals. Proteins were detected with chemiluminescence reagents (Pierce Biotechnology, Rockford, IL, USA), and the bands from immunoblots were visualized.

Immunofluorescence analysis of BACE1, 6E10 and CTF. To determine BACE1, 6E10, CTF inhibition, mitochondrial network, immunofluorescence analysis was performed using mutant AβPP cells and untransfected N2a and TOM20 antibody as described in (35). The fixed cells were washed with warm PBS, fixed in freshly prepared 4% paraformaldehyde in PBS for 10 minutes, then washed with PBS and permeabilized with 0.1% Triton-X100 in PBS. They were blocked with a 1% blocking solution (Invitrogen) for 1 hour at room temperature. All sections were incubated overnight with TOM20 antibody (1:250 dilution). After incubation, the cells were washed 3 times with PBS, for 10 minutes each. The cells were incubated with a secondary antibody conjugated with Fluor 488 (Invitrogen) for 1 hour at room temperature. The cells were washed 3 times with PBS and mounted on slides. Photographs were taken with a multiphoton laser scanning microscope system (ZeissMeta LSM510). To quantify the immunoreactivity of TOM20 antibody for each treatment, 10-15 photographs were taken at ×40 magnifications, and statistical significance was assessed, using one-way ANOVA for TOM20 protein.

Transmission electron microscopy of mitochondria. To determine the protective effects ligand 1 the number and morphology of mitochondria and the rescue effects of Ligand 1, on Aβ induced mitochondrial toxicity. The inventors conducted transmission electron microscopy (TEM) of N2a cells from control and experimental treatments (n=4). Treated and untreated N2a cells were fixed in 100 mM sodium cacodylate (pH 7.2), 2.5% glutaraldehyde, 1.6% paraformaldehyde, 0.064% picric acid, and 0.1% ruthenium red. They were gently washed and post-fixed for 1 hr in 1% osmium tetroxide plus 08% potassium ferricyanide, in 100 mM sodium cacodylate, pH 7.2. After a thorough rinsing in water, the N2a cells were dehydrated, infiltrated overnight in 1:1 acetone:Epon 812, infiltrated for 1 hr with 100% Epon 812 resin, and embedded in the resin. After polymerization, 60- to 80-nm thin sections were cut on a Reichert ultramicrotome and stained for 5 min in lead citrate. They were then rinsed and post-stained for 30 min in uranyl acetate, and then rinsed again and dried. EM was performed at 60 kV on a Philips Morgagne TEM, equipped with a CCD, and images were collected at original magnifications of 1,000-37,000×. The numbers of mitochondria were counted in the control N2a cells (number of cells=50) and experimental groups (number of cells per group=40), and statistical significance was determined, using one-way ANOVA.

Quantification and statistical analyses. Statistical analyses were conducted in two ways: 1). Untreated cells versus cells transfected with mAPP, N2a+ligand 1, mAPP+ligand 1 2). Cells treated with mAPP versus mAPP+ligand 1 for mRNA and protein levels, cell viability and mitochondrial structural and biogenesis using appropriate statistical analysis.

Data and Software Availability. The PDB files that support the findings of this study have been available in Protein Data Bank under accession codes 2ZHT.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

REFERENCES

1. Nieweg, K., Andreyeva, A., van Stegen, B., Tanriover, G., and Gottmann, K. (2015) Alzheimer's disease-related amyloid-β induces synaptotoxicity in human iPS cell-derived neurons. Cell Death. Dis. 6, e1709.
2. Masters, C. L., and Selkoe, D. J. (2012) Biochemistry of Amyloid β-Protein and Amyloid Deposits in Alzheimer Disease. Cold Spring Harb. Perspect. Med. 2, a006262.
3. Haass, C., Kaether, C., Thinakaran, G., and Sisodia, S. (2012) Trafficking and proteolytic processing of APP. Cold. Spring. Harb. Perspect. Med. 2, a006270.
4. Kametani, F., and Hasegawa, M. (2018) Reconsideration of Amyloid Hypothesis and Tau Hypothesis in Alzheimer's Disease. Front. Neurosci. 30, 25.
5. Fenoglio, C., Scarpini, E., Serpente, M., and Galimberti, D. (2018) Role of Genetics and Epigenetics in the Pathogenesis of Alzheimer's Disease and Frontotemporal Dementia. J. Alzheimers. Dis. 62, 913-932.
6. Cai, Y., An, S. S., and Kim, S. (2015) Mutations in presenilin 2 and its implications in Alzheimer's disease and other dementia-associated disorders. Clin. Interv. Aging. 10, 1163-72.
7. Gao, Y., Ren, R. J., Zhong, Z. L., Dammer, E., Zhao, Q. H., Shan, S., Zhou, Z., Li, X., Zhang, Y. Q, Cui, H. L., et al. (2019) Mutation profile of APP, PSEN1, and PSEN2 in Chinese familial Alzheimer's disease. Neurobiol. Aging. 77, 154-157.
8. Bird, T. D. (2008) Genetic aspects of Alzheimer disease. Genet Med. 10, 231-9.
9. Chow, V. W., Mattson, M. P., Wong, P. C., and Gleichmann, M. (2010) An overview of APP processing enzymes and products. Neuromolecular Med. 12, 1-12.
10. Kimura, A., Hata, S., and Suzuki, T. (2016) Alternative Selection of β-Site APP-Cleaving Enzyme 1 (BACE1) Cleavage Sites in Amyloid β-Protein Precursor (APP) Harboring Protective and Pathogenic Mutations within the Aβ Sequence. J. Biol. Chem. 291, 24041-24053.
11. Cole, S. L., and Vassar, R. (2008) The role of amyloid precursor protein processing by BACE1, the beta-secretase, in Alzheimer disease pathophysiology. J. Biol. Chem. 31, 29621-29625.
12. Reddy, P. H., Manczak, M., Mao, P., Calkins, M. J., Reddy, A. P., and Shirendeb, U. (2010) Amyloid-beta and mitochondria in aging and Alzheimer's disease: implications for synaptic damage and cognitive decline. J. Alzheimers. Dis. 20, S499-512.
13. Reddy, P. H. (2013) Amyloid beta-induced glycogen synthase kinase 3β phosphorylated VDAC1 in Alzheimer's disease: implications for synaptic dysfunction and neuronal damage. Biochim. Biophys. Acta. 1832, 1913-21.
14. Mirsafian, H., Mat Ripen, A., and Merican, A. F., (2014) Bin Mohamad S. Amino acid sequence and structural comparison of BACE1 and BACE2 using evolutionary trace method. ScientificWorldJournal; 482463.
15. Hu, H., Chen, Z., Xu, X., and Xu, Y., (2019) Structure-Based Survey of the Binding Modes of BACE1 Inhibitors. ACS. Chem. Neurosci, 10, 880-889.
16. Hasegawa, H., Liu, L., Tooyama, Murayama, S., and Nishimura, M. (2014) The FAM3 superfamily member ILEI ameliorates Alzheimer's disease-like pathology by destabilizing the penultimate amyloid-β precursor. Nat. Commun. 5, 3917.
17. Yan, R., and Vassar, R. (2014) Targeting the β secretase BACE1 for Alzheimer's disease therapy. Lancet Neurol. 13, 319-29.

18. Rajmohan, R., and Reddy, P. H. (2017) Amyloid-Beta and Phosphorylated Tau Accumulations Cause Abnormalities at Synapses of Alzheimer's disease Neurons. J. Alzheimers. Dis. 57, 975-999.
19. Yin, J., Han, P., Song, M., Nielsen, M., Beach, T. G., Serrano, G. E., Liang, W. S., Caselli, R. J., and Shi, J. (2018) Amyloid-β Increases Tau by Mediating Sirtuin 3 in Alzheimer's Disease. Mol. Neurobiol. 55, 8592-8601.
20. Reddy, P. H. (2011) Abnormal tau, mitochondrial dysfunction, impaired axonal transport of mitochondria, and synaptic deprivation in Alzheimer's disease. Brain. Res. 1415, 136-48.
21. Du, H., Guo, L., Yan, S., Sosunov, A. A., McKhann, G. M., and Yan, S. S. (2010) Early deficits in synaptic mitochondria in an Alzheimer's disease mouse model. Proc. Natl. Acad. Sci. USA. 107, 18670-5.
22. Reddy, P. H. (2006) Amyloid precursor protein-mediated free radicals and oxidative damage: implications for the development and progression of Alzheimer's disease. J. Neurochem. 96, 1-13.
23. Panchal, K., and Tiwari, A. K. (2018) Mitochondrial dynamics, a key executioner in neurodegenerative diseases. Mitochondrion. S1567-7249 30120-X.
24. Cowan, K., Anichtchik, O., and Luo, S. (2019) Mitochondrial integrity in neurodegeneration. CNS Neurosci Ther. doi: 10.1111/cns.13105.
25. Birnbaum, J. H., Wanner, D., Gietl, A., Saake, A., Kündig, T. M., Hock, C., Nitsch, R. M., and Tackenberg, C. (2018) Oxidative stress and altered mitochondrial protein expression in the absence of amyloid-β and tau pathology in iPSC-derived neurons from sporadic Alzheimer's disease patients. Stem Cell Res. 27, 121-130.
26. Poirier, Y., Grimm, A., Schmitt, K., and Eckert, A. (2019) Link between the unfolded protein response and dysregulation of mitochondrial bioenergetics in Alzheimer's disease. Cell. Mol. Life. Sci. 76, 1419-1431.
27. Pelegay, E. C., Puzzo F, Yilmazer A, and Cagin U. (2019) Targeting Mitochondrial Defects to Increase Longevity in Animal Models of Neurodegenerative Diseases. Adv. Exp. Med. Biol. 1134, 89-110.
28. Calkins, M. J., Manczak, M., Mao, P., Shirendeb, U., and Reddy, P. H. (2011) Impaired mitochondrial biogenesis, defective axonal transport of mitochondria, abnormal mitochondrial dynamics and synaptic degeneration in a mouse model of Alzheimer's disease. Hum. Mol. Genet. 20, 4515-29.
29. Angelova, P. R., and Abramov, A. Y. (2018) Role of mitochondrial ROS in the brain: from physiology to neurodegeneration. FEBS Lett. 592, 692-702.
30. Otsuka I, Izumi T, Boku S, Kimura A, Zhang Y, Mouri K, Okazaki S, Shiroiwa K, Takahashi M, Ueno Y, Shirakawa O, Sora I, Hishimoto A. (2017) Aberrant telomere length and mitochondrial DNA copy number in suicide completers. Sci. Rep. 7, 3176.
31. Oka, S., Leon, J., Sakumi, K., Ide, T., Kang, D., LaFerla, F. M., and Nakabeppu, Y. (2016) Human mitochondrial transcriptional factor A breaks the mitochondria-mediated vicious cycle in Alzheimer's disease. Sci. Rep. 6, 37889.
32. Dragicevic, N., Mamcarz, M., Zhu, Y., Buzzeo, R., Tan, J., Arendash, G. W., and Bradshaw, P. C. (2010) Mitochondrial amyloid-beta levels are associated with the extent of mitochondrial dysfunction in different brain regions and the degree of cognitive impairment in Alzheimer's transgenic mice. J. Alzheimers. Dis. 20 Suppl 2, S535-50.
33. Manczak, M., Anekonda, T. S., Henson, E., Park, B. S., Quinn, J., and Reddy, P. H. (2006) Mitochondria are a direct site of A beta accumulation in Alzheimer's disease neurons: implications for free radical generation and oxidative damage in disease progression. Hum. Mol. Genet. 15, 1437-49.
34. Cha, M. Y., Han, S. H., Son, S. M., Hong, H. S., Choi, Y. J., Byun, J., and Mook-Jung, I. (2012) Mitochondria-specific accumulation of amyloid β induces mitochondrial dysfunction leading to apoptotic cell death. PLoS One. 7, e34929.
35. Reddy, P. H., Manczak, M., Yin, X., and Reddy, A. P. (2018) Synergistic Protective Effects of Mitochondrial Division Inhibitor 1 and Mitochondria-Targeted Small Peptide SS31 in Alzheimer's Disease. J. Alzheimers. Dis. 62, 1549-1565.
36. Baek, S. H., Park, S. J., Jeong, J. I., Kim, S. H., Han, J., Kyung, J. W., Baik, S. H., Choi, Y., Choi, B. Y., Park, J. S. et al. (2017) Inhibition of Drp1 Ameliorates Synaptic Depression, Aβ Deposition, and Cognitive Impairment in an Alzheimer's Disease Model. J. Neurosci. 37, 5099-5110.
37. Palop, J. J., and Mucke, L. (2010) Amyloid-beta-induced neuronal dysfunction in Alzheimer's disease: from synapses toward neural networks. Nat. Neurosci. 13, 812-8.
38. Pereira, C., Agostinho, P., Moreira, P. I., Cardoso, S. M., and Oliveira, C. R. (2005) Alzheimer's disease-associated neurotoxic mechanisms and neuroprotective strategies. Curr. Drug. Targets. CNS Neurol. Disord. 4, 383-40.
39. Butterfield, D. A., Castegna, A., Lauderback, C. M., and Drake, J. (2002) Evidence that amyloid beta-peptide-induced lipid peroxidation and its sequelae in Alzheimer's disease brain contribute to neuronal death. Neurobiol. Aging. 5, 655-64.
40. Casey, D. A., Antimisiaris, D., and O'Brien, J. (2010) Drugs for Alzheimer's disease: are they effective? P T. 35, 208-211.
41. Morris, G. P., Clark, I. A., and Vissel, B. (2012) Inconsistencies and controversies surrounding the amyloid hypothesis of Alzheimer's disease. Acta. Neuropathol. Commun. 18, 135.
42. Luo, Y., Bolon, B., Kahn, S., Bennett, B. D., Babu-Khan, S, and Denis, P. (2001) Mice deficient in BACE1, the Alzheimer's beta-secretase, have normal phenotype and abolished beta-amyloid generation. Nat. Neurosci. 4, 231-232.
43. Roberds, S. L., Anderson, J., Basi, G., Bienkowski, M. J., Branstetter, D. G., Chen, K. S., Freedman, S. B., Frigon, N. L., Games, D., Hu, K., et al. (2001) BACE knockout mice are healthy despite lacking the primary beta-secretase activity in brain: implications for Alzheimer's disease therapeutics. Hum. Mol. Genet. 10, 1317-1324.
44. Ohno, M., Sametsky, E. A., Younkin, L. H., Oakley, H., Younkin, S. G., and Citron, M. (2004) BACE1 deficiency rescues memory deficits and cholinergic dysfunction in a mouse model of Alzheimer's disease. Neuron. 41, 27-33.
45. Trott, O., and Olson, A. J., (2010) AutoDock Vina: improving the speed and accuracy of docking with a new scoring function, efficient optimization, and multithreading. J. Comput. Chem. 30, 455-461.
46. Dallakyan, S., and Olson, A. J. (2015) Small-molecule library screening by docking with PyRx. Methods. Mol. Biol. 1263: 243-250.
47. Binkowski, T. A., Naghibzadeh, S., and Liang, J. (2003) CASTp: Computed Atlas of Surface Topography of proteins. Nucleic Acids Res. 31, 3352-3355.
48. Singh. S. K., Srivastav, S., Yadav, A. K., Srikrishna, S., and Perry, G. (2016) Overview of Alzheimer's Disease and Some Therapeutic Approaches Targeting Aβ by Using Several Synthetic and Herbal Compounds. Oxid. Med. Cell. Longev. 7361613.
49. Li, N., Liu, K., Qiu, Y., Ren, Z., Dai, R., Deng, Y., and Qing, H. (2016) Effect of Presenilin Mutations on APP Cleavage; Insights into the Pathogenesis of FAD. Front. Aging. Neurosci. 8, 51.
50. Kim, S., Thiessen, P. A., Bolton, E. E., Chen, J., Fu, G., Gindulyte, A., Han, L., He, J., He, S., Shoemaker, B. A., et al. (2016) PubChem Substance and Compound databases. Nucleic. Acids. Res. 44, D1202-13.
51. Wolber, G., and Langer, T. (2005) LigandScout: 3-D pharmacophores derived from protein-bound ligands and their use as virtual screening filters. J. Chem. Inf. Model. 45, 160-169.
52. Cheng, F., Li, W., Zhou, Y., Shen, J., Wu, Z., Liu, G., Lee, P. W., and Tang, Y. (2012) admetSAR: a comprehensive source and free tool for assessment of chemical ADMET properties. J. Chem. Inf. Model. 52, 3099-3105.
53. Manczak, M., Kandimalla, R., Fry, D., Sesaki, H., and Reddy, P. H. (2016) Protective effects of reduced dynamin-related protein 1 against amyloid beta-induced mitochondrial dysfunction and synaptic damage in Alzheimer's disease. Hum. Mol. Genet. 25, 5148-5166.
54. Manczak, M., Kandimalla, R., Yin, X., and Reddy, P. H. (2019) Mitochondrial division inhibitor 1 reduces dynamin-related protein 1 and mitochondrial fission activity. Hum. Mol. Genet. 28, 177-199.
55. Gutala, R. V., and Reddy, P. H. (2004) The use of real-time PCR analysis in a gene expression study of Alzheimer's disease post-mortem brains. J. Neurosci. Methods. 132, 101-7.
56. Reddy, P. H., Manczak, M., Yin, X., Grady, M. C., Mitchell, A., Kandimalla, R., and Kuruva, C. S. (2016) Protective effects of a natural product, curcumin, against amyloid β induced mitochondrial and synaptic toxicities in Alzheimer's disease. J. Investig. Med. 64, 1220-1234.
57. Wang, X., Su, B., Lee, H. G., Li, X., Perry, G., Smith, M. A., Zhu, X. (2009). Impaired balance of mitochondrial fission and fusion in Alzheimer's disease. J. Neurosci. 29, 9090-103.
58. Wang, X., Su, B., Siedlak, S. L., Moreira, P. I., Fujioka, H., Wang, Y., Casadesus, G., Zhu, X. (2008) Amyloid-beta overproduction causes abnormal mitochondrial dynamics via differential modulation of mitochondrial fission/fusion proteins. Proc. Natl. Acad. Sci. USA. 105, 19318-23.

What is claimed is:

1. A method of inhibiting an activity of a BACE1 protein comprising:

contacting the BACE1 protein with a ligand that specifically inhibits at one or more residues selected from SER 35, SER 36, ASN 37 and ARG 128 of the human BACE1 protein, wherein the ligand is selected from:

[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate,

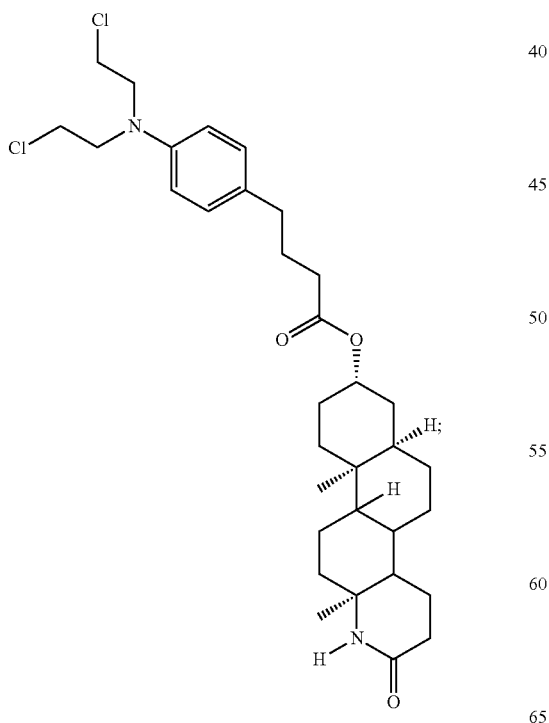

2-(2,5-Dioxopyrrol-1-yl)ethyl 4-[4-[bis(2-chloroethyl) amino]phenyl]butanoate,

4-Chloro-3-fluoro-N-[(1R)-2-methyl-1-(2-methyl-1,2,4-triazol-3-yl)propyl]benzamide, or (2S)-4-[4-[Bis(2-chloroethyl)amino]phenyl]-2-[4-[(2S, 9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

[(1,4-Dihydroxy-9, 10-dioxoanthracen-2-yl)-phenylmethyl] 4-[4-[bis(2-chloroethyl)amino]phenyl]butanoate,

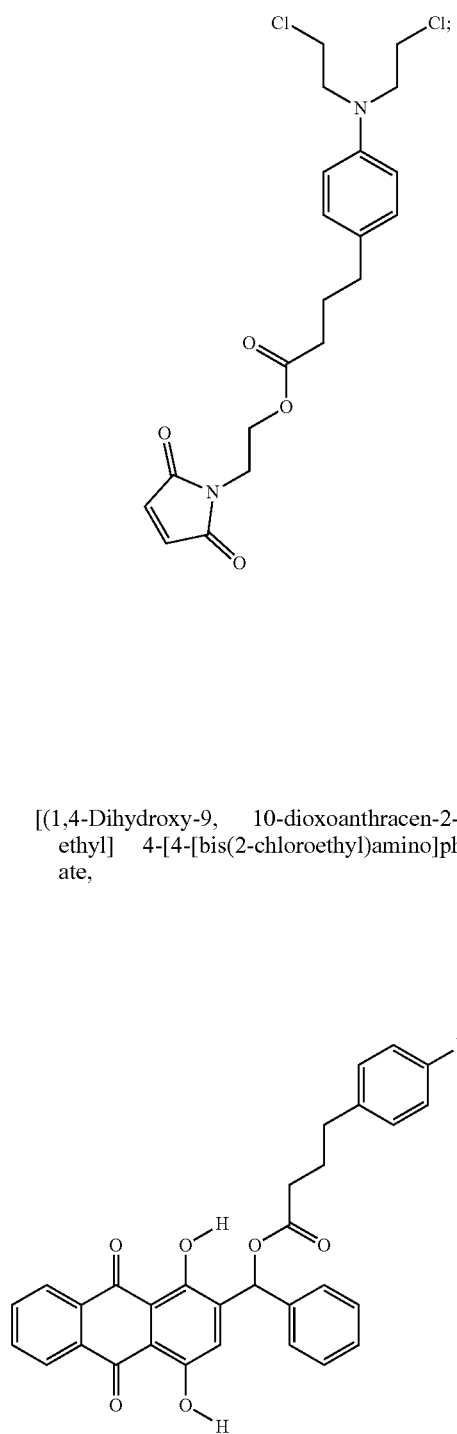

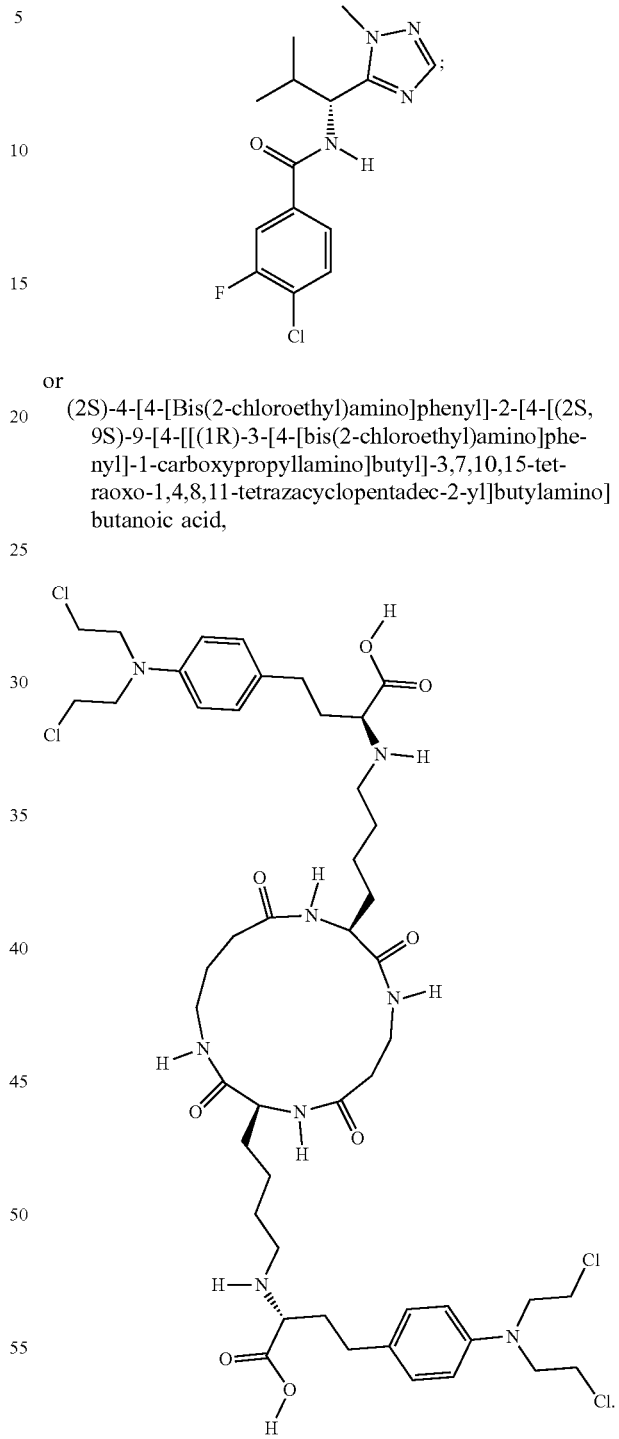

2. The method of claim 1, wherein the ligand is formulated in a pharmaceutical composition.

3. The method of claim 1, wherein the ligand is formulated with a pharmaceutically acceptable carrier, diluent, or excipient.

4. The method of claim 1, wherein the ligand is formulated for oral, enteral, parenteral, pulmonary, or intravenous administration.

5. The method of claim 1, wherein the effective amount of the BACE1 protein inhibitor is between about 1-20 mg kg body weight, 1-7 times per week, 5-15 mg kg body weight, 2-6 times per week, or 8-12 mg kg body weight, 3-5 times per week, or 10 mg kg body weight, 3 times per week.

6. A method of treating Alzheimer's Disease, the method comprising: administering to the individual an effective amount of at least one compound that specifically inhibits human BACE1 protein activity by interaction with one or more residues selected from SER 35, SER 36, ASN 37 and ARG 128, wherein the ligand is selected from:

[(6As,8S,10aS,12aS)-10a,12a-dimethyl-2-oxo-3,4,4a,4b,5,6,6a,7,8,9,10,10b,11,12-tetradecahydro-1H-naphtho[2,1-f]quinolin-8-yl] 4-[4-[bis(2-chloroethyl)amino]phenyl]butanoate,

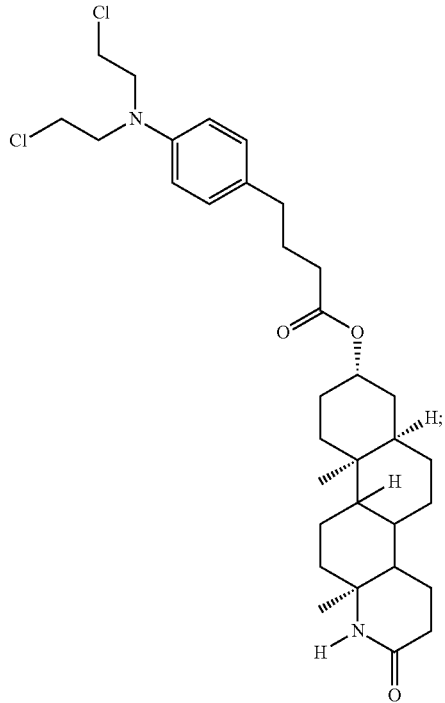

2-(2,5-Dioxopyrrol-1-yl)ethyl 4-[4-[bis(2-chloroethyl)amino]phenyl]butanoate,

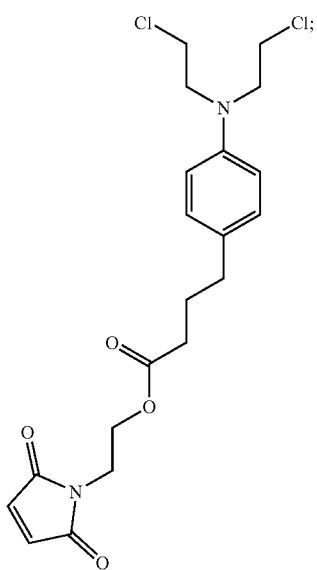 [SMILES: O=C(CCCc1ccc(N(CCCl)CCCl)cc1)OCCN1C(=O)C=CC1=O]

[(1,4-Dihydroxy-9,10-dioxoanthracen-2-yl)-phenylmethyl] 4-[4-[bis(2-chloroethyl)amino]phenyl]butanoate,

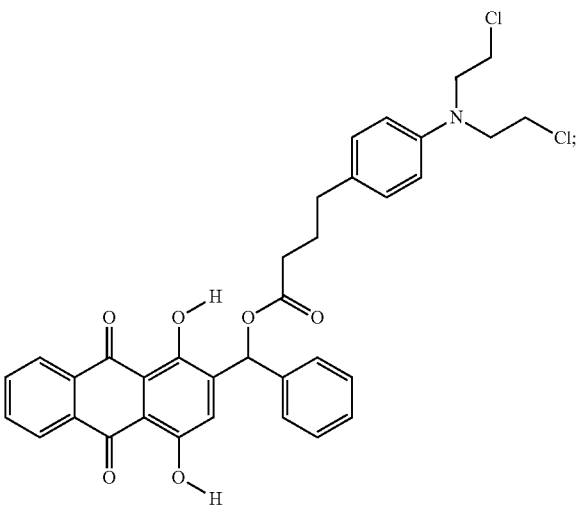 [SMILES: O=C(CCCc1ccc(N(CCCl)CCCl)cc1)OC(c1ccccc1)c1cc(O)c2c(c1O)C(=O)c1ccccc1C2=O]

4-Chloro-3-fluoro-N-[(1R)-2-methyl-1-(2-methyl-1,2,4-triazol-3-yl)propyl]benzamide, or (2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

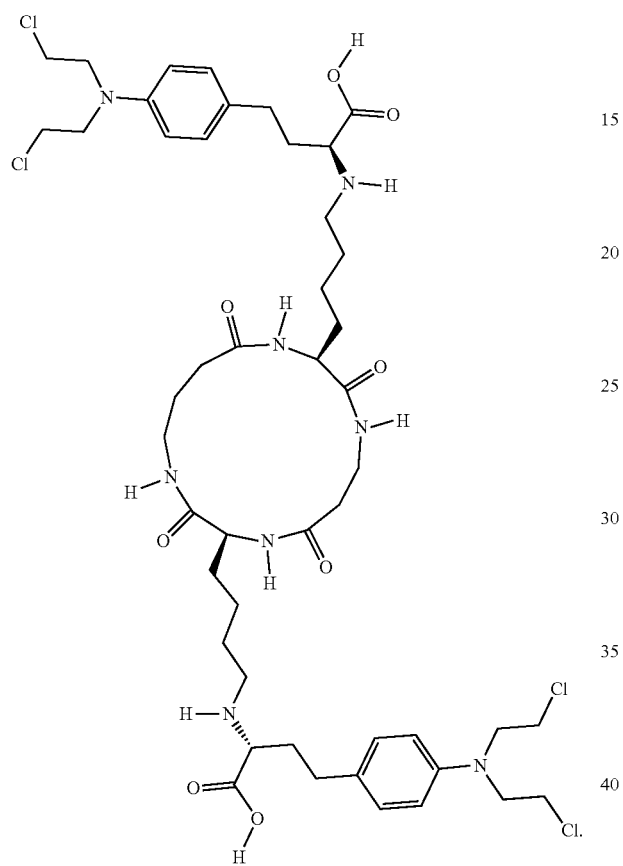

7. The method of claim 6, wherein the compound is formulated in a pharmaceutical composition.

8. The method of claim 6, wherein the compound is formulated with a pharmaceutically acceptable carrier, diluent, or excipient.

9. The method of claim 6, wherein the compound is formulated for oral, enteral, parenteral, pulmonary, or intravenous administration.

10. The method of claim 6, wherein the compound is formulated to provide a dose of an effective amount is between about 1-20 mg kg body weight, 1-7 times per week, 5-15 mg kg body weight, 2-6 times per week, or 8-12 mg kg body weight, 3-5 times per week, or 10 mg kg body weight, 3 times per week.

11. A method of rescuing learning and/or memory deficits caused by Alzheimer's disease, comprising: (a) administering to a subject suffering from the learning and/or memory deficits caused by the Alzheimer's disease a compound selected from:

[(6As,8S,10aS,12aS)-10a, 12a-dimethyl-2-oxo-3,4,4a,4b,5,6,6a,7,8,9,10,10b,11,12-tetradecahydro-1H-naphtho[2,1-f]quinolin-8-yl] chloroethyl)amino]phenyl]butanoate,

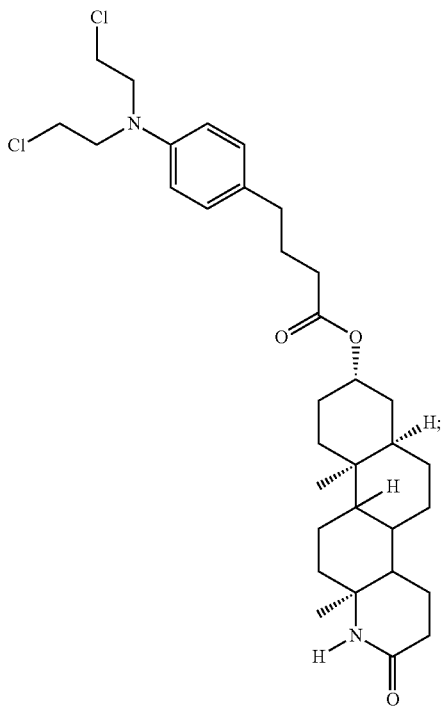

2-(2,5-Dioxopyrrol-1-yl)ethyl 4-[4-[bis(2-chloroethyl)amino]phenyl]butanoate,

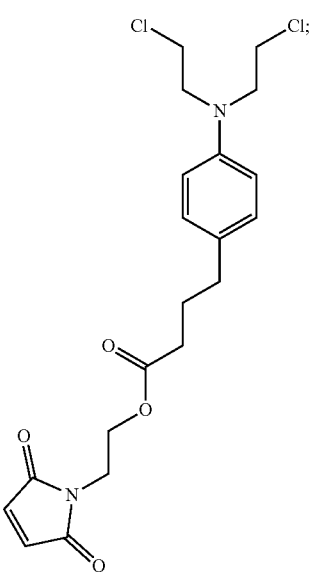 [SMILES: O=C(CCCc1ccc(N(CCCl)CCCl)cc1)OCCN1C(=O)C=CC1=O]

[(1,4-Dihydroxy-9,10-dioxoanthracen-2-yl)-phenylmethyl] chloroethyl)amino]phenyl]butanoate,

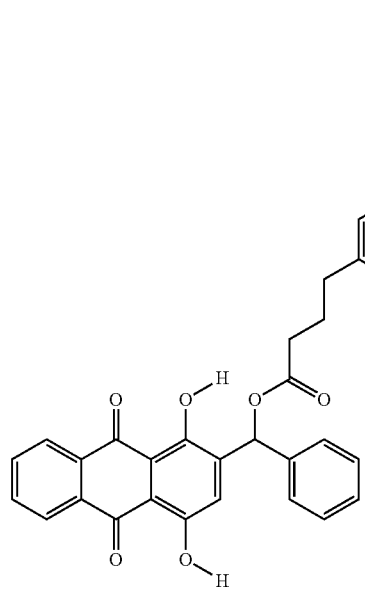

4-Chloro-3-fluoro-N-[(1R)-2-methyl-1-(2-methyl-1,2,4-triazol-3-yl)propyl]benzamide,

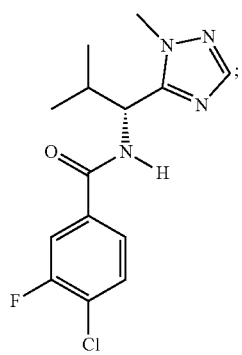

or
(2S)-4-[4-[Bis(2-chloroethyl)amino]phenyl]-2-[4-[(2S,9S)-9-[4-[[(1R)-3-[4-[bis(2-chloroethyl)amino]phenyl]-1-carboxypropyl]amino]butyl]-3,7,10,15-tetraoxo-1,4,8,11-tetrazacyclopentadec-2-yl]butylamino]butanoic acid,

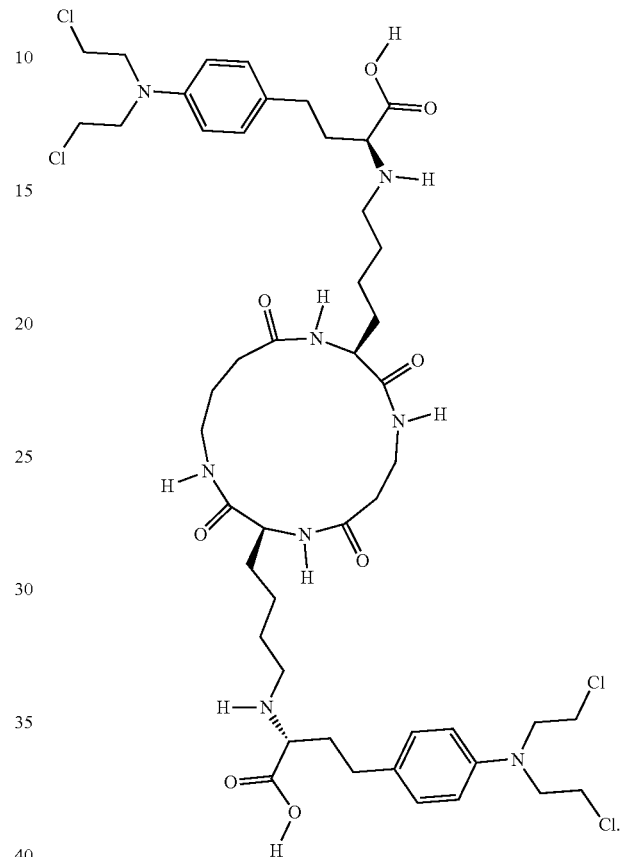

in an effective amount to rescue the learning and/or memory deficits caused by the Alzheimer's disease in the subject; and (b) testing the subject for learning and/or memory performance.

12. The method of claim 11, wherein the compound is formulated in a pharmaceutical composition.

13. The method of claim 11, wherein the compound is formulated with a pharmaceutically acceptable carrier, diluent, or excipient.

14. The method of claim 11, wherein the compound is formulated for oral, enteral, parenteral, pulmonary, or intravenous administration.

15. The method of claim 11, wherein the effective amount of the BACE1 protein inhibitor between about 1-20 mg kg body weight, 1-7 times per week, 5-15 mg kg body weight, 2-6 times per week, or 8-12 mg kg body weight, 3-5 times per week, or 10 mg kg body weight, 3 times per week.

* * * * *